United States Patent
Tosatti et al.

(10) Patent No.: US 10,287,276 B2
(45) Date of Patent: May 14, 2019

(54) HETEROARYL-1,2,4-TRIAZOLE AND HETEROARYL-TETRAZOLE COMPOUNDS FOR CONTROLLING ECTOPARASITES

(71) Applicant: Elanco Tiergesundheit AG, Indianapolis, IN (US)

(72) Inventors: Paolo Tosatti, Binningen (CH); Jean-Yves Wach, Zurich (CH)

(73) Assignee: Elanco Tiergesundheit AG, Basel (CH)

( * ) Notice: Subject to any disclaimer, the term of this patent is extended or adjusted under 35 U.S.C. 154(b) by 0 days.

(21) Appl. No.: 15/556,722

(22) PCT Filed: Apr. 28, 2017

(86) PCT No.: PCT/US2017/030082
§ 371 (c)(1),
(2) Date: Sep. 8, 2017

(87) PCT Pub. No.: WO2017/192385
PCT Pub. Date: Nov. 9, 2017

(65) Prior Publication Data
US 2018/0186778 A1      Jul. 5, 2018

Related U.S. Application Data

(60) Provisional application No. 62/332,004, filed on May 5, 2016.

(51) Int. Cl.
| | |
|---|---|
| C07D 405/14 | (2006.01) |
| C07D 401/04 | (2006.01) |
| C07D 401/14 | (2006.01) |
| C07D 403/04 | (2006.01) |
| A61P 33/14 | (2006.01) |

(52) U.S. Cl.
CPC ............ *C07D 405/14* (2013.01); *A61P 33/14* (2018.01); *C07D 401/04* (2013.01); *C07D 401/14* (2013.01); *C07D 403/04* (2013.01)

(58) Field of Classification Search
CPC .. C07D 401/04; C07D 401/14; C07D 403/04; C07D 405/14; A61P 33/14
See application file for complete search history.

(56) References Cited

FOREIGN PATENT DOCUMENTS

| WO | WO 2006/004924 A2 | 1/2006 | |
|---|---|---|---|
| WO | WO-2008011557 A2 * | 1/2008 | ............ A61K 31/395 |
| WO | WO 2012/080376 A1 | 6/2012 | |

OTHER PUBLICATIONS

Küçükgüzel et al., "Recent Advances Bioactive 1,2,4-triazole-3-thiones," European Journal of Medicinal Chemistry, vol. 97, 2014, pp. 830-870.
Rajput et al., "Importance of ticks and their chemical and immunological control in livestock," Zhejiang Univ. Science B, 2006, 7(11):912-921.
Gould, P.L., "Salt selection for basic drugs," International Journal of Pharmaceutics, 33, 201-217 (1986).
Bastin, R.J. et al., "Salt Selection and Optimisation Procedures for Pharmaceutical New Chemical Entities," Organic Process Research and Development, vol. 4, 427-435 (2000).
Berge, S.M. et al., "Pharmaceutical Salts," Journal of Pharmaceutical Sciences, 66, 1-19 (1977).
International Search Report for Application No. PCT/US17/30082 dated Jun. 16, 2017 (6 pages).
Written Opinion of the International Searching Authority for Application No. PCT/US17/30082 dated Jun. 16, 2017 (8 pages).

* cited by examiner

*Primary Examiner* — Sarah Pihonak
(74) *Attorney, Agent, or Firm* — Joseph Matthew Pletcher

(57) ABSTRACT

The present invention provides compounds of the formula: (I) wherein: X is O or S; $Q^1$ and $Q^2$ are independently $CR^5$ or N, provided at least one of $Q^1$ and $Q^2$ is N; Y is a direct bond or $CH_2$; $R^1$ is H, optionally substituted alkyl, alkenyl, alkynyl, cycloalkylalkyl, benzyl or oxetan-3-yl-$CH_2$—; $R^2$ is optionally substituted phenyl, pyridine, pyrimidine, pyrazine or pyridazine; $R^3$ is alkyl or haloalkyl; $R^4$ is optionally substituted pyridine, pyrimidine, pyrazine or pyridazine; $R^5$ is H, alkyl, haloalkyl, cycloalkyl, alkoxy, alkoxyC(O)— or (alkoxy)$_2$CH—; or a salt thereof. The compounds are useful for controlling ectoparasites on animals.

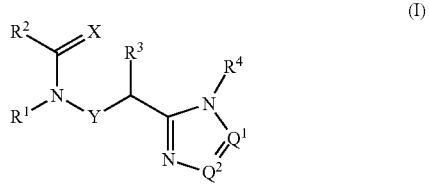

(I)

17 Claims, No Drawings

HETEROARYL-1,2,4-TRIAZOLE AND HETEROARYL-TETRAZOLE COMPOUNDS FOR CONTROLLING ECTOPARASITES

The present invention relates to novel heteroaryl-1,2,4-triazole and heteroaryl-tetrazole compounds, to formulations comprising the compounds and to their use in the control of ectoparasites on animals.

The present invention is in the field of pest control, in particular the control of ectoparasites on animals. Parasitic infections result in significant suffering to the animal, both as a consequence of the infection itself and the diseases transmitted by the parasites. In addition, parasitic infection in livestock animals can result in significant economic loss. This is observed, for example, in the cattle industry where tick infestation, in particular, causes major losses. When ticks feed in large numbers they consume large quantities of blood which can result in anaemia and loss of nutrients. In addition, the irritation caused by the ticks leads to a reduction in food intake by the cattle. AU these factors negatively impact weight gain and milk production (Rajput et al, J. Zhejiang Univ. SCIENCE B, 2006, 7(11):912-921). Furthermore, ticks cause damage to the hide (Rajput et al.) and predispose the cattle to bacterial and fungal infections. A number of diseases are known to be transmitted via tick-borne pathogens, among them are the cattle diseases bovine babesiosis, also known as pyroplastnosis or red water fever, and bovine anaplasmosis, also known as gall sickness (Rajput et al.). These diseases lead to lower weight gain, decreased milk production and increased mortality.

There are many commercially available compounds in common usage for the control of ectoparasites. For livestock animals these include amitraz; fluazuron; synthetic pyrethroids, for example permethrin; macrocyclic lactones, for example ivermectin; and organophosphates. For companion animals these include fipronil; synthetic pyrethroids; and GABA-gated chloride channel inhibitors, for example fluralaner. Despite the wide range of products on the market, there remains a need for alternative compounds which are effective in the control of ectoparasites.

WO 2006/004924 discloses a series of heteroaryl-imidazole compounds which are modulators of the CXCR3 receptor. Modulators of the CXCR3 receptor are useful in the treatment and prevention of certain inflammatory and immunoregulatory disorders and diseases.

The present invention provides novel heteroaryl-1,2,4-triazole and heteroaryl-tetrazole compounds which are useful in the control of pests, especially the control of ectoparasites on animals.

The present invention provides compounds of Formula I:

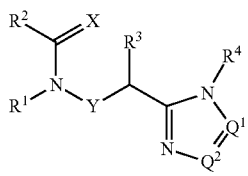

wherein:
X is O or S;
$Q^1$ and $Q^2$ are independently $CR^5$ or N, provided at least one of $Q^1$ and $Q^2$ is N;
Y is a direct bond or $CH_2$;
$R^1$ is H; $C_1$-$C_6$alkyl optionally substituted with one substituent selected from: CN, $CONH_2$, COOH, $NO_2$ and —Si$(CH_3)_3$; $C_1$-$C_6$haloalkyl; $C_2$-$C_6$alkenyl; $C_2$-$C_6$haloalkenyl; $C_2$-$C_6$alkynyl; $C_2$-$C_6$haloalkynyl; $C_3$-$C_4$cycloalkyl-$C_1$-$C_2$alkyl- wherein the $C_3$-$C_4$cycloalkyl is optionally substituted with 1 or 2 halo atoms; oxetart-3-yl-$CH_2$—; or benzyl optionally substituted with halo or $C_1$-$C_3$haloalkyl;

$R^2$ is phenyl, pyridine, pyrimidine, pyrazine or pyridazine, wherein the phenyl, pyridine, pyrimidine, pyrazine or pyridazine is optionally substituted with one to three substituents, provided the substituent(s) are not on either carbon adjacent to the carbon bonded to the

group, each independently selected from: $C_1$-$C_3$alkyl, $C_1$-$C_3$haloalkyl, $C_1$-$C_3$thiohaloalkyl, $C_1$-$C_3$alkoxy, $C_1$-$C_3$haloalkoxy, halo, $NO_2$, $SF_5$, CN, $CONH_2$, COOH and $C(S)NH_2$;
$R^3$ is $C_1$-$C_3$alkyl or $C_1$-$C_3$haloalkyl;
$R^4$ is pyridine, pyrimidine, pyrazine or pyridazine, wherein the pyridine, pyrimidine, pyrazine or pyridazine is optionally substituted with one substituent selected from: $C_1$-$C_3$alkyl, $C_1$-$C_3$haloalkyl, $C_1$-$C_3$alkoxy, $C_3$-$C_4$cycloalkyl, halo or hydroxy;
$R^5$ is H, $C_1$-$C_3$alkyl, $C_1$-$C_3$haloalkyl, $C_3$-$C_4$cycloalkyl, $C_1$-$C_6$alkoxy, $C_1$-$C_3$alkoxyC(O)— or ($C_1$-$C_3$alkoxy)$_2$CH—;
or a salt thereof.

In an alternative embodiment the present invention provides compounds of Formula I:

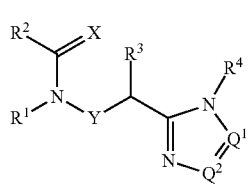

wherein:
X is O or S,
$Q^1$ and $Q^2$ are independently $CR^5$ or N, provided at least one of $Q^1$ and $Q^2$ is N;
Y is a direct bond or $CH_2$;
$R^1$ is H; $C_1$-$C_6$alkyl optionally substituted with one substituent selected from: CN, $CONH_2$, COOH and $NO_2$; $C_1$-$C_6$haloalkyl; $C_2$-$C_6$alkenyl; $C_2$-$C_6$haloalkenyl, $C_2$-$C_6$alkynyl; $C_2$-$C_6$haloalkynyl; $C_3$-$C_4$cycloalkyl-$C_1$-$C_2$alkyl- wherein the $C_3$-$C_4$cycloalkyl is optionally substituted with 1 or 2 halo atoms; oxetan-3-yl-$CH_2$—; or benzyl optionally substituted with halo or $C_1$-$C_3$haloalkyl;

$R^2$ is phenyl, pyridine, pyrimidine, pyrazine or pyridazine, wherein the phenyl, pyridine, pyrimidine, pyrazine or pyridazine is optionally substituted with one to three substituents, provided the substituent(s) are not on either carbon adjacent to the carbon bonded to the

group, each independently selected from: $C_1$-$C_3$alkyl, $C_1$-$C_3$haloalkyl, $C_1$-$C_3$thiohaloalkyl, $C_1$-$C_3$alkoxy, $C_1$-$C_3$haloalkoxy, halo, $NO_2$, $SF_5$, CN, $CONH_2$ and COOH;
$R^3$ is $C_1$-$C_3$alkyl or $C_1$-$C_3$haloalkyl;

$R^4$ is pyridine, pyrimidine, pyrazine or pyridazine, wherein the pyridine, pyrimidine, pyrazine or pyridazine is optionally substituted with one substituent selected from: $C_1$-$C_3$alkyl, $C_1$-$C_3$haloalkyl, $C_1$-$C_3$alkoxy, $C_3$-$C_4$cycloalkyl, halo or hydroxy;

$R^5$ is H, $C_1$-$C_3$alkyl, $C_1$-$C_3$haloalkyl, $C_3$-$C_4$cycloalkyl or $C_1$-$C_3$alkoxy, or a salt thereof.

The present invention also provides a formulation comprising a compound of the invention, or a salt thereof, and at least one acceptable carrier.

The present invention provides a compound of the invention, or a salt thereof, for use in therapy. The present invention provides a compound of the invention, or a salt thereof, for use in controlling parasites in or on an animal. The present invention further provides a compound of the invention, or a salt thereof, for use in controlling ectoparasites on an animal. The present invention further provides a compound of the invention, or a salt thereof, for use in preventing and/or treating diseases transmitted by ectoparasites.

The present invention provides the use of a compound of the invention, or a salt thereof, for the manufacture of a medicament for controlling parasites in or on an animal. The present invention further provides the use of a compound of the invention, or a salt thereof, for the manufacture of a medicament for controlling ectoparasites on an animal. The present invention further provides the use of a compound of the invention, or a salt thereof, for the manufacture of a medicament for preventing and/or treating diseases transmitted by ectoparasites.

The present invention provides the use of a compound of the invention, or a salt thereof, in controlling parasites in or on an animal. The present invention further provides the use of a compound of the invention, or a salt thereof, in controlling ectoparasites on an animal.

The present invention provides a method of controlling parasites in or on an animal in need thereof comprising administering an effective amount of a compound of the invention, or a salt thereof. The present invention further provides a method of controlling ectoparasites on an animal in need thereof comprising administering an effective amount of a compound of the invention, or a salt thereof. The present invention further provides a method for preventing and/or treating diseases transmitted by ectoparasites comprising administering an effective amount of a compound of the invention, or a salt thereof, to an animal in need thereof.

The present invention additionally provides a method for controlling pests comprising contacting the pests or their environment with an effective amount of a compound of the invention, or a salt thereof.

As used herein, the term "$C_1$-$C_6$alkyl" refers to a straight or branched, monovalent saturated aliphatic chain of one to six carbon atoms, for example, methyl, ethyl, propyl, isopropyl, butyl, t-butyl, and the like.

Likewise, the term "$C_1$-$C_3$alkyl" includes methyl, ethyl, isopropyl, and the like.

As used herein, the term "$C_1$-$C_6$haloalkyl" refers to a $C_1$-$C_6$alkyl moiety substituted with one or more halogen atoms which may be the same or different. Examples include trifluoromethyl, 2-fluoroethyl, 3-fluoropropyl, 3,3,3-trifluoropropyl, 4-chlorobutyl, and the like.

Likewise, the term "$C_1$-$C_3$haloalkyl" includes trifluoromethyl, 2-fluoroethyl, 3-fluoropropyl, 3,3,3-trifluoropropyl, and the like.

As used herein the term "$C_1$-$C_3$thiohaloalkyl" refers to a $C_1$-$C_3$haloalkyl moiety linked through a sulfur atom.

As used herein, the term "$C_3$-$C_4$cycloalkyl" refers to cyclopropyl or cyclobutyl.

As used herein, the term "$C_3$-$C_4$cycloalkyl-$C_1$-$C_2$alkyl-" refers to a $C_3$-$C_4$cycloalkyl linked through a $C_1$-$C_2$alkyl chain.

As used herein, the term "$C_2$-$C_6$alkenyl" refers to a straight or branched alkenyl chain having form two to six carbon atoms and one double bond, for example, ethenyl, prop-1-enyl, but-2-enyl, and the like.

As used herein, the term "$C_2$-$C_6$haloalkenyl" refers to a $C_2$-$C_6$alkenyl moiety substituted with one or more halo atoms which may be the same or different.

As used herein, the term "$C_2$-$C_6$alkynyl" refers to a straight or branched alkynyl chain having from two to six carbon atoms and one triple bond, for example, ethynyl, prop-2-ynyl, but-3-ynyl, and the like.

As used herein, the term "$C_2$-$C_6$haloalkynyl" refers to a $C_2$-$C_6$alkynyl moiety substituted with one or more halo atoms which may be the same or different.

As used herein, the term "halo" refers to a chlorine, bromine, iodine or fluorine atom.

As used herein, the term "$C_1$-$C_3$alkoxy" refers to a straight or branched alkyl chain having from 1 to 3 carbon atoms attached to an oxygen atom, for example, ethoxy, propoxy, tert-butoxy, and the like.

As used herein, the term "$C_1$-$C_3$haloalkoxy" refers to a $C_1$-$C_3$alkoxy moiety substituted with one or more halogen atoms which may be the same or different. Examples include trifluoromethoxy, 2-fluoroethoxy, 3-fluoropropoxy, 3,3,3-trifluoropropoxy, 4-chlorobutoxy, and the like.

As used herein, the term "controlling" refers to reducing the number of pests or parasites, eliminating pests or parasites and/or preventing further pest or parasite infestation.

As used herein, the term "treating" refers to restraining, slowing, stopping or reversing the progression or severity of an existing symptom or disease.

As used herein, the term "preventing" refers to the avoidance of a symptom or disease developing in the animal.

As used herein, the term "animal" may refer to a mammal and a non-mammal, such as a bird or fish. In the case of a mammal, it may be a human or non-human mammal. Non-human mammals include, but are not limited to, livestock animals and companion animals. Livestock animals include, but are not limited to, cattle, camellids, pigs, sheep, goats and horses. Companion animals include, but are not limited to, dogs, cats and rabbits.

As used herein, the term "pest" includes, but is not limited to, animal and plant pests. The term encompasses all stages in the life cycle of the pest.

A "parasite" is a pest which lives in or on the host animal and benefits by deriving nutrients at the host animal's expense. An "endoparasite" is a parasite which lives in the host animal. An "ectoparasite" is a parasite which lives on the host animal. Ectoparasites include, but are not limited to, acari, insects and crustaceans (e.g. sea lice). The Acari (or Acarina) sub-class comprises ticks and mites. Ticks include, but are not limited to, members of the following genera: *Rhipicephalus*, for example, *Rhipicaphalus (Boophilus) microplus* and *Rhipicephalus sanguineus*; *Amblyomma; Dermacentor; Haemaphysalis; Hyalomma; Ixodes; Rhipicentor; Margaropus; Argas; Otobius*; and *Ornithodoros*. Mites include, but are not limited to, members of the following genera *Chorioptes*, for example *Chorioptes bovis; Psoroptes*, for example *Psoroptes ovis; Cheyletiella; Dermanyssus*; for example *Dermanyssus gallinae; Ortnithonyssus; Demodex*, for example *Demodex canis; Sarcoptes*, for example *Sarcoptes scabiei*; and *Psorergates*. Insects include, but are not limited to, members of the orders: Siphonaptera, Diptera, Phthiraptera. Lepidoptera, Coleoptera and Homoptera. Members of the Siphonaptera order include, but are not limited to, *Ctenocephalides felis* and *Ctenocephalides canis*. Members of the Diptera order include, but are not limited to, *Musca* spp; bot fly, for example *Gasterophilus intestinalis* and *Oestrus ovis*; biting flies; horse flies, for example *Haematopota* spp. and *Tabunus* spp.; *haematobia*, for example *haematobia irritans; Stomoxys; Lucilia*; midges; and mosquitoes. Members of the Phthiraptera class include, but are not limited to, blood sucking lice and chewing lice, for example *Bovicola Ovis* and *Bovicola Bovis*.

As used herein, the term "effective amount" refers to the amount or dose of the compound of the invention, or a salt thereof, which, upon single or multiple dose administration to the animal, provides the desired effect in or on the animal.

An effective amount can be readily determined by the attending diagnostician, as one skilled in the art, by the use of known techniques and by observing results obtained under analogous circumstances. In determining the effective amount a number of factors are considered by the attending diagnostician, including, but not limited to: the species of mammal; its size, age, and general health; the parasite to be controlled and the degree of infestation; the specific disease or disorder involved; the degree of or involvement or the severity of the disease or disorder; the response of the individual; the particular compound administered; the mode of administration; the bioavailability characteristics of the preparation administered; the dose regimen selected; the use of concomitant medication; and other relevant circumstances.

The compounds of the invention may be administered to the animal by any route which has the desired effect including, but not limited to topically, orally, parenterally and subcutaneously. Topical administration is preferred. Formulations suitable for topical administration include, for example, solutions, emulsions and suspensions and may take the form of a pour-on, spot-on, spray-on, spray race or dip. In the alternative, the compounds of the invention may be administered by means of an ear tag or collar.

Salt forms of the compounds of the invention include both pharmaceutically acceptable salts and veterinary acceptable salts. Pharmaceutically and veterinary acceptable salts and common methodology for preparing them are well known in the art. See, for example, Gould, P. L., "Salt selection for basic drugs," *International Journal of Pharmaceutics*, 33: 201-217 (1986); Bastin, R J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*. 66: 1-19, (1977). One skilled in the art of synthesis will appreciate that the compounds of the invention are readily converted to and may be isolated as a salt, such as a hydrochloride salt, using techniques and conditions well known to one of ordinary skill in the art. In addition, one skilled in the art of synthesis will appreciate that the compounds of the invention are readily converted to and may be isolated as the corresponding free base from the corresponding salt.

As one of ordinary skill in the art will appreciate, compounds of Formula I contain a stereogenic centre which is indicated with an asterisk in the structure below:

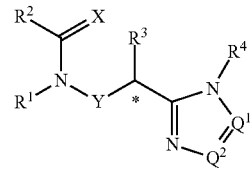

The present invention contemplates both racemates and individual enantiomers. Compounds having preferred stereochemistry are set out below.

Preferred compounds of Formula I, or salts thereof, include compounds having one or more of the following features:
a) Y is a direct bond;
b) X is O;
c) X is S;
d) $R^3$ is methyl;
e) $Q^1$ is N;
f) $Q^2$ is $CR^5$ and $R^5$ is H, $C_1$-$C_3$alkyl, $C_1$-$C_3$alkoxyC(O)—, or $(C_1$-$C_3$alkoxy$)_2$CH—;
g) $Q^2$ is $CR^5$ and $R^5$ is H, $C_1$-$C_3$alkyl, or $(C_1$-$C_3$alkoxy$)_2$CH—;
h) $Q^2$ is $CR^5$ and $R^5$ is H or $C_1$-$C_3$alkyl;
i) $Q^2$ is $CR^5$ and $R^5$ is H, methyl or $(CH_3CH_2O)_2$CH—;
j) $Q^2$ is $CR^5$ and $R^5$ is H or methyl;
k) $Q^2$ is $CR^5$ and $R^5$ is H;
l) $Q^1$ is N, $Q^2$ is $CR^5$ and $R^5$ is H, methyl or $(CH_3CH_2O)_2$CH—;
m) $Q^1$ is N, $Q^2$ is $CR^5$ and $R^5$ is H or methyl;
n) $R^4$ is a 2-pyridine; or 2-pyrimidine optionally substituted with $C_1$-$C_3$alkoxy or halo;
o) $R^4$ is a 2-pyridine; or 2-pyrimidine optionally substituted with $C_1$-$C_3$alkoxy;
p) $R^4$ is 2-pyridine or 2-pyrimidine;
q) $R^4$ is 2-pyrimidine;
r) $R^1$ is H; $C_1$-$C_6$haloalkyl; $C_1$-$C_6$alkyl optionally substituted with CN or $Si(CH_3)_3$; $C_3$-$C_6$alkynyl; $C_3$-$C_4$cycloalkyl-$C_1$-$C_2$alkyl wherein the $C_3$-$C_4$cycloalkyl is optionally substituted with 1 or 2 halo atoms; oxetan-3-yl-$CH_2$—; or benzyl optionally substituted with halo;
s) $R^1$ is H; $C_1$-$C_6$haloalkyl; $C_1$-$C_6$alkyl optionally substituted with CN or $Si(CH_3)_3$; $C_3$-$C_6$alkynyl; or $C_3$-$C_4$cycloalkyl-$C_1$-$C_2$alkyl- wherein the $C_3$-$C_4$cycloalkyl is optionally substituted with 1 or 2 halo atoms;
t) $R^1$ is $C_1$-$C_6$haloalkyl; $C_1$-$C_6$alkyl; $C_3$-$C_6$alkynyl; $C_3$-$C_4$cycloalkyl-$C_1$-$C_2$alkyl- wherein the $C_3$-$C_4$cycloalkyl is optionally substituted with 1 or 2 halo atoms;
u) $R^1$ is cyclopropyl-$CH_2$—, n-propyl, CH≡C—$CH_2$—, $CF_3CH_2CH_2$—, $FCH_2CH_2$—, $FCH_2CH_2CH_2$—, 2,2-difluorocyclopropyl-$CH_2$, 2,2-dichlorocyclopropyl-$CH_2$—, H, $CH_3$—, $(CH_3)_3SiCH_2$—, $CH_3CH_2$— or CN—$CH_2$—;
v) $R^1$ is cyclopropyl-$CH_2$—, n-propyl, CH≡C—$CH_2$—, $CF_3CH_2CH_2$—, $FCH_2CH_2$—, $FCH_2CH_2CH_2$—, 2,2-difluorocyclopropyl-$CH_2$— or 2,2-dichlorocyclopropyl-$CH_2$—;
w) $R^1$ is cyclopropyl-$CH_2$—, n-propyl, CH≡C—$CH_2$—, $CF_3CH_2CH_2$—, $FCH_2CH_2$—, $FCH_2CH_2CH_2$—, 2,2-difluorocyclopropyl-$CH_2$—, H, $CH_3$, $(CH_3)_3SiCH_2$— or $CH_3CH_2$—;
x) $R^1$ is cyclopropyl-$CH_2$—, n-propyl, CH≡C—$CH_2$—, $CF_3CH_2CH_2$—, $FCH_2CH_2$—, $FCH_2CH_2CH_2$—, or 2,2-difluorocyclopropyl-$CH_2$—;
x) $R^1$ is cyclopropyl-$CH_2$—, n-propyl, CH≡C—$CH_2$—, $CF_3CH_2CH_2$—, $FCH_2CH_2$— or $FCH_2CH_2CH_2$—;
y) $R^1$ is CH≡C—$CH_2$—, cyclopropyl-$CH_2$—, H or $CH_3$;

z) $R^1$ is CH≡C—CH$_2$— or cyclopropyl-CH$_2$—;

aa) $R^1$ is cyclopropyl-CH$_2$—;

bb) $R^2$ is phenyl, 3-pyridine or 4-pyridine substituted with one or two substituents selected from: $C_1$-$C_3$haloalkyl, $C_1$-$C_3$haloalkoxy, halo. CN or C(S)NH$_2$, provided the substituent(s) are not on either carbon adjacent to the carbon bonded to the

group;

cc) $R^2$ is phenyl, 3-pyridine or 4-pyridine substituted with one or two substituents selected from: $C_1$-$C_3$haloalkyl, $C_1$-$C_3$haloalkoxy, halo or CN, provided the substituent(s) are not on either carbon adjacent to the carbon bonded to the

group;

dd) $R^2$ is phenyl or 3-pyridine substituted with one or two substituents selected from: $C_1$-$C_3$haloalkyl, $C_1$-$C_3$haloalkoxy, halo or CN, provided the substituent(s) are not on either carbon adjacent to the carbon bonded to the

group;

ee) $R^1$ is 3,5-bis(trifluoromethyl)phenyl, 3,5-dichlorophenyl, 3-trifluoromethoxyphenyl, 3-chloro-5-trifluoromethylphenyl, 3-cyanophenyl, 3-chloro-5-trifluoromethoxyphenyl, 5-trifluoromethylpyridin-3-yl, 3-bromo-5-trifluoromethylphenyl, 3-cyano-5-trifluoromethyl-phenyl or 2,6-bis(trifluoromethyl)pyridin-4-yl;

ff) $R^1$ is 3,5-bis(trifluoromethyl)phenyl, 3,5-dichlorophenyl, 3-trifluoromethoxyphenyl, 3-chloro-5-trifluoromethylphenyl, 3-cyanophenyl, 3-chloro-5-trifluoromethoxyphenyl, 5-trifluoromethylpyridin-3-yl, 3-bromo-5-trifluoromethylphenyl or 3-cyano-5-trifluoromethyl-phenyl;

gg) $R^2$ is 3,5-bis(trifluoromethyl)phenyl, 3,5-dichlorophenyl, 3-trifluoromethoxyphenyl, 3-chloro-5-trifluoromethylphenyl, 3-cyanophenyl, 3-chloro-5-trifluoromethoxyphenyl, or 5-trifluoromethylpyridin-3-yl;

hh) $R^1$ is 3,5-bis(trifluoromethyl)phenyl, 3-chloro-5-trifluoromethylphenyl, 3-cyanophenyl, 3-chloro-5-trifluoromethoxyphenyl, 5-trifluoromethylpyridin-3-yl or 3-cyano-5-trifluoromethylphenyl;

ii) $R^2$ is 3,5-bis(trifluoromethyl)phenyl, 3-chloro-5-trifluoromethylphenyl, 3-chloro-5-trifluoromethoxyphenyl or 5-trifluoromethylpyridin-3-yl;

jj) $R^2$ is 3,5-bis(trifluoromethyl)phenyl.

Preferred compounds of the present invention are compounds of Formula II':

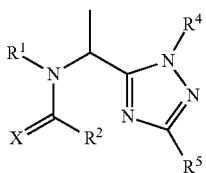

X is O or S:

$R^1$ is H; $C_1$-$C_6$haloalkyl; $C_1$-$C_6$alkyl optionally substituted with CN or —Si(CH$_3$)$_3$; $C_3$-$C_6$alkynyl; $C_3$-$C_4$cycloalkyl-$C_1$-$C_2$alkyl wherein the $C_3$-$C_4$cycloalkyl is optionally substituted with 1 or 2 halo atoms; oxetan-3-yl-CH$_2$—; or benzyl optionally substituted by halo;

$R^2$ is phenyl, 3-pyridine or 4-pyridine substituted with one or two substituents selected from: $C_1$-$C_3$haloalkyl, $C_1$-$C_3$haloalkoxy, halo, CN or C(S)NH$_2$, provided the substituent(s) are not on either carbon adjacent to the carbon bonded to the

group:

$R^4$ is 2-pyridine; or 2-pyrimidine optionally substituted with $C_1$-$C_3$alkoxy or halo;

$R^5$ is H, $C_1$-$C_3$alkyl, $C_1$-$C_3$alkoxyC(O)— or ($C_1$-$C_3$alkoxy)$_2$CH—, or a salt thereof.

Preferred compounds of the present invention are compounds of Formula II:

wherein:

$R^1$ is $C_1$-$C_6$haloalkyl; $C_1$-$C_6$alkyl; $C_3$-$C_6$alkynyl; or $C_3$-$C_4$cycloalkyl-$C_1$-$C_2$alkyl wherein the $C_3$-$C_4$cycloalkyl is optionally substituted with 1 or 2 halo atoms:

$R^2$ is phenyl or 3-pyridine substituted with one or two substituents selected from $C_1$-$C_3$haloalkyl, $C_1$-$C_3$haloalkoxy, halo or CN, provided the substituent(s) are not on either carbon adjacent to the carbon bonded to the

group;

$R^4$ is 2-pyridine; or 2-pyrimidine optionally substituted with $C_1$-$C_3$alkoxy:

$R^5$ is H or $C_1$-$C_3$alkyl, or a salt thereof.

Particularly preferred compounds of the present invention are compounds of Formula II'a or IIa:

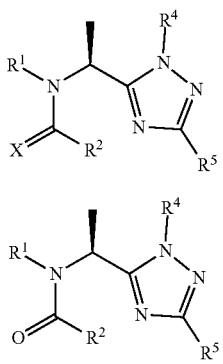

wherein X, R¹, R², R⁴ and R⁵ are as defined for Formula II' or Formula II respectively; or a salt thereof.

Preferred compounds of Formula I, II' and II'a, or salts thereof, include those in which R¹ is cyclopropyl-CH₂—, n-propyl, CH≡C—CH₂—, CF₃CH₂CH₂—, FCH₂CH₂—, FCH₂CH₂CH₂—, 2,2-difluorocyclopropyl-CH₂—, 2,2-dichlorocyclopropyl-CH₂—, H, CH₃, (CH₃)₃SiCH₂—, CH₃CH₂—, or CN—CH₂—; R² is 3,5-bis(trifluoromethyl)phenyl, 3,5-dichlorophenyl, 3-trifluoromethoxyphenyl, 3-chloro-5-trifluoromethylphenyl, 3-cyanophenyl, 3-chloro-5-trifluoromethoxyphenyl, 5-trifluoromethylpyridin-3-yl, 3-bromo-5-trifluoromethylphenyl, 3-cyano-5-trifluoromethylphenyl or 2,6-bis(trifluoromethyl)pyridin-4-yl; R⁴ is 2-pyridine, or 2-pyrimidine optionally substituted with C₁-C₃alkoxy; and R⁵ is H, methyl or (CH₃CH₂O)₂CH—.

Preferred compounds of Formula I, II', II, II'a and IIa or salts thereof, include those in which R¹ is cyclopropyl-CH₂—, n-propyl, CH≡C—CH₂—, CF₃CH₂CH₂—, FCH₂CH₂—, FCH₂CH₂CH₂—, 2,2-difluorocyclopropyl-CH₂— or 2,2-dichlorocyclopropyl-CH₂—; R² is 3,5-bis(trifluoromethyl)phenyl, 3,5-dichlorophenyl, 3-trifluoromethoxyphenyl, 3-chloro-5-trifluoromethylphenyl, 3-cyanophenyl, 3-chloro-5-trifluoromethoxyphenyl, or 5-trifluoromethylpyridin-3-yl; R⁴ is 2-pyridine, or 2-pyrimidine optionally substituted by C₁-C₃alkoxy and R⁵ is H or methyl.

Further preferred compounds of Formula I, II', II, II'a and IIa, or salts thereof, include those in which R¹ is cyclopropyl-CH₂—, n-propyl, CH≡C—CH₂—, CF₃CH₂CH₂—, FCH₂CH₂—, FCH₂CH₂CH₂— or 2,2-difluorocyclopropyl-CH₂—; R² is 3,5-bis(trifluoromethyl)phenyl, 3,5-dichlorophenyl, 3-trifluoromethoxyphenyl, 3-chloro-5-trifluoromethylphenyl, 3-cyanomethyl, 3-chloro-5-trifluoromethoxyphenyl, or 5-trifluoromethylpyridin-3-yl; R⁴ is 2-pyridine, or 2-pyrimidine optionally substituted with C₁-C₃alkoxy; and R⁵ is H or methyl.

Further preferred compounds of Formula I, II', II, II'a and IIa or salts thereof, include those in which R¹ is cyclopropyl-CH₂—, n-propyl, CH≡C—CH₂—, CF₃CH₂CH₂—, FCH₂CH₂— or FCH₂CH₂CH₂—; R² is 3,5-bis(trifluoromethyl)phenyl, 3-chloro-5-trifluoromethylphenyl, 3-chloro-5-trifluoromethoxyphenyl or 5-trifluoromethylpyridin-3-yl; R⁴ is 2-pyridine or 2-pyrimidine; and R⁵ is H or methyl.

Further preferred compounds of Formula I, II', and II'a, or salts thereof, include those in which R¹ is CH≡C—CH₂—, cyclopropyl-CH₂—, H or CH₃; R² is 3,5-bis(trifluoromethyl)phenyl, 3-chloro-5-trifluoromethylphenyl, 3-cyanophenyl, 3-chloro-5-trifluoromethoxyphenyl, 5-trifluoromethylpyridin-3-yl or 3-cyano-5-trifluoromethylphenyl; R⁴ is 2-pyridine, or 2-pyrimidine; and R⁵ is H, methyl or (CH₃CH₂O)₂CH—.

A preferred compound of the present invention is N-(cyclopropylmethyl)-N-[1-(2-pyrimidin-2-yl-1,2,4-triazol-3-yl)ethyl]-3,5-bis(trifluoromethyl)benzamide, or a salt thereof. An especially preferred compound is N-(cyclopropylmethyl)-N-[(1S)-1-(2-pyrimidin-2-yl-, 2,4-triazol-3-yl)ethyl]-3,5-bis(trifluoromethyl)benzamide, or a salt thereof. Another preferred compound of the present invention is N-prop-2-ynyl-N-[1-(2-pyrimidin-2-yl-1,2,4-triazol-3-yl)ethyl]-3,5-bis(trifluoromethyl)benzamide, or a salt thereof. An especially preferred compound is N-prop-2-ynyl-N-[(1S)-1-(2-pyrimidin-2-yl-1,24-triazol-3-yl)ethyl]-3,5-bis(trifluoromethyl)benzamide, or a salt thereof. Another preferred compound of the present invention is N-methyl-N-[1-(2-pyrimidin-2-yl-1,2,4-triazol-3-yl)ethyl]-3,5-bis(trifluoromethyl)benzamide, or a salt thereof. An especially preferred compound is N-methyl-N-[(1S)-1-(2-pyrimidin-2-yl-1,2,4-triazol-3-yl)ethyl]-3,5-bis(trifluoromethyl)benzamide, or a salt thereof.

The compounds of the present invention may be used for controlling parasites. In particular, they are useful for controlling ectoparasites on an animal. In one embodiment, the compounds of the present invention may be used for controlling ticks on cattle. In an alternative embodiment, the compounds of the present invention may be used for controlling ticks on sheep. In another alternative embodiment, the compounds of the present invention may be used for controlling lice on sheep. In another alternative embodiment, the compounds of the present invention may be used for controlling ticks on a dog or a cat. In another alternative embodiment, the compounds of the present invention may be used for controlling fleas on a dog or a cat. In another alternative embodiment, the compounds of the present invention may be used for controlling lice on a dog or a cat.

The compounds of the present invention may also be used for preventing and/or treating diseases, for example protozoan, bacterial and viral diseases, transmitted by ectoparasites. In particular, they may be used for the prevention and/or treatment of babesiosis, anaplasmosis and lyme disease.

The compounds of the present invention may be used alone or combination with one or more other compounds with are active against parasites or pests, including afoxolaner, fluralaner, lotilaner, surolaner, albendazole, cambendazole, fenbendazole, flubendazole, mebendazole, oxfendazole, parabendazole, tiabendazole, triclabendazole, amitraz, demiditraz, clorsulon, closantel, oxyclonazide, rafoxanide, cyphenothrin, flumethrin, permethrin, cyromazine, derquantel, diamphenetide, dicyclanil, dinotefuran, imidacloprid, nitenpyram, thiamethoxam, abamectin, doramectin, emamectin, eprinomectin, ivermectin, moxidectin, selamectin, milbemycin oxime, emodepside, epsiprantel, fipronil, fluazuron, fluhexafon, indoxacarb, levamisol, lufenuron, metaflumizone, methoprene, monepantel, morantel, niclosamide, nitroscanate, nitroxynil, novaluron, oxantel, praziquantel, pyrantel, pyriprole, pyriproxyfen, sisapronil, spinosad, spinetoram and triflumezopyrim.

The compounds of Formula I, II', II, II'a and IIa can be prepared by one of ordinary skill in the art following art recognized techniques and procedures. More specifically, compounds of Formula I, II', II, II'a and IIa can be prepared as set forth in the schemes, methods, and examples set forth below. It will be recognized by one of skill in the art that the individual steps in the following schemes may be varied to provide the compounds of Formula I, II', II, II'a and IIa. The reagents and starting materials are readily available to one of ordinary skill in the art. All substituents, unless otherwise specified, are as previously defined.

Certain stereogenic centers have been left unspecified and certain substituents have been eliminated in the following schemes for the sake of clarity and are not intended to limit the teaching of the schemes in any way. Furthermore, individual enantiomers may be separated or resolved by one of ordinary skill in the art at any convenient point in the synthesis of compounds of the invention or pharmaceutically acceptable salts there by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen. "*Stereochemistry of Organic Compounds*", Wiley-Interscience, 1994).

ABBREVIATIONS AND SYMBOLS

AcOH: acetic acid
aq.: aqueous
br: broad
d: doublet
DCC: N,N'-dicyclohexylcarbodiimide
DIPEA: diisopropylethylamine
DMF: N,N-Dimethylformamide
DMSO: dimethylsulfoxide
ee: enantiomeric excess
eq.: equivalent
ES: electrospray ionization
EtOAc: ethyl acetate
HATU: 1-[Bis(dimethylamino)methylene]-1H-1,2,3-triazolo[4,5-b]pyridinium 3-oxid hexafluorophosphate
HOBt: 1-Hydroxybenzotriazole hydrate
HPLC: high performance liquid chromatography
iPrOH: isopropanol
J: coupling constant
LCMS: liquid chromatography-mass spectrometry
m/z: mass-to-charge ratio
M: molarity
m: multiplet
MeOH: methanol
NMR: nuclear magnetic resonance
q: quartet
r.t.: room temperature
$R_t$: retention time
s: singlet
sat.: saturated
T: temperature
t: triplet
T3P: Propylphosphonic anhydride
THF: tetrahydrofuran
wt.: weight
δ: chemical shift
λ: wavelength Compounds of formula I' may be prepared as illustrated in the following scheme where $R^1$, $R^2$, $R^3$, $R^4$, $Q^1$, $Q^2$ and Y are as previously defined.

SCHEME 1

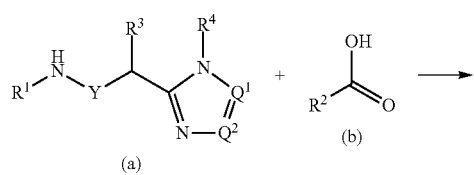

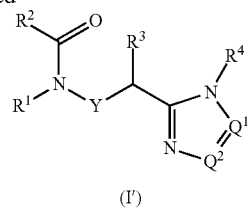

(I')

An azole compound of formula (a) is reacted with a carboxylic acid of formula (b) to form compounds of formula I. For example, a mixture of an azole of formula (a), a carboxylic acid of formula (b), a suitable coupling reagent, such as T3®, HATU, DCC or HOBt, a suitable base such as triethylamine or DIPEA, in a suitable solvent, such as ethyl acetate or DMF are mixed at temperatures ranging from around 0 to 100° C. to provide compounds of formula I which may then be isolated and, if necessary and desired, purified using techniques well known in the art, such as chromatography.

Carboxylic acids of formula (b) are commercially available or may be synthesized by methods known to the skilled artisan.

The requisite azole compounds of formula (a) may be prepared as illustrated in the following scheme, where $R^1$, $R^3$, $R^4$, $Q^1$, $Q^2$ and Y are as previously described and LG is a suitable leaving group.

SCHEME 2

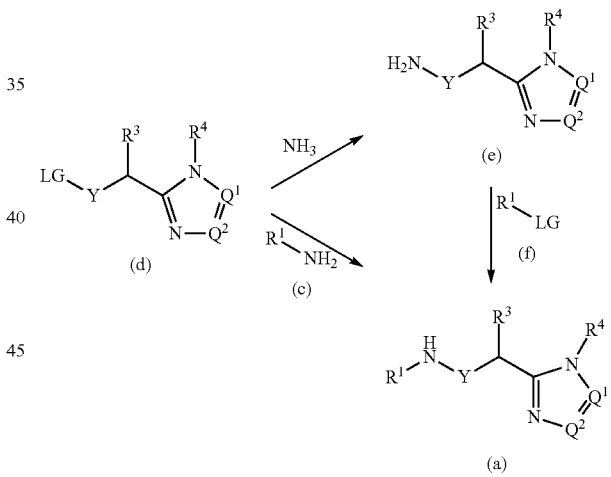

An amine of formula (c) is reacted with a substituted azole of formula (d) to form compounds of formula (a). For example, a mixture of an azole of formula (d), an amine of formula (c), a suitable base, such as $K_2CO_3$, NaH or DIPEA in a suitable solvent, such as acetonitrile or DMF are mixed at temperatures ranging from around 20 to 120° C. to provide compounds of formula (a) which may then be isolated and, if necessary and desired, purified using techniques well known in the art, such as chromatography.

Alternatively, a substituted azole of formula (d) is reacted with ammonia to form compounds of formula (e). For example, a solution of ammonia in a suitable solvent, such as methanol, and a substituted azole of formula (d) are mixed in a sealed tube at temperatures ranging from around 0 to 25° C. to provide compounds of formula (e) which may then be isolated and, if necessary and desired, purified using techniques well known in the art, such as trituration.

A substituted azole of formula (e), a compound of formula (f), a suitable base, such as K$_2$CO$_3$ or DIPEA in a suitable solvent, such as acetonitrile or DMF are mixed at temperatures ranging from around 20 to 120° C. to provide compounds of formula (a) which may then be isolated and, if necessary and desired, purified using techniques well known in the art, such as chromatography.

Amines of formula (c) and compounds of formula (f) are commercially available or may be synthesized by methods known to the skilled artisan.

The requisite azole compounds of formula (d) may be prepared as illustrated in the following scheme, where R$^3$, R$^4$, R$^5$, Q$^1$, Q$^2$ and Y are as previously described, LG is a suitable leaving group.

hydrazines of formula (j) are commercially available or may be synthesized by methods known to the skilled artisan.

Compounds of formula I" may be prepared as illustrated in the following scheme where R$^1$, R$^2$, R$^3$, R$^4$, R$^5$ and Y are as previously defined.

SCHEME 4

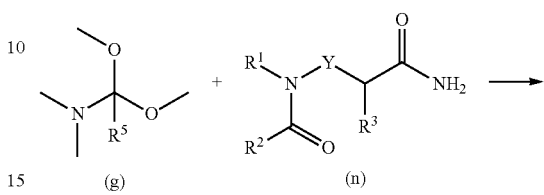

SCHEME 3

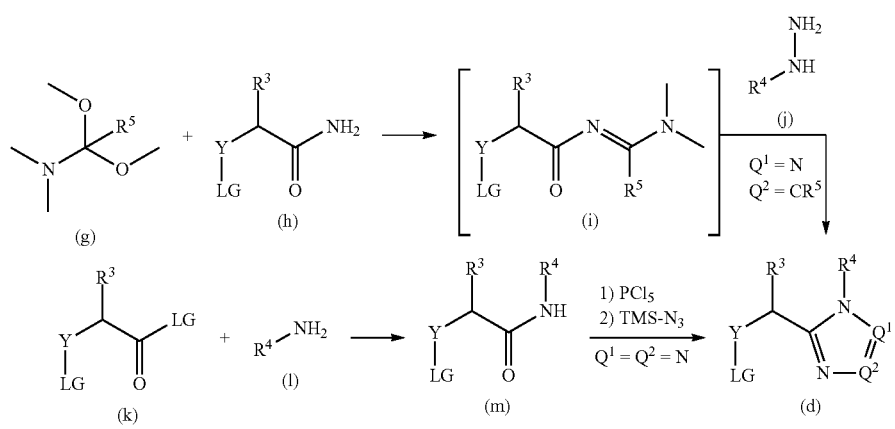

An amide of formula (h) is reacted with an N,N-dimethylamide dimethyl acetal (g) to form compounds of formula (i) which are subsequently reacted with hydrazines (j) under acidic conditions to form compounds of formula (d). For example, a compound of formula (h) and an N,N-dimethylamide dimethyl acetal of formula (g) are reacted in a suitable solvent, such as CH$_2$Cl$_2$ at reflux to provide compounds of formula (i). Upon removal of the solvent, compounds of formula (i) are reacted with a substituted hydrazine (j) in a suitable solvent such as 1,4-dioxane, acetic acid or a mixture of such solvents at temperatures ranging from around 20 to 100° C. to provide compounds of formula (d) which may then be isolated and, if necessary and desired, purified using techniques well known in the art, such as chromatography.

Alternatively, a carboxylic acid derivative of formula (k) is reacted with an amine of formula (l) and a suitable base, such as triethylamine or DIPEA, in a suitable solvent, such as toluene, at temperatures ranging from around 0 to 120° C. The resulting compounds (m) may then be isolated and, if necessary and desired, purified using techniques well known in the art, such as chromatography. The resulting amides of formula (m) and phosphorus pentachloride are reacted in a suitable solvent, such as CH$_2$Cl$_2$, at r.t. and then trimethylsilyl azide is added to the mixture at 0° C. and the mixture is stirred at r.t. to provide compounds of formula (d) which may then be isolated and, if necessary and desired, purified using techniques well known in the art, such as chromatography.

N,N-dimethylamide acetals of formula (g), amides of formula (h), carboxylic acid derivatives of formula (k) and -continued

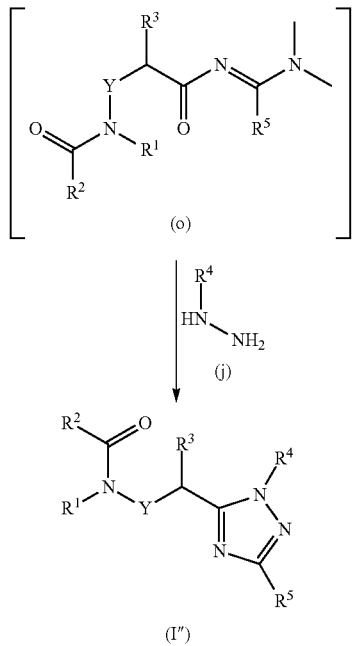

An amide of formula (n) is reacted with an N,N-dimethyamide dimethyl acetal of formula (g) to form compounds of formula (o) which are subsequently reacted with substituted hydrazines of formula (j) under acidic conditions to form compounds of formula I". For example, a compound of formula (n) and an N,N-dimethylamide dimethyl acetal of formula (g) are reacted in a suitable solvent, such as CH$_2$Cl$_2$ at reflux to provide compounds of formula (o). Upon removal of the solvent, compounds of formula (o) are reacted with a substituted hydrazine of formula (j) in a suitable solvent such as 1,4-dioxane, acetic acid or a mixture of such solvents at temperatures ranging from around 20 to 100° C. The resulting compounds of formula I" may then be isolated and, if necessary and desired, purified using techniques well known in the art, such as chromatography.

The requisite amides of formula (n) may be prepared as illustrated in the following scheme, where R$^1$, R$^2$, R$^3$, and Y are as previously described.

then reacted with a carboxylic acid of formula (b), a suitable coupling reagent, such as T3P®, a suitable base such as DIPEA, in a suitable solvent, such as ethyl acetate at about 90° C. to provide amido esters of formula (t) which may then be isolated and, if necessary and desired, purified using techniques well known in the art, such as chromatography. The resulting amido esters of formula (t) are reacted with magnesium nitride in a suitable solvent, such as MeOH at about 80° C. in a sealed tube to provide compounds of formula (n) which may then be isolated and, if necessary and desired, purified using techniques well known in the art, such as chromatography or extraction.

Compounds of formula (b) and (q) are commercially available. The requisite amino amide compounds of formula (p) are commercially available or may be prepared as illustrated in the following scheme, where R$^1$, R$^3$ and Y are as previously described and LG is a suitable leaving group.

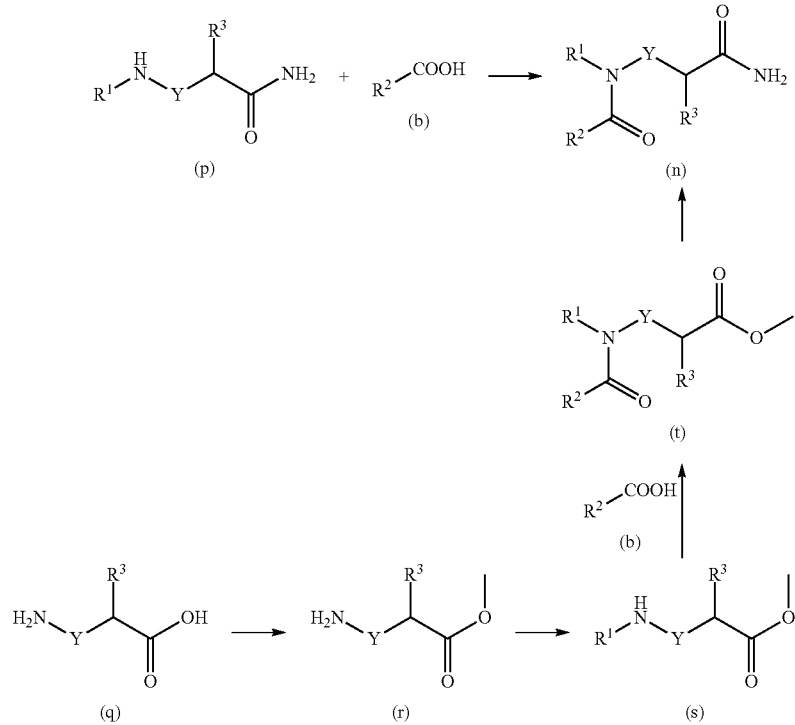

SCHEME 5

An amino amide of formula (p) is reacted with a carboxylic acid of formula (b) to form compounds of formula (n). For example, a mixture of an amino amide of formula (p), a carboxylic acid (b), a suitable coupling reagent, such as T3P®, HATU, DCC or HOBt, a suitable base such as triethylamine or DIPEA, in a suitable solvent, such as ethyl acetate or DMF are mixed at temperatures ranging from around 0 to 100° C. to provide compounds of formula (n) which may then be isolated and, if necessary and desired, purified using techniques well known in the art, such as chromatography.

Alternatively, an amino acid of formula (q) is reacted with thionyl chloride in a suitable solvent, such as MeOH, at r.t. to provide amino esters of formula (r). The resulting amino esters (r) are reacted with an aldehyde or a ketone, a suitable reducing agent, such as sodium triacetoxyborohydride, a dehydrating agent, such as Na$_2$SO$_4$, in a suitable solvent, such as acetic acid, at r.t. to provide compounds of formula (s). The resulting amino esters of formula (s) are Compounds of formula (c) and (h) are commercially available.

SCHEME 6

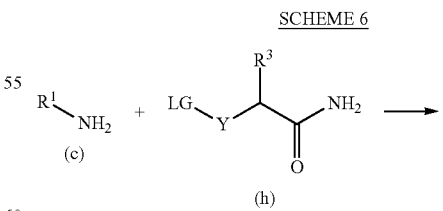

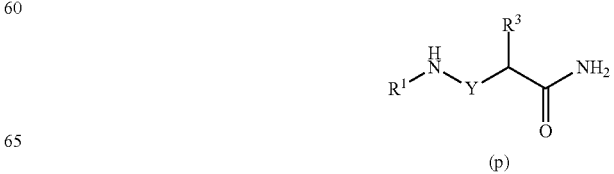

An amine of formula (c) is reacted with an amide of formula (h) to form compounds of formula (p). For example, a mixture of an amine of formula (c), an amide of formula (h), a suitable base, such as $K_2CO_3$ or DIPEA in a suitable solvent, such as acetonitrile or DMF are mixed at 25-80° C. to provide compounds of formula (p) which may then be isolated and, if necessary and desired, purified using techniques well known in the art, such as chromatography.

SCHEME 7

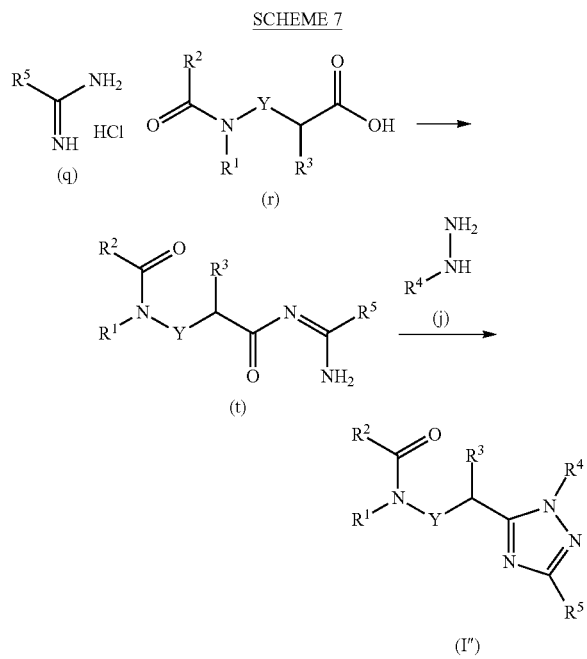

An amidine hydrochloride of formula (q) is reacted with an acid of formula (r) to form compounds of formula (t) which are subsequently reacted with substituted hydrazines of formula (j) under acidic conditions to form compounds of formula I".

PREPARATION 1

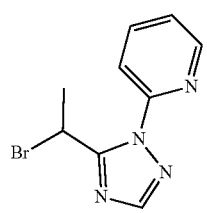

2-[5-(1-Bromoethyl)-1,2,4-triazol-1-yl]pyridine

Add N,N-dimethylamide dimethylacetal (3.00 mL) to a solution of 2-brompropanamide (2.28 g) in $CH_2Cl_2$ (50 mL) and stir at reflux for 1 h. Cool to r.t., concentrate under reduced pressure, dissolve the residue in 1,4-dioxane/AcOH (15 mL/15 mL), add 2-hydrazinopyridine (1.80 g) and stir at 90° C. for 2 h. Cool to r.t., concentrate under reduced pressure, partition the residue between $NaHCO_3$ (aq. sat.) and $CH_2Cl_2$. Separate the layers, extract the aqueous phase three times with $CH_2Cl_2$, dry the combined organic extracts over $MgSO_4$, filter, concentrate under reduced pressure and purify the residue by chromatography to provide 2-[5-(1-bromoethyl)-1,2,4-triazol-1-yl]pyridine (2.82 g, 74%). LCMS (method 2): $R_t$ 1.31 min, m/z (ES+)=253 $[M(^{79}Br)+H]^+$ and 255 $[M(^{81}Br)+H]^+$.

PREPARATION 2

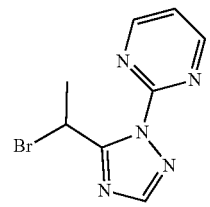

2-[5-(1-Bromoethyl)-1,2,4-triazol-1-yl]pyrimidine

Add N,N-dimethylamide dimethylacetal (3.3 mL) to a solution of 2-brompropanamide (2.5 g) in $CH_2Cl_2$ (30 mL) and stir at reflux for 1.5 h. Cool to r.t., concentrate under reduced pressure, dissolve the residue in 1,4-dioxane/AcOH (15 mL/15 mL), add 2-hydrazinopyrimidine (2.2 g) and stir at 50° C. overnight. Cool to r.t., concentrate under reduced pressure and partition the residue between water and EtOAc. Separate the layers, wash the organic phase with $NaHCO_3$ (aq. sat.), dry the organic phase over $MgSO_4$, filter, concentrate under reduced pressure and purify the residue by chromatography to provide 2-[5-(1-bromoethyl)-1,2,4-triazol-1-yl]pyrimidine (2.0 g, 48%). LCMS (method 4): $R_t$ 0.55 min, m/z (ES+)=254 $[M(^{79}Br)+H]^+$ and 256 $[M(^{81}Br)+H]^+$.

PREPARATION 3

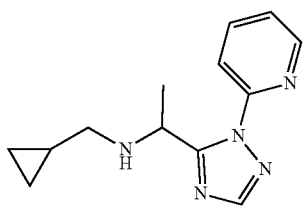 [SMILES: CC(NCC1CC1)c1ncnn1-c1ccccn1]

N-(Cyclopropylmethyl)-1-[2-(2-pyridyl)-1,2,4-triazol-3-yl]ethanamine

Add cyclopropanemethylamine (8.29 mL) to a suspension of 2-[5-(1-bromoethyl)-1,2,4-triazol-1-yl]pyridine (12.2 g) and $K_2CO_3$ (20.1 g) in DMF (100 mL) and stir the mixture at 80° C. for 2 h. Cool the mixture to r.t. and filter through Celite® washing with EtOAc. Concentrate the filtrate under reduced pressure and partition the residue between water and EtOAc. Separate the layers and extract the aqueous layer twice with EtOAc. Dry the combined organic extracts over $MgSO_4$, filter, concentrate under reduced pressure and purify the residue by chromatography to provide N-(cyclopropylmethyl)-1-[2-(2-pyridyl)-1,2,4-triazol-3-yl]ethanamine (11.4 g, 97%). $^1H$ NMR (400 MHz, $CDCl_3$) δ ppm −0.09-0.11 (2H, m), 0.36-0.47 (2H, m), 0.83-1.03 (1H, m), 1.59 (3H, d, J 6.6 Hz), 2.29 (1H, dd, J 11.9, 7.5 Hz), 2.50 (1H, dd, J 11.7, 6.6 Hz), 4.96 (1H, q, J 6.8 Hz), 7.31-7.38 (1H, m), 7.90-7.93 (2H, m), 7.97 (1H, s), 8.52 (1H, dt, J 4.7, 1.3 Hz).

The compounds of Preparations 4-19 set forth in table 1 may be prepared essentially as described in Preparation 3.

TABLE 1

| Prep | Structure | Compound | Analytical data | Remarks |
|---|---|---|---|---|
| 4 | 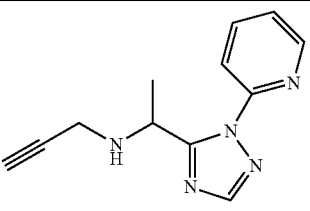 | N-[1-[2-(2-Pyridyl)-1,2,4-triazol-3-yl]ethyl]prop-2-yn-1-amine | $^1$H NMR (400 MHz, CDCl$_3$) δ ppm 1.60 (3H, d, J 6.8 Hz), 2.07 (1H, d, J 4.9 Hz), 3.07 (1H, s), 3.38 (1H, dd, J 16.7, 2.5 Hz), 3.49 (1H, dd, J 16.8, 2.5 Hz), 5.03 (1H, q, J 6.8 Hz), 7.29-7.40 (1H, m), 7.93 (2H, dd, J 3.7, 1.2 Hz), 7.99 (1H, s), 8.54 (1H, dt, J 4.9, 1.4 Hz) | — |
| 5 | 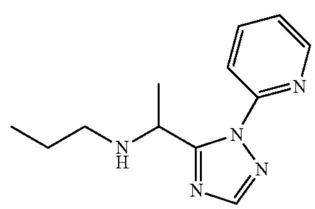 [SMILES: CCCNC(C)c1ncnn1-c1ccccn1] | N-[1-[2-(2-Pyridyl)-1,2,4-triazol-3-yl]ethyl]propan-1-amine | $^1$H NMR (400 MHz, CDCl$_3$) δ ppm 0.86 (3H, t, J 7.4 Hz), 1.42-1.54 (2H, m), 1.56 (3H, d, J 6.9 Hz), 2.42 (1H, ddd, J 11.0, 8.1, 6.3 Hz), 2.50 (1H, ddd, J 11.0, 8.1, 6.8 Hz), 2.68 (1H, s), 4.84-4.98 (1H, m), 7.34 (1H, td, J 4.9, 3.6 Hz), 7.87-7.95 (2H, m), 7.99 (1H, d, J 0.5 Hz), 8.48-8.55 (1H, m) | — |
| 6 | 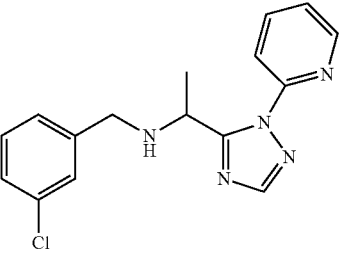 [SMILES: CC(NCc1cccc(Cl)c1)c1ncnn1-c1ccccn1] | N-[(3-Chlorophenyl)methyl]-1-[2-(2-pyridyl)-1,2,4-triazol-3-yl]ethanamine | LCMS: (method 1) R$_t$ 1.70 min, m/z (ES+) 314 [M + H]$^+$ | Reaction time:20 h |

TABLE 1-continued

| Prep | Structure | Compound | Analytical data | Remarks |
|---|---|---|---|---|
| 7 | 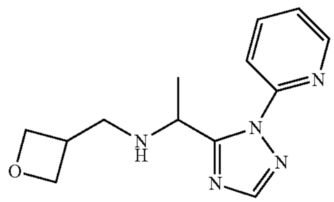 [SMILES: CC(NCC1COC1)c1ncnn1-c1ccccn1] | N-(Oxetan-3-ylmethyl)-1-[2-(2-pyridyl)-1,2,4-triazol-3-yl]ethanamine | LCMS: (method 7) $R_t$ 1.40 min, m/z (ES+) 260 [M + H]$^+$ | Reaction time:16 h; T = r.t. |
| 8 | 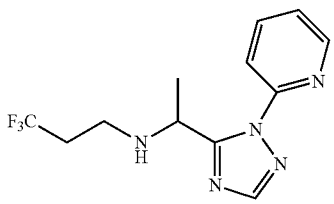 [SMILES: CC(NCCC(F)(F)F)c1ncnn1-c1ccccn1] | 3,3,3-Trifluoro-N-[1-[2-(2-pyridyl)-1,2,4-triazol-3-yl]ethyl]propan-1-amine | LCMS: (method 7) $R_t$ 1.59 min, m/z (ES+) 286 [M + H]$^+$ | Additional 1.0 eq. of DIPEA; Reaction time:18 h; T = 50° C. |
| 9 | 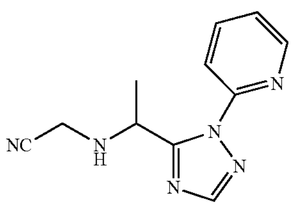 [SMILES: CC(NCC#N)c1ncnn1-c1ccccn1] | 2-[1-[2-(2-Pyridyl)-1,2,4-triazol-3-yl]ethylamino]acetonitrile | LCMS: (method 7) $R_t$ 1.65 min, m/z (ES+) 229 [M + H]$^+$ | DIPEA used in same amount as solvent in place of $K_2CO_3$; Reaction time: 18 h; T = r.t. |
| 10 | 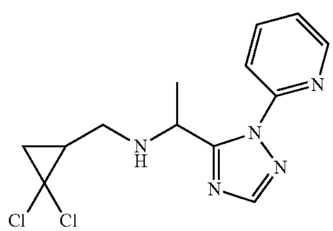 [SMILES: CC(NCC1CC1(Cl)Cl)c1ncnn1-c1ccccn1] | N-[(2,2-Dichlorocyclopropyl)methyl]-1-[2-(2-pyridyl)-1,2,4-triazol-3-yl]ethanamine | LCMS: (method 7) $R_t$ 1.69 min, m/z (ES+) 312 [M + H]$^+$ | Amine used as limiting reagent; Reaction time:16 h; T = r.t. |
| 11 | 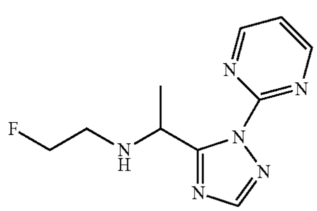 [SMILES: CC(NCCF)c1ncnn1-c1ncccn1] | N-(2-Fluoroethyl)-1-(2-pyrimidin-2-yl-1,2,4-triazol-3-yl)ethanamine | LCMS: (method 4) $R_t$ 0.31 min, m/z (ES+) 237 [M + H]$^+$ | Solvent: MeCN; T = reflux; Reaction time:16 h |
| 12 | 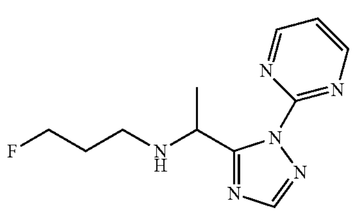 [SMILES: CC(NCCCF)c1ncnn1-c1ncccn1] | 3-Fluoro-N-[1-(2-pyrimidin-2-yl-1,2,4-triazol-3-yl)ethyl]propan-1-amine | LCMS: (method 5) $R_t$ 0.44 min, m/z (ES+) 251 [M + H]$^+$ | Solvent: MeCN; T = reflux; Reaction time:1 h |
| 13 | 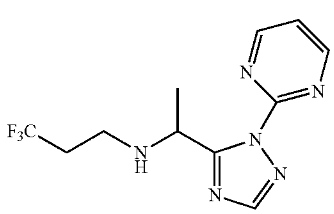 [SMILES: CC(NCCC(F)(F)F)c1ncnn1-c1ncccn1] | 3,3,3-Trifluoro-N-[1-(2-pyrimidin-2-yl-1,2,4-triazol-3-yl)ethyl]propan-1-amine | LCMS: (method 5) $R_t$ 0.33 min, m/z (ES+) 287 [M + H]$^+$ | Solvent: MeCN; T = reflux |

TABLE 1-continued

| Prep | Structure | Compound | Analytical data | Remarks |
|---|---|---|---|---|
| 14 | 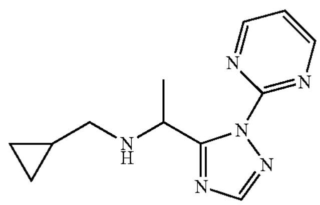 [SMILES: CC(NCC1CC1)c1ncnn1-c1ncccn1] | N-(Cyclopropylmethyl)-1-(2-pyrimidin-2-yl-1,2,4-triazol-3-yl)ethanamine | LCMS: (method 5) $R_t$ 0.34 min, m/z (ES+) 245 [M + H]$^+$ | Solvent: MeCN; T = reflux |
| 15 | 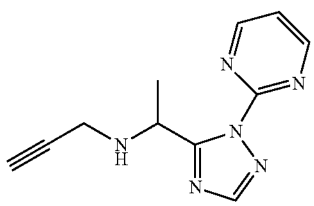 [SMILES: C#CCNC(C)c1ncnn1-c1ncccn1] | N-[1-(2-Pyrimidin-2-yl-1,2,4-triazol-3-yl)ethyl]prop-2-yn-1-amine | LCMS: (method 4) $R_t$ 0.31 min, m/z (ES+) 229 [M + H]$^+$ | Slovent: MeCN; Reaction time: 16 h; T = reflux |
| 16 | 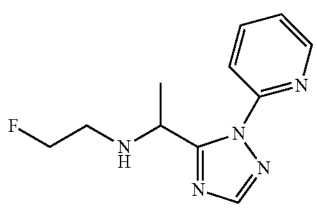 [SMILES: CC(NCCF)c1ncnn1-c1ccccn1] | N-(2-fluoroethyl)-1-[2-(2-pyridyl)-1,2,4-triazol-3-yl]ethanamine | LCMS: (method 8) $R_t$ 2.88 min, m/z (ES+) 236 [M + H]$^+$ | DIPEA (1.0 eq.) and NaH (2.0 eq.) used in place of $K_2CO_3$; Reaction time: 18 h; T = r.t. |
| 17 | 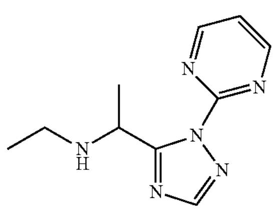 [SMILES: CCNC(C)c1ncnn1-c1ncccn1] | N-Ethyl-1-(2-pyrimidin-2-yl-1,2,4-triazol-3-yl)ethanamine | LCMS: (method 4) $R_t$ 0.39 min, m/z (ES+) 219 [M + H]$^+$ | Solvent: MeCN; Reaction time: 1 h 45 min; T = reflux |
| 18 | 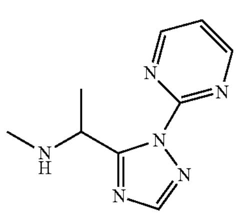 | N-Methyl-1-(2-pyrimidin-2-yl-1,2,4-triazol-3-yl)ethanamine | LCMS: (method 4) $R_t$ 0.29 min, m/z (ES+) 205 [M + H]$^+$ | Solvent: MeCN; Reaction time: 1 h; T = reflux |
| 19 | 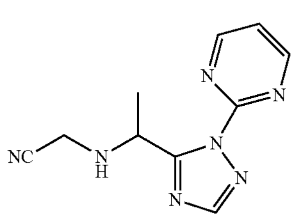 [SMILES: CC(NCC#N)c1ncnn1-c1ncccn1] | 2-[1-(2-Pyrimidin-2-yl-1,2,4-triazol-3-yl)ethylamino]acetonitrile | LCMS: (method 4) $R_t$ 0.37 min, m/z (ES+) 230 [M + H]$^+$ | Solvent: MeCN; Reaction time: 1 h; T = reflux |

PREPARATION 20

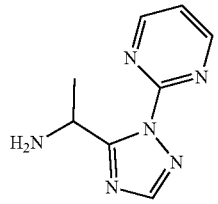

1-(2-Pyrimidin-2-yl-1,2,4-triazol-3-yl)ethanamine

Add ammonia (7 M in MeOH, 15 mL) to 2-[5-(1-bromoethyl)-1,2,4-triazol-1-yl]pyrimidine (1.14 g) and stir at r.t. for 24 h. Concentrate under reduced pressure to provide 1-(2-Pyrimidin-2-yl-1,2,4-triazol-3-yl)ethanamine (1.27 g, 61% purity, 90%). LCMS (method 5): $R_t$ 0.35 min, m/z (ES+)=191 [M+H]$^+$.

PREPARATION 21

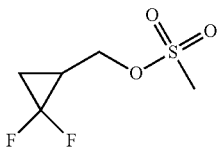

(2,2-Difluorocyclopropyl)methyl methanesulfonate

Add methanesulfonyl chloride (600 µL) to a mixture of triethylamine (1.4 mL) and (2,2-difluorocyclopropyl)methanol (677 mg) in CH$_2$Cl$_2$ (10 mL) at 0° C. and stir for 2 h. Warm to r.t. and stir overnight. Partition between water and CH$_2$Cl$_2$, separate the layers, extract the aqueous phase twice with CH$_2$Cl$_2$, dry the combined organic extracts over Na$_2$SO$_4$, filter and concentrate under reduced pressure to provide (2,2-difluorocyclopropyl)methyl methanesulfonate (1.17 g, 86%). $^1$H NMR (400 MHz, CDCl$_3$) δ ppm 1.27-1.35 (1 H, m), 1.63 (1 H, tdd, J 11.4, 8.2, 4.9 Hz), 1.97-2.14 (1 H, m), 3.04 (3 H, s), 4.18-4.38 (2 H, m).

PREPARATION 22

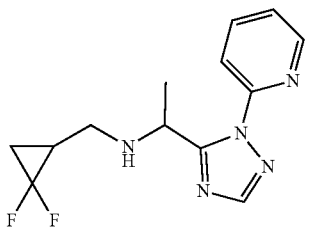 [SMILES: CC(NCC1CC1(F)F)c1ncnn1-c1ccccn1]

N-[(2,2-Difluorocyclopropyl)methyl]-1-[2-(2-pyridyl)-1,2,4-triazol-3-yl]ethanamine Add ammonia (sat. in MeOH, 1.8 mL) to 2-[5-(1-bromoethyl)-1,2,4-triazol-1-yl]pyridine (1.80 g) in a sealed tube at 0° C. and stir for 1 h. Allow to warm to r.t. and stir overnight. Concentrate under reduced pressure and triturate the residue in pentane to provide 1-[2-(2-pyridyl)-1,2,4-triazol-3-yl]ethanamine (1.10 g, 82%). LCMS (method 8): $R_t$ 2.51 min, m/z (ES+)=190 [M+H]$^+$.

Add (2,2-difluorocyclopropyl)methyl methanesulfonate (500 mg) to a mixture of 1-[2-(2-pyridyl)-1,2,4-triazol-3-yl]ethanamine (660 mg) and K$_2$CO$_3$ (1.11 g) in DMF (5.0 mL) and stir at r.t. overnight. Dilute with water and extract three times with EtOAc. Wash the organic extracts with NaCl (aq. sat.), dry over Na$_2$SO$_4$, filter, concentrate under reduced pressure and purify the residue by chromatography to provide N-[(2,2-difluorocyclopropyl)methyl]-1-[2-(2-pyridyl)-1,2,4-triazol-3-yl]ethanamine (250 mg, 32%). LCMS (method 7): $R_t$ 1.66 min, m/z (ES+)=280 [M+H]$^+$.

PREPARATION 23

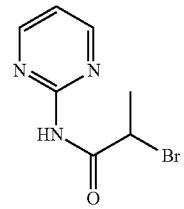

2-Bromo-N-pyrimidin-2-yl-propanamide

Add 2-aminopyrimidine (1.72 g) and triethylamine (1.85 mL) to 2-bromopropanoyl chloride (900 µL) in toluene (30 mL) and stir at reflux for 2 h. Cool to r.t. and partition between NaHCO$_3$ (aq. sat.) and EtOAc, separate the layers, dry the organic phase over MgSO$_4$, filter, concentrate under reduced pressure and purify the residue by chromatography to provide 2-bromo-N-pyrimidin-2-yl-propanamide (750 mg, 40%). $^1$H NMR (400 MHz. CDCl$_3$) δ ppm 1.64 (3 H, d, J 6.7 Hz), 5.03 (1 H, q, J 6.7 Hz), 7.20 (1 H, t, J 4.8 Hz), 8.67 (2 H, d, J 4.9 Hz), 10.42 (1 H, s).

PREPARATION 24

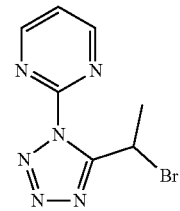

2-[5-(1-Bromoethyl)tetrazol-1-yl]pyrimidine

Add phosphorus pentachloride (360 mg) to a solution of 2-bromo-N-pyrimidin-2-yl-propanamide (304 mg) in CH$_2$Cl$_2$ (6.5 mL) and stir at r.t. for 5 h. Cool to 0° C., add trimethylsilyl azide (280 µL), warm to r.t. and stir overnight. Partition between NaHCO$_3$ (aq. sat.) and CH$_2$Cl$_2$, separate the layers and wash the organic phase with water. Dry the organic phase over MgSO$_4$, filter, concentrate under reduced pressure and purify the residue by chromatography to provide 2-[5-(1-bromoethyl)tetrazol-1-yl]pyrimidine (333 mg, 38%). $^1$H NMR (400 MHz, CDCl$_3$) δ ppm 2.20 (3 H, d, J 6.9 Hz), 6.16-6.22 (1 H, m), 7.57 (1 H, t, J 4.9 Hz), 9.00 (2 H, dd, J 4.9, 1.1 Hz).

PREPARATION 25

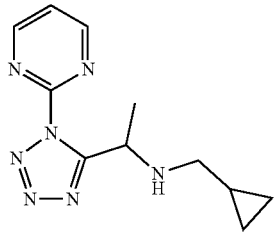

N-(Cyclopropylmethyl)-1-(1-pyrimidin-2-yltetrazol-5-yl)ethanamine

Add K$_2$CO$_3$ (213 mg) and cyclopropylmethanamine (90 ILL) to a solution of 2-[5-(1-bromoethyl)tetrazol-1-yl]pyrimidine (120 mg) in acetonitrile (2.0 mL) and stir at reflux for 3.5 h and at r.t. for 5 days. Concentrate under reduced pressure, partition the residue between water and EtOAc, separate the layers and extract the aqueous phase with EtOAc. Dry the combined organic extracts over MgSO$_4$, filter, concentrate under reduced pressure and purify the residue by chromatography to provide N-(cyclopropylmethyl)-1-(1-pyrimidin-2-yltetrazol-5-yl)ethanamine (34 mg, 29%). LCMS (method 5): R$_t$ 0.56 min, m/z (ES+)=246 [M+H]$^+$.

EXAMPLE 1

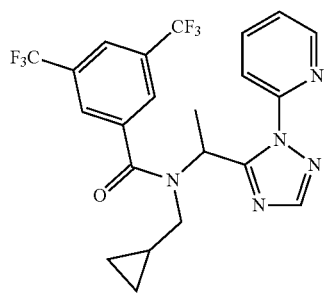 [SMILES: CC(c1ncnn1-c1ccccn1)N(CC1CC1)C(=O)c1cc(C(F)(F)F)cc(C(F)(F)F)c1]

N-(Cyclopropylmethyl)-N-[1-[2-(2-pyridyl)-1,24-triazol-3-yl]ethyl]-3,5-bis(trifluoromethyl)benzamide Add 3,5-bis(trifluoromethyl)benzoic acid (12.1 g) to a solution of N-(cyclopropylmethyl)-1-[2-(2-pyridyl)-1,2,4-triazol-3-yl]ethanamine (10.4 g) and DIPEA (24.6 mL) in EtOAc (415 mL) and stir the mixture at r.t. for 10 min. Add T3P® (≥50 wt. % in EtOAc, 45.7 mL) and stir at r.t. overnight. Partition the mixture between water and EtOAc, separate the layers and wash the organic phase sequentially with water, NaHCO$_3$ (aq. sat.) and NH$_4$Cl (aq. sat.). Dry over MgSO$_4$, filter, concentrate under reduced pressure and purify the residue by chromatography to provide N-(cyclopropylmethyl)-N-[1-[2-(2-pyridyl)-1,2,4-triazol-3-yl]ethyl]-3,5-bis(trifluoromethyl)benzamide (17.2 g, 83%). LCMS (method 2): R$_t$ 1.86 min, m/z (ES+)=484 [M+H]$^+$.

The compounds of Examples 2-32 and 50-60 set forth in table 2 may be prepared essentially as described in Example 1.

TABLE 2

| Example | Structure | Compound | LCMS method | Remarks |
|---|---|---|---|---|
| 2 | 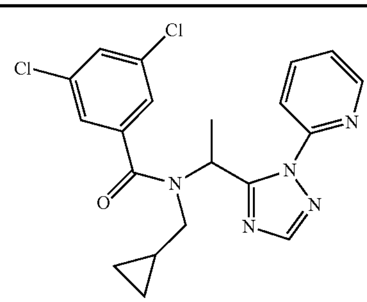 | 3,5-Dichloro-N-(cyclopropylmethyl)-N-[1-[2-(2-pyridyl)-1,2,4-triazol-3-yl]ethyl]benzamide | LCMS (method 2): R$_t$ 1.79 min, m/z (ES+) = 416 [M + H]$^+$ | — |
| 3 | 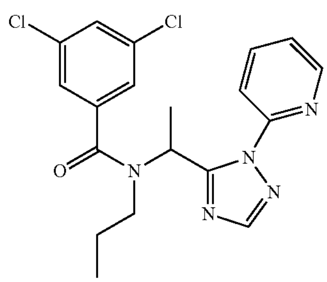 [SMILES: CCCN(C(=O)c1cc(Cl)cc(Cl)c1)C(C)c1ncnn1-c1ccccn1] | 3,5-Dichloro-N-propyl-N-[1-2-(2-pyridyl)-1,2,4-triazol-3-yl]ethyl]benzamide | LCMS (method 2): R$_t$ 1.78 min, m/z (ES+) = 404 [M + H]$^+$ | Reaction time: 48 h |

TABLE 2-continued

| Example | Structure | Compound | LCMS method | Remarks |
|---|---|---|---|---|
| 4 | 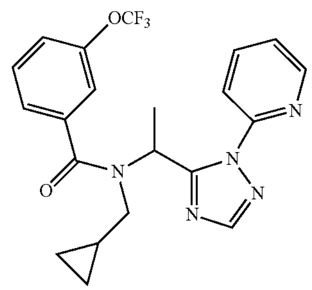 [SMILES: CC(c1ncnn1-c1ccccn1)N(CC1CC1)C(=O)c1cccc(OC(F)(F)F)c1] | N-(Cyclopropylmethyl)-N-[1-[2-(2-pyridyl)-1,2,4-triazol-3-yl]ethyl]-3-(trifluoromethoxy)benzamide | LCMS (method 1): $R_t$ 2.59 min, m/z (ES+) = 432 [M + H]$^+$ | — |
| 5 | 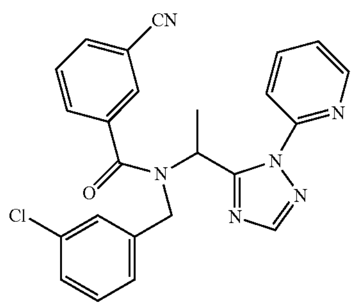 [SMILES: CC(c1ncnn1-c1ccccn1)N(Cc1cccc(Cl)c1)C(=O)c1cccc(C#N)c1] | N-[(3-Chlorophenyl)methyl]-3-cyano-N-[1-[2-(2-pyridyl)-1,2,4-triazol-3-yl]ethyl]benzamide | LCMS (method 1): $R_t$ 2.52 min, m/z (ES+) = 443 [M + H]$^+$ | — |
| 6 | 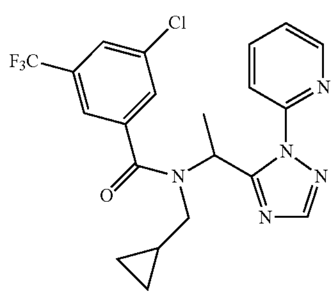 [SMILES: CC(c1ncnn1-c1ccccn1)N(CC1CC1)C(=O)c1cc(Cl)cc(C(F)(F)F)c1] | 3-Chloro-N-(cyclopropylmethyl)-N-[1-[2-(2-pyridyl)-1,2,4-triazol-3-yl]ethyl]-5-(trifluoromethyl)benzamide | LCMS (method 1): $R_t$ 2.68 min, m/z (ES+) = 450 [M + H]$^+$ | — |
| 7 | 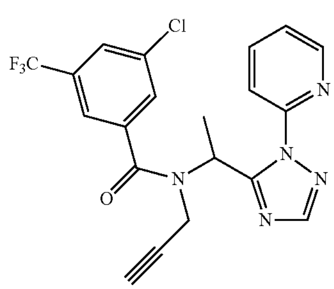 [SMILES: C#CCN(C(=O)c1cc(Cl)cc(C(F)(F)F)c1)C(C)c1ncnn1-c1ccccn1] | 3-Chloro-N-prop-2-ynyl-N-[1-[2-(2-pyridyl)-1,2,4-triazol-3-yl]ethyl]-5-(trifluoromethyl)benzamide | LCMS (method 1): $R_t$ 2.55 min, m/z (ES+) = 434 [M + H]$^+$ | — |
| 8 | 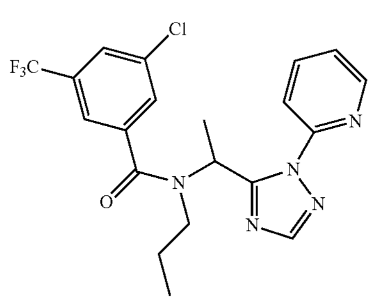 [SMILES: CCCN(C(=O)c1cc(Cl)cc(C(F)(F)F)c1)C(C)c1ncnn1-c1ccccn1] | 3-Chloro-N-propyl-N-[1-[2-(2-pyridyl)-1,2,4-triazol-3-yl]ethyl]-5-(trifluoromethyl)benzamide | LCMS (method 1): $R_t$ 2.70 min, m/z (ES+) = 438 [M + H]$^+$ | — |

TABLE 2-continued

| Example | Structure | Compound | LCMS method | Remarks |
|---|---|---|---|---|
| 9 | 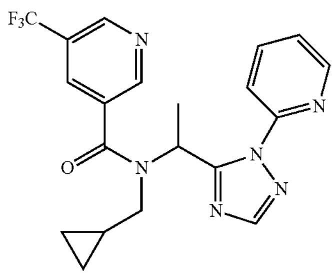 [SMILES: CC(c1ncnn1-c1ccccn1)N(CC1CC1)C(=O)c1cncc(C(F)(F)F)c1] | N-(Cyclopropylmethyl)-N-[1-[2-(2-pyridyl)-1,2,4-triazol-3-yl]ethyl]-5-(trifluoromethyl)pyridine-3-carboxamide | LCMS (method 1): R$_t$ 2.34 min, m/z (ES+) = 417 [M + H]$^+$ | Reaction time: 2 h |
| 10 | 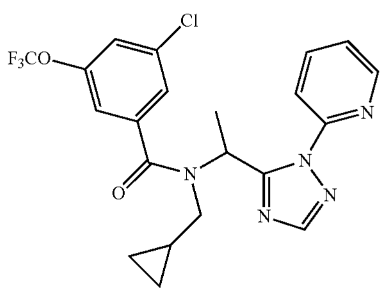 [SMILES: CC(c1ncnn1-c1ccccn1)N(CC1CC1)C(=O)c1cc(Cl)cc(OC(F)(F)F)c1] | 3-Chloro-N-(cyclopropylmethyl)-N-[1-[2-(2-pyridyl)-1,2,4-triazol-3-yl]ethyl]-5-(trifluoromethoxy)benzamide | LCMS (method 1): R$_t$ 2.75 min, m/z (ES+) = 466 [M + H]$^+$ | Reaction time: 2 h T = 50° C. |
| 11 | 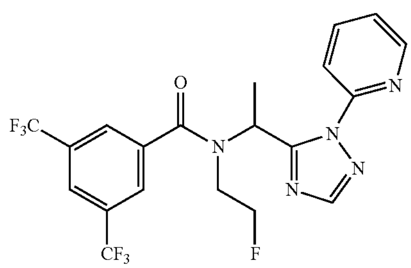 [SMILES: CC(c1ncnn1-c1ccccn1)N(CCF)C(=O)c1cc(C(F)(F)F)cc(C(F)(F)F)c1] | N-(2-Fluoroethyl)-N-[1-[2-(2-pyridyl)-1,2,4-triazol-3-yl]ethyl]-3,5-bis(trifluoromethyl)benzamide | LCMS (method 1): R$_t$ 2.63 min, m/z (ES+) = 476 [M + H]$^+$ | — |
| 12 | 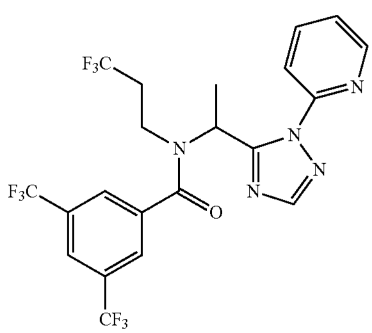 [SMILES: CC(c1ncnn1-c1ccccn1)N(CCC(F)(F)F)C(=O)c1cc(C(F)(F)F)cc(C(F)(F)F)c1] | N-[1-[2-(2-Pyridyl)-1,2,4-triazol-3-yl]ethyl]-3,5-bis(trifluoromethyl)-N-(3,3,3-trifluoropropyl)benzamide | LCMS (method 1): R$_t$ 2.77 min, m/z (ES+) = 526 [M + H]$^+$ | — |
| 13 | 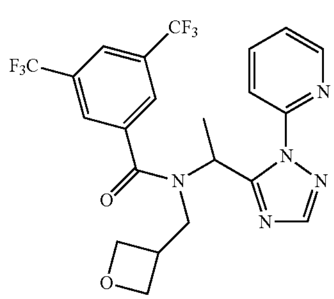 [SMILES: CC(c1ncnn1-c1ccccn1)N(CC1COC1)C(=O)c1cc(C(F)(F)F)cc(C(F)(F)F)c1] | N-(Oxetan-3-ylmethyl)-N-[1-[2-(2-pyridyl)-1,2,4-triazol-3-yl]ethyl]-3,5-bis(trifluoromethyl)benzamide | LCMS (method 1): R$_t$ 2.51 min, m/z (ES+) = 500 [M + H]$^+$ | — |

TABLE 2-continued

| Example | Structure | Compound | LCMS method | Remarks |
|---|---|---|---|---|
| 14 | 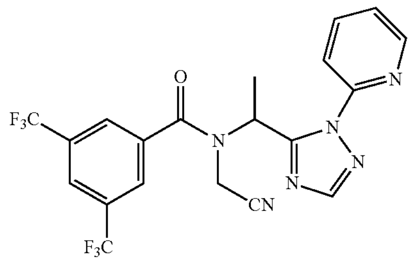 [SMILES: CC(c1ncnn1-c1ccccn1)N(CC#N)C(=O)c1cc(C(F)(F)F)cc(C(F)(F)F)c1] | N-(Cyanomethyl)-N-[1-[2-(2-pyridyl)-1,2,4-triazol-3-yl]ethyl]-3,5-bis(trifluoromethyl)benzamide | LCMS (method 1): R$_t$ 2.58 min, m/z (ES+) = 469 [M + H]$^+$ | — |
| 15 | 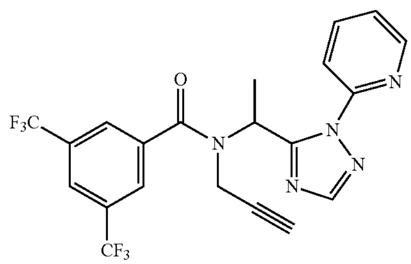 [SMILES: C#CCN(C(=O)c1cc(C(F)(F)F)cc(C(F)(F)F)c1)C(C)c1ncnn1-c1ccccn1] | N-Prop-2-ynyl-N-[2-(2-pyridyl)-1,2,4-triazol-3-yl]ethyl]-3,5-bis(trifluoromethyl)benzamide | LCMS (method 1): R$_t$ 2.60 min, m/z (ES+) = 468 [M + H]$^+$ | Reaction time: 48 h |
| 16 | 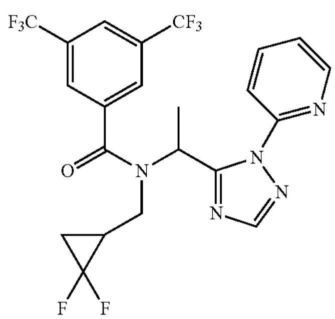 [SMILES: CC(c1ncnn1-c1ccccn1)N(CC1CC1(F)F)C(=O)c1cc(C(F)(F)F)cc(C(F)(F)F)c1] | N-[(2,2-Difluorocyclopropyl)methyl]-N-[1-[2-(2-pyridyl)-1,2,4-triazol-3-yl]ethyl]-3,5-bis(trifluoromethyl)benzamide | LCMS (method 1): R$_t$ 2.72 min, m/z (ES+) = 520 [M + H]$^+$ | — |
| 17 | 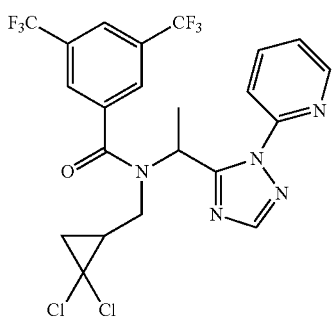 | N-[(2,2-Dichlorocyclopropyl)methyl]-N-[1-[2-(2-pyridyl)-1,2,4-triazol-3-yl]ethyl]-3,5-bis(trifluoromethyl)benzamide | LCMS (method 1): R$_t$ 2.83 min, m/z (ES+) = 552 [M + H]$^+$ | — |
| 18 | 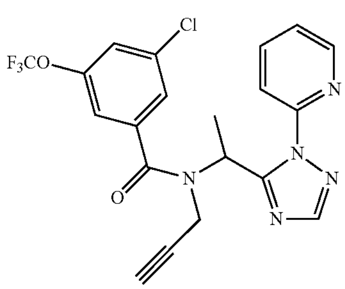 [SMILES: C#CCN(C(=O)c1cc(Cl)cc(OC(F)(F)F)c1)C(C)c1ncnn1-c1ccccn1] | 3-Chloro-N-prop-2-ynyl-N-[1-[2-(2-pyridyl)-1,2,4-triazol-3-yl]ethyl]-5-(trifluoromethoxy)benzamide | LCMS (method 1): R$_t$ 2.60 min, m/z (ES+) = 450 [M + H]$^+$ | T = 80° C. |

TABLE 2-continued

| Example | Structure | Compound | LCMS method | Remarks |
|---|---|---|---|---|
| 19 | 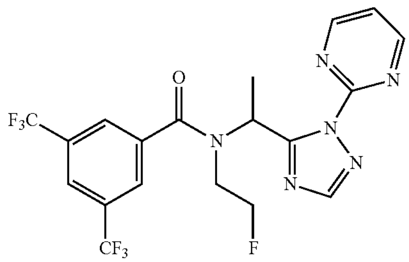 [SMILES: CC(c1ncnn1-c1ncccn1)N(CCF)C(=O)c1cc(C(F)(F)F)cc(C(F)(F)F)c1] | N-(2-Fluoroethyl)-N-[1-(2-pyrimidin-2-yl-1,2,4-triazol-3-yl)ethyl]-3,5-bis(trifluoromethyl)benzamide | LCMS (method 2): $R_t$ 1.51 min, m/z (ES+) = 477 [M + H]⁺ | Triple amount of carboxylic acid and T3P® |
| 20 | 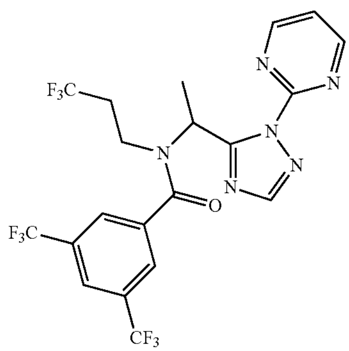 [SMILES: CC(c1ncnn1-c1ncccn1)N(CCC(F)(F)F)C(=O)c1cc(C(F)(F)F)cc(C(F)(F)F)c1] | N-[1-(2-Pyrimidin-2-yl-1,2,4-triazol-3-yl)ethyl]-3,5-bis(trifluoromethyl)-N-(3,3,3-trifluoropropyl)benzamide | LCMS (method 2): $R_t$ 1.73 min, m/z (ES+) = 527 [M + H]⁺ | Reaction time: 1 h |
| 21 | 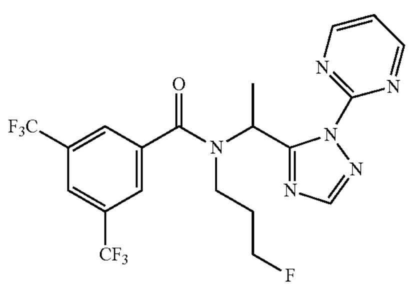 [SMILES: CC(c1ncnn1-c1ncccn1)N(CCCF)C(=O)c1cc(C(F)(F)F)cc(C(F)(F)F)c1] | N-(3-Fluoropropyl)-N-[1-(2-pyrimidin-2-yl-1,2,4-triazol-3-yl)ethyl]-3,5-bis(trifluoromethyl)benzamide | LCMS (method 2): $R_t$ 1.55 min, m/z (ES+) = 491 [M + H]⁺ | Reaction time: 1 h 45 min |
| 22 | 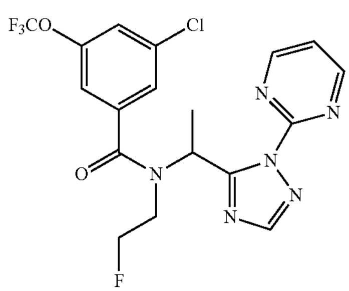 [SMILES: CC(c1ncnn1-c1ncccn1)N(CCF)C(=O)c1cc(Cl)cc(OC(F)(F)F)c1] | 3-Chloro-N-(2-fluoroethyl)-N-[1-(2-pyrimidin-2-yl-1,2,4-triazol-3-yl)ethyl]-5-(trifluoromethoxy)benzamide | LCMS (method 2): $R_t$ 1.50 min, m/z (ES+) = 459 [M + H]⁺ | Reaction time: 1 h |
| 23 | 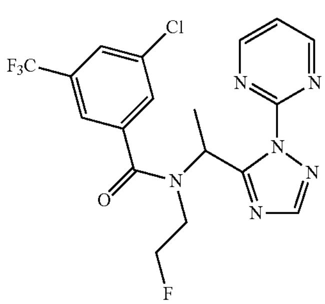 [SMILES: CC(c1ncnn1-c1ncccn1)N(CCF)C(=O)c1cc(Cl)cc(C(F)(F)F)c1] | 3-Chloro-N-(2-fluoroethyl)-N-[1-(2-pyrimidin-2-yl-1,2,4-triazol-3-yl)ethyl]-5-(trifluoromethyl)benzamide | LCMS (method 4): $R_t$ 1.30 min, m/z (ES+) = 443 [M + H]⁺ | Double amount of carboxylic acid and T3P® |

TABLE 2-continued

| Example | Structure | Compound | LCMS method | Remarks |
|---|---|---|---|---|
| 24 | 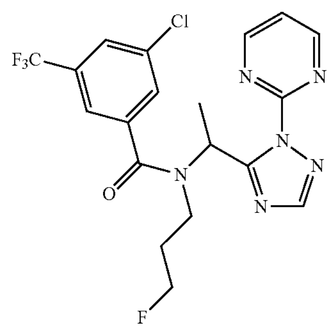 [SMILES: CC(c1ncnn1-c1ncccn1)N(CCCF)C(=O)c1cc(Cl)cc(C(F)(F)F)c1] | 3-Chloro-N-(3-fluoropropyl)-N-[1-(2-pyrimidin-2-yl-1,2,4-triazol-3-yl)ethyl]-5-(trifluoromethyl)benzamide | LCMS (method 5): $R_t$ 2.41 min, m/z (ES+) = 457 [M + H]$^+$ | — |
| 25 | 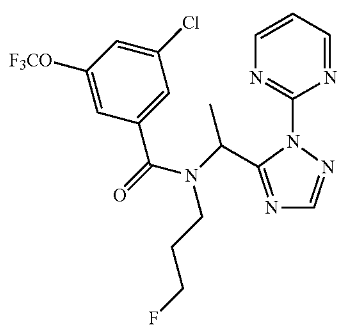 [SMILES: CC(c1ncnn1-c1ncccn1)N(CCCF)C(=O)c1cc(Cl)cc(OC(F)(F)F)c1] | 3-Chloro-N-(3-fluoropropyl)-N-[1-(2-pyrimidin-2-yl-1,2,4-triazol-3-yl)ethyl]-5-(trifluoromethoxy)benzamide | LCMS (method 5): $R_t$ 2.46 min, m/z (ES+) = 473 [M + H]$^+$ | — |
| 26 | 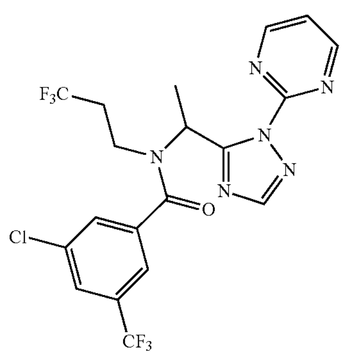 [SMILES: CC(c1ncnn1-c1ncccn1)N(CCC(F)(F)F)C(=O)c1cc(Cl)cc(C(F)(F)F)c1] | 3-Chloro-N-[1-(2-pyrimidin-2-yl-1,2,4-triazol-3-yl)ethyl]-5-(trifluoromethyl)-N-(3,3,3-trifluoropropyl)benzamide | LCMS (method 5): $R_t$ 2.63 min, m/z (ES+) = 493 [M + H]$^+$ | Reaction time: 3 h |
| 27 | 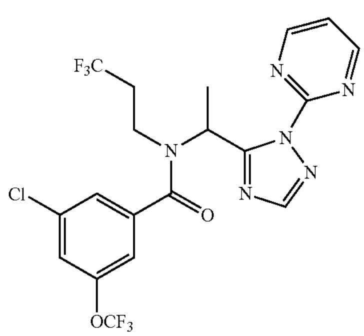 [SMILES: CC(c1ncnn1-c1ncccn1)N(CCC(F)(F)F)C(=O)c1cc(Cl)cc(OC(F)(F)F)c1] | 3-Chloro-N-[1-(2-pyrimidin-2-yl-1,2,4-triazol-3-yl)ethyl]-5-(trifluoromethoxy)-N-(3,3,3-trifluoropropyl)benzamide | LCMS (method 5): $R_t$ 2.68 min, m/z (ES+) = 509 [M + H]$^+$ | Reaction time: 3 h |

TABLE 2-continued

| Example | Structure | Compound | LCMS method | Remarks |
|---|---|---|---|---|
| 28 | 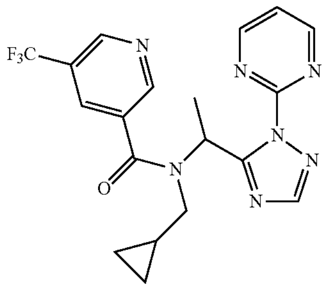 [SMILES: CC(c1ncnn1-c1ncccn1)N(CC1CC1)C(=O)c1cncc(C(F)(F)F)c1] | N-(Cyclopropylmethyl)-N-[1-(2-pyrimidin-2-yl-1,2,4-triazol-3-yl)ethyl]-5-(trifluoromethyl)pyridine-3-carboxamide | LCMS (method 4): $R_t$ 0.74 min, m/z (ES+) = 418 [M + H]$^+$ | — |
| 29 | 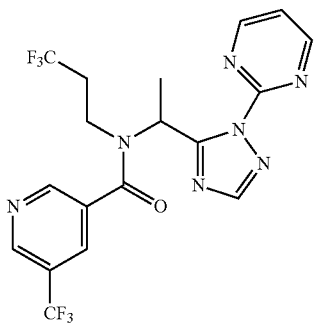 [SMILES: CC(c1ncnn1-c1ncccn1)N(CCC(F)(F)F)C(=O)c1cncc(C(F)(F)F)c1] | N-[1-(2-Pyrimidin-2-yl-1,2,4-triazol-3-yl)ethyl]-5-(trifluoromethyl)-N-(3,3,3-trifluoropropyl)pyridine-3-carboxamide | LCMS (method 5): $R_t$ 2.28 min, m/z (ES+) = 460 [M + H]$^+$ | Reaction time: 3 h |
| 30 | 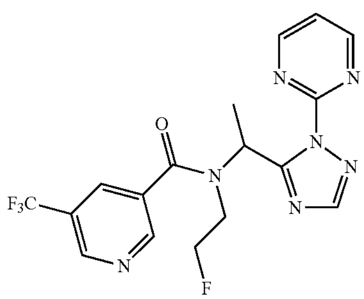 [SMILES: CC(c1ncnn1-c1ncccn1)N(CCF)C(=O)c1cncc(C(F)(F)F)c1] | N-(2-Fluoroethyl)-N-[1-(2-pyrimidin-2-yl-1,2,4-triazol-3-yl)ethyl]-5-(trifluoromethyl)pyridine-3-carboxamide | LCMS (method 3): $R_t$ 2.24 min, m/z (ES+) = 410 [M + H]$^+$ | — |
| 31 | 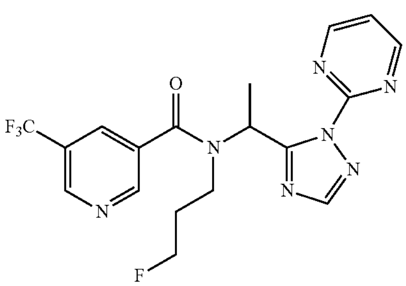 [SMILES: CC(c1ncnn1-c1ncccn1)N(CCCF)C(=O)c1cncc(C(F)(F)F)c1] | N-(3-Fluoropropyl)-N-[1-(2-pyrimidin-2-yl-1,2,4-triazol-3-yl)ethyl]-5-(trifluoromethyl)pyridine-3-carboxamide | LCMS (method 3): $R_t$ 2.28 min, m/z (ES+) = 424 [M + H]$^+$ | Reaction time: 1 h |
| 32 | 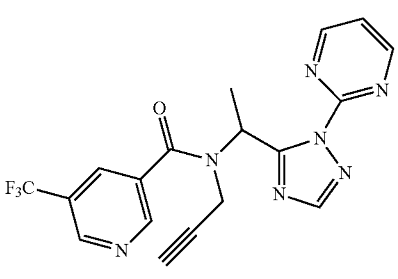 [SMILES: C#CCN(C(=O)c1cncc(C(F)(F)F)c1)C(C)c1ncnn1-c1ncccn1] | N-Prop-2-ynyl-N-[1-(2-pyrimidin-2-yl-1,2,4-triazol-3-yl)ethyl]-5-(trifluoromethyl)pyridine-3-carboxamide | LCMS (method 4): $R_t$ 0.67 min, m/z (ES+) = 402 [M + H]$^+$ | Reaction time: 2 h; No work-up |

TABLE 2-continued

| Example | Structure | Compound | LCMS method | Remarks |
|---|---|---|---|---|
| 50 | 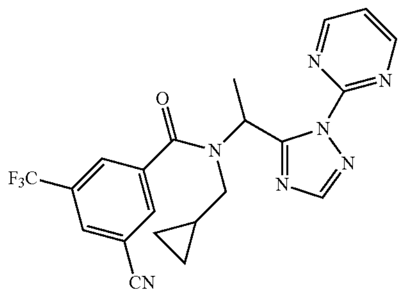 [SMILES: CC(c1ncnn1-c1ncccn1)N(CC1CC1)C(=O)c1cc(C#N)cc(C(F)(F)F)c1] | 3-Cyano-N-(cyclopropylmethyl)-N-[1-(2-pyrimidin-2-yl-1,2,4-triazol-3-yl)ethyl]-5-(trifluoromethyl)benzamide | LCMS (method 4): Rt 1.47 min, m/z (ES+) = 442 [M + H]+ | Reaction time: 1.5 h; No work-up |
| 51 | 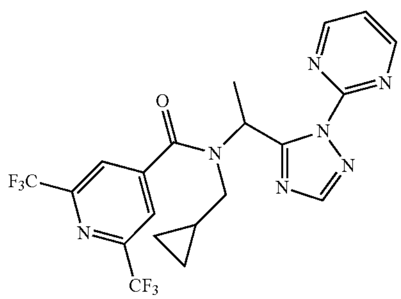 [SMILES: CC(c1ncnn1-c1ncccn1)N(CC1CC1)C(=O)c1cc(C(F)(F)F)nc(C(F)(F)F)c1] | N-(Cyclopropylmethyl)-N-[1-(2-pyrimidin-2-yl-1,2,4-triazol-3-yl)ethyl]-2,6-bis(trifluoromethyl)pyridine-4-carboxamide | LCMS (method 2): Rt 1.72 min, m/z (ES+) = 486 [M + H]+ | — |
| 52 | 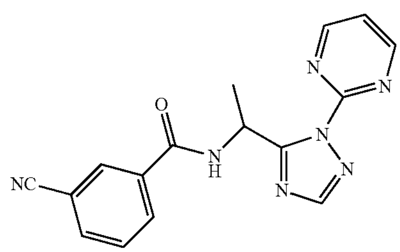 [SMILES: CC(NC(=O)c1cccc(C#N)c1)c1ncnn1-c1ncccn1] | 3-Cyano-N-[1-(2-pyrimidin-2-yl-1,2,4-triazol-3-yl)ethyl]benzamide | LCMS (method 5): Rt 1.29 min, m/z (ES+) = 320 [M + H]+ | — |
| 53 | 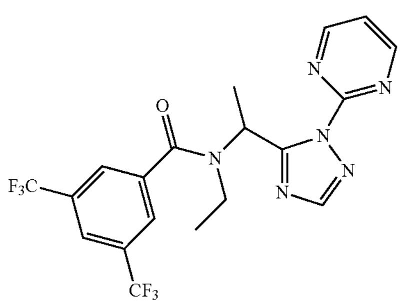 [SMILES: CCN(C(=O)c1cc(C(F)(F)F)cc(C(F)(F)F)c1)C(C)c1ncnn1-c1ncccn1] | N-Ethyl-N-[1-(2-pyrimidin-2-yl-1,2,4-triazol-3-yl)ethyl]-3,5-bis(trifluoromethyl)benzamide | LCMS (method 4): Rt 1.63 min, m/z (ES+) = 459 [M + H]+ | Double amount of T3P ® |
| 54 | 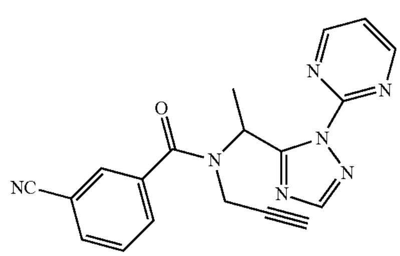 [SMILES: C#CCN(C(=O)c1cccc(C#N)c1)C(C)c1ncnn1-c1ncccn1] | 3-Cyano-N-prop-2-ynyl-N-[1-(2-pyrimidin-2-yl-1,2,4-triazol-3-yl)ethyl]benzamide | LCMS (method 4): Rt 0.54 min, m/z (ES+) = 358 [M + H]+ | Reaction time: 1 h; No work-up |

TABLE 2-continued

| Example | Structure | Compound | LCMS method | Remarks |
|---|---|---|---|---|
| 55 | 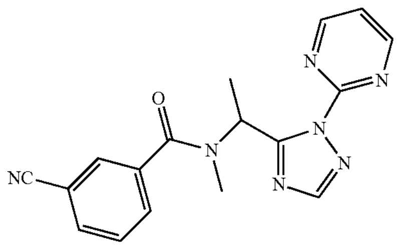 [SMILES: CC(c1ncnn1-c1ncccn1)N(C)C(=O)c1cccc(C#N)c1] | 3-Cyano-N-methyl-N-[1-(2-pyrimidin-2-yl-1,2,4-triazol-3-yl)ethyl]benzamide | LCMS (method 4): Rt 0.48 min, m/z (ES+) = 334 [M + H]+ | Reaction time: 2.5 h |
| 56 | 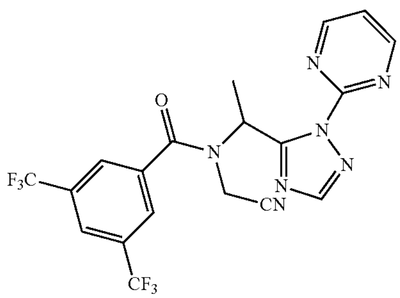 [SMILES: CC(c1ncnn1-c1ncccn1)N(CC#N)C(=O)c1cc(C(F)(F)F)cc(C(F)(F)F)c1] | N-(Cyanomethyl)-N-[1-(2-pyrimidin-2-yl-1,2,4-triazol-3-yl)ethyl]-3,5-bis(trifluoromethyl)benzamide | LCMS (method 4): Rt 1.60 min, m/z (ES+) = 470 [M + H]+ | — |
| 57 | 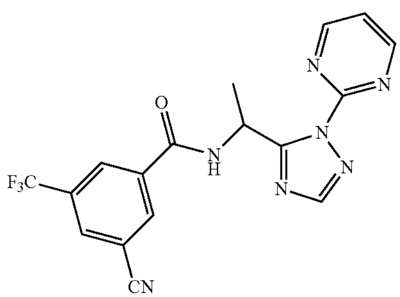 [SMILES: CC(NC(=O)c1cc(C#N)cc(C(F)(F)F)c1)c1ncnn1-c1ncccn1] | 3-Cyano-N-[1-(2-pyrimidin-2-yl-1,2,4-triazol-3-yl)ethyl]-5-(trifluoromethyl)benzamide | LCMS (method 4): Rt 1.06 min, m/z (ES+) = 388 [M + H]+ | Reaction time: 3 h |
| 58 | 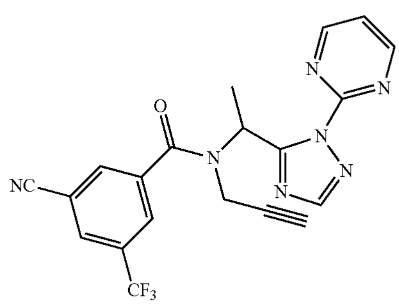 [SMILES: C#CCN(C(=O)c1cc(C#N)cc(C(F)(F)F)c1)C(C)c1ncnn1-c1ncccn1] | 3-Cyano-N-prop-2-ynyl-N-[1-(2-pyrimidin-2-yl-1,2,4-triazol-3-yl)ethyl]-5-(trifluoromethyl)benzamide | LCMS (method 4): Rt 1.24 min, m/z (ES+) = 426 [M + H]+ | Reaction time: 1.5 h; No work-up |
| 59 | 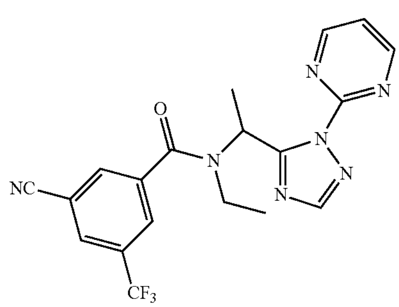 [SMILES: CCN(C(=O)c1cc(C#N)cc(C(F)(F)F)c1)C(C)c1ncnn1-c1ncccn1] | 3-Cyano-N-ethyl-N-[1-(2-pyrimidin-2-yl-1,2,4-triazol-3-yl)ethyl]-5-(trifluoromethyl)benzamide | LCMS (method 4): Rt 1.24 min, m/z (ES+) = 416 [M + H]+ | Reaction time: 3 h |

TABLE 2-continued

| Example | Structure | Compound | LCMS method | Remarks |
|---|---|---|---|---|
| 60 | 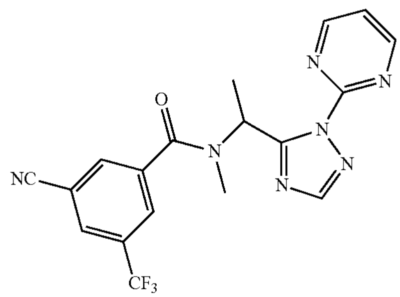 [SMILES: CC(c1ncnn1-c1ncccn1)N(C)C(=O)c1cc(C#N)cc(C(F)(F)F)c1] | 3-Cyano-N-methyl-N-[1-(2-pyrimidin-2-yl-1,2,4-triazol-3-yl)ethyl]-5-(trifluoromethyl)benzamide | LCMS (method 4): Rt 1.04 min, m/z (ES+) = 402 [M + H]+ | Reaction time: 3 h |

EXAMPLE 33

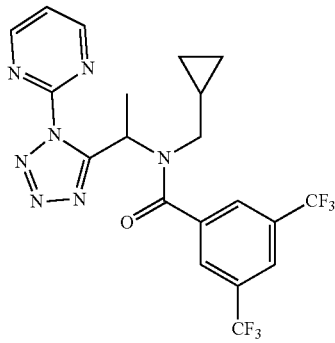 [SMILES: CC(c1nnnn1-c1ncccn1)N(CC1CC1)C(=O)c1cc(C(F)(F)F)cc(C(F)(F)F)c1]

N-(Cyclopropylmethyl)-N-[1-(1-pyrimidin-2-yltetrazol-5-yl)ethyl]-3,5-bis(trifluoromethyl)benzamide Add 3,5-bis(trifluoromethyl)benzoic acid (43 mg) and T3P® (≥50 wt. % in EtOAc, 130 μL) to a solution of N-(cyclopropylmethyl)-1-(1-pyrimidin-2-yltetrazol-5-yl)ethanamine (30 mg) and DIPEA (73 μL) in EtOAc (1.5 mL) and stir at r.t. for 2.5 h. Partition between water and EtOAc, separate the layers and wash the organic phase sequentially with water, NaHCO₃ (aq. sat.) and NH₄Cl (aq. sat.). Dry the organic phase over MgSO₄, filter, concentrate under reduced pressure and purify the residue by chromatography to provide N-(cyclopropylmethyl)-N-[1-(1-pyrimidin-2-yltetrazol-5-yl)ethyl]-3,5-bis(trifluoromethyl)benzamide (32 mg, 54%). LCMS (method 2): R$_t$ 1.76 min, m/z (ES+)=486 [M+H]⁺.

PREPARATION 26

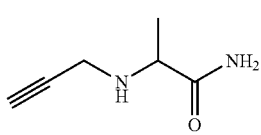

2-(Prop-2-ynylamino)propanamide

Add K₂CO₃ (55 g) and propargylamine (17 mL) to 2-bromopropanamide (20.2 g) in acetonitrile (320 mL) and stir at 80° C. for 3.5 h and at r.t. overnight. Concentrate under reduced pressure, partition the residue between water and EtOAc, separate the layers and extract the aqueous phase twice with EtOAc. Dry the combined organic extracts over MgSO₄, filter and concentrate under reduced pressure to provide 2-(prop-2-ynylamino)propanamide (15.7 g, 93%). ¹H NMR (400 MHz, CDCl₃) δ ppm 1.36 (3 H, d, J 7.0 Hz), 1.58 (1 H, br s), 2.23 (1 H, t, J 2.4 Hz), 3.34 (1 H, dd, J 17.1, 2.4 Hz), 3.41 (1 H, q, J 7.0 Hz), 3.49 (1 H, dd, J 17.1, 2.5 Hz), 5.39 (1 H, br s), 6.93 (1 H, br s).

PREPARATION 27

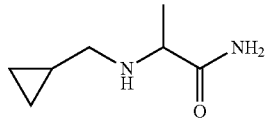

2-(Cyclopropylmethylamino)propanamide

Add K₂CO₃ (1.45 g) and cyclopropylmethanamine (560 μL) to 2-bromopropanamide (490 mg) and in acetonitrile (8 mL) and stir at 80° C. for 1 h. Cool to r.t., filter through Celite® and wash with acetonitrile. Partition the residue between water and EtOAc, separate the layers and extract the aqueous phase twice with EtOAc. Dry the combined organic extracts over MgSO₄, filter and concentrate under reduced pressure to provide 2-(cyclopropylmethylamino)propanamide (351 mg, 77%). ¹H NMR (400 MHz. CDCl₃) δ ppm 0.06-0.23 (2 H, m), 0.44-0.58 (2 H, m), 0.83-1.02 (1 H, m), 1.36 (3 H, d, J 6.9 Hz), 1.73 (1 H, br s), 2.42 (1 H, dd, J 12.4, 6.9 Hz), 2.55 (1 H, dd, J 12.1, 6.6 Hz), 3.24 (1 H, q, J 6.9 Hz), 5.39 (1 H, br s), 7.18 (1 H, br s).

PREPARATION 28

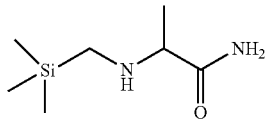

2-(Trimethylsilylmethylamino)propanamide

Add K₂CO₃ (628 mg) and (aminomethyl)trimethylsilane (341 mg) to 2-bromopropanamide (456 mg) in acetonitrile (5 mL) and stir at reflux overnight. Cool to r.t., filter, wash with acetonitrile and dry the resulting solid under reduced pressure to provide 2-(trimethylsilylmethylamino)propanamide (512 mg, 98%). $^1$H NMR (400 MHz, CDCl$_3$) δ ppm 0.05 (9 H, s), 1.31 (3 H, d, J 6.9 Hz), 3.09 (1 H, q, J 6.9 Hz), 5.63 (1H, br s), 7.04 (1 H, br s).

PREPARATION 29

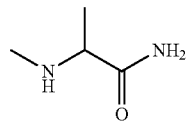

2-(Methylamino)propanamide

Add K$_2$CO$_3$ (4.15 g) and methylamine (2 M in THF, 10 mL) to 2-bromopropanamide (1.53 g) in acetonitrile (30 mL) and stir at 80° C. overnight. Cool to r.t., filter, wash with MeOH and dry the resulting solid under reduced pressure to provide 2-(methylamino)propanamide (792 mg, 77%). $^1$H NMR (400 MHz, DMSO-d$_6$) δ ppm 1.08 (3 H, d, J 6.9 Hz) 1.83 (1 H, br s) 2.18 (3 H, s) 2.77-2.90 (1 H, m) 6.92 (1 H, br s) 7.23 (1 H, br s).

PREPARATION 30

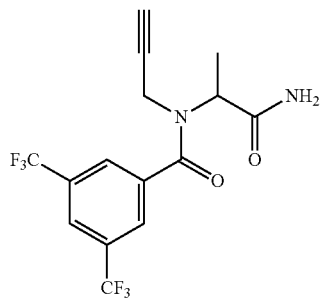 [SMILES: C#CCN(C(=O)c1cc(C(F)(F)F)cc(C(F)(F)F)c1)C(C)C(N)=O]

N-(2-Amino-1-methyl-2-oxo-ethyl)-N-prop-2-ynyl-3,5-bis(trifluoromethyl)benzamide Add DIPEA (73.7 g) to a solution of 2-(prop-2-ynylamino)propanamide (24.0 g) and 3,5-bis(trifluoromethyl)benzoic acid (58.9 g) in EtOAc (528 mL). Cool to 0° C. and add T3P' (≥50 wt. % in EtOAc, 170 mL) dropwise. Warm to r.t. and stir overnight. Partition between water and EtOAc, separate the layers, wash the organic phase with NaHCO$_3$ (aq. sat.) and NaOH (aq. 1 M). Dry the organic phase over Na$_2$SO$_4$, filter, concentrate under reduced pressure and purify the residue by trituration with pentane to provide N-(2-amino-1-methyl-2-oxo-ethyl)-N-prop-2-ynyl-3,5-bis(trifluoromethyl)benzamide (50 g, 72%). LCMS (method 7): R$_t$ 2.17 min, m/z (ES+)=367 [M+H]$^+$.

The compounds of Preparations 31-40 set forth in table 3 may be prepared essentially as described in Preparation 30.

TABLE 3

| Prep. | Structure | Compound | Analytical data | Remarks |
|---|---|---|---|---|
| 31 | 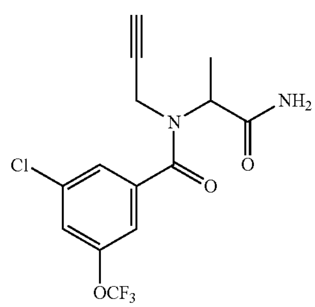 [SMILES: C#CCN(C(=O)c1cc(Cl)cc(OC(F)(F)F)c1)C(C)C(N)=O] | N-(2-amino-1-methyl-2-oxo-ethyl)-3-chloro-N-prop-2-ynyl-5-(trifluoromethoxy)benzamide | LCMS: (method 2) R$_t$ 1.41 min, m/z (ES−) 347 [M − H]$^−$ | Reaction time: 1 h 45 min; purification by chromatography |
| 32 | 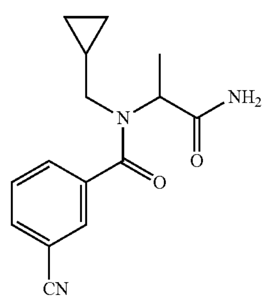 [SMILES: CC(C(N)=O)N(CC1CC1)C(=O)c1cccc(C#N)c1] | N-(2-Amino-1-methyl-2-oxo-ethyl)-3-cyano-N-(cyclopropylmethyl)benzamide | LCMS: (method 3) R$_t$ 2.07 min, m/z (ES+) 272 [M + H]$^+$ | Reaction time: 4 h; purification by chromatography |

TABLE 3-continued

| Prep. | Structure | Compound | Analytical data | Remarks |
|---|---|---|---|---|
| 33 | 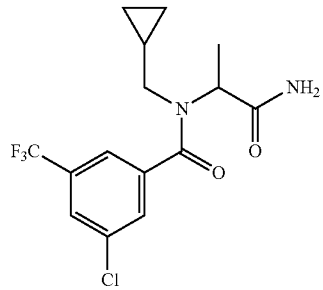 [SMILES: CC(C(N)=O)N(CC1CC1)C(=O)c1cc(Cl)cc(C(F)(F)F)c1] | N-(2-Amino-1-methyl-2-oxo-ethyl)-3-chloro-N-(cyclopropylmethyl)-5-(trifluoromethyl)benzamide | LCMS: (method 2) R$_t$ 1.46 min, m/z (ES+) 349 [M + H]$^+$ | Reaction time: 30 min; purification by chromatography |
| 34 | 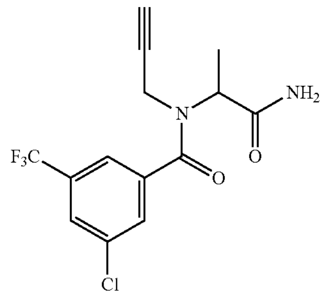 [SMILES: C#CCN(C(=O)c1cc(Cl)cc(C(F)(F)F)c1)C(C)C(N)=O] | N-(2-Amino-1-methyl-2-oxo-ethyl)-3-chloro-N-prop-2-ynyl-5-(trifluoromethyl)benzamide | LCMS: (method 4) R$_t$ 1.33 min, m/z (ES−) 331 [M − H]$^−$ | — |
| 35 | 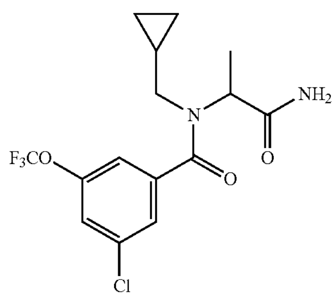 [SMILES: CC(C(N)=O)N(CC1CC1)C(=O)c1cc(Cl)cc(OC(F)(F)F)c1] | N-(2-amino-1-methyl-2-oxo-ethyl)-3-chloro-N-(cyclopropylmethyl)-5-(trifluoromethyl)benzamide | LCMS: (method 2) R$_t$ 1.51 min, m/z (ES−) 363 [M − H]$^−$ | Reaction time: 1 h 45 min; purification by chromatography |
| 36 | 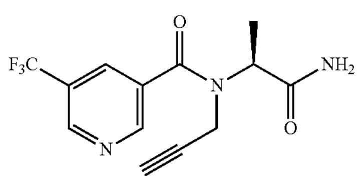 [SMILES: C#CCN(C(=O)c1cncc(C(F)(F)F)c1)[C@@H](C)C(N)=O] | N-[(1S)-2-Amino-1-methyl-2-oxo-ethyl]-N-prop-2-ynyl-5-(trifluoromethyl)pyridine-3-carboxamide | LCMS: (method 4) R$_t$ 0.54 min, m/z (ES+) 300 [M + H]$^+$ | Purification by chromatography |
| 37 | 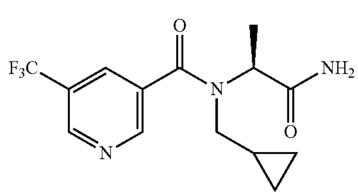 [SMILES: C[C@@H](C(N)=O)N(CC1CC1)C(=O)c1cncc(C(F)(F)F)c1] | N-[(1S)-2-Amino-1-methyl-2-oxo-ethyl]-N-(cyclopropylmethyl)-5-(trifluoromethyl)pyridine-3-carboxamide | LCMS: (method 4) R$_t$ 0.64 min, m/z (ES+) 316 [M + H]$^+$ | Purification by chromatography |
| 38 | 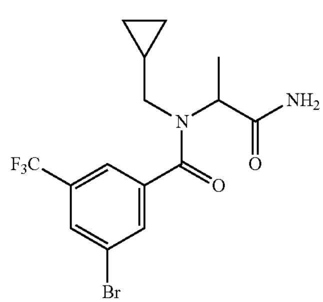 [SMILES: CC(C(N)=O)N(CC1CC1)C(=O)c1cc(Br)cc(C(F)(F)F)c1] | N-(2-Amino-1-methyl-2-oxo-ethyl)-3-bromo-N-(cyclopropylmethyl)-5-(trifluoromethyl)benzamide | LCMS: (method 4) Rt 1.55 min, m/z (ES−) 391 [M − H]$^−$ | Reaction time: 3 days; no aq. work-up; purification by chromatography |

TABLE 3-continued

| Prep. | Structure | Compound | Analytical data | Remarks |
|---|---|---|---|---|
| 39 | 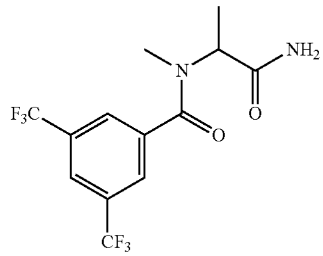 [SMILES: CC(C(N)=O)N(C)C(=O)c1cc(C(F)(F)F)cc(C(F)(F)F)c1] | N-(2-Amino-1-methyl-2-oxo-ethyl)-N-methyl-3,5-bis(trifluoromethyl)benzamide | LCMS: (method 4) Rt 1.27 min, m/z (ES−) 341 [M − H]⁻ | Reaction time: overnight; double amount of T3P® purification by chromatography |
| 40 | 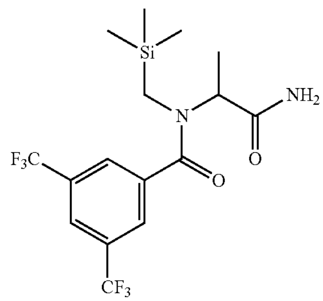 [SMILES: CC(C(N)=O)N(C[Si](C)(C)C)C(=O)c1cc(C(F)(F)F)cc(C(F)(F)F)c1] | N-(2-Amino-1-methyl-2-oxo-ethyl)-3,5-bis(trifluoromethyl)-N-(trimethylsilylmethyl)benzamide | LCMS: (method 4) Rt 1.97 min, m/z (ES−) 413 [M − H]⁻ | Reaction time: overnight; purification by chromatography |

PREPARATION 41

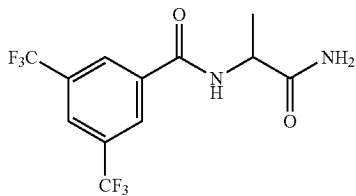 [SMILES: CC(NC(=O)c1cc(C(F)(F)F)cc(C(F)(F)F)c1)C(N)=O]

N-(2-Amino-1-methyl-2-oxo-ethyl)-3,5-bis(trifluoromethyl)benzamide

Add DIPEA (587 mg) to a solution of 2-aminopropanamide (661 mg) and 3,5-bis(trifluoromethyl)benzoic acid (387 mg) in DMF (7 mL). Add T3P® (≥50 wt. % in EtOAc, 1.79 mL) and stir at r.t. overnight. Concentrate under reduced pressure, partition between water and EtOAc, separate the layers, wash the organic phase with NaHCO₃ (aq. sat.) and NaCl (aq. sat.). Dry the organic phase over Na₂SO₄, filter, concentrate under reduced pressure to provide N-(2-amino-1-methyl-2-oxo-ethyl)-3,5-bis(trifluoromethyl)benzamide (387 mg, 79° 6). LCMS (method 4): $R_t$ 1.27 min, m/z (ES−)=327 [M−H]⁻.

PREPARATION 42

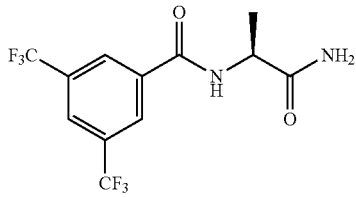 [SMILES: C[C@H](NC(=O)c1cc(C(F)(F)F)cc(C(F)(F)F)c1)C(N)=O]

N-[(1S)-2-amino-1-methyl-2-oxo-ethyl]-3,5-bis(trifluoromethyl)benzamide

Add DIPEA (0.5 mL) to a solution of L-alaninamide (263 mg) and 3,5-bis(trifluoromethyl)benzoic acid (250 mg) in DMF (4 mL). Add T3P® (≥50 wt. % in EtOAc, 1.0 mL) and stir at r.t. overnight. Concentrate under reduced pressure, partition between water and EtOAc, separate the layers, wash the organic phase with NaHCO₃ (aq. sat.) and NaCl (aq. sat.). Dry the organic phase over MgSO₄, filter, concentrate under reduced pressure to provide N-[(1S)-2-amino-1-methyl-2-oxo-ethyl]-3,5-bis(trifluoromethyl)benzamide (299 mg, 94%). LCMS (method 4): $R_t$ 1.26 min, m/z (ES+)=329 [M+H]⁺.

PREPARATION 43

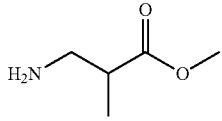

Methyl 3-amino-2-methyl-propanoate

Add thionyl chloride (1.41 mL) to a solution of 3-amino-2-methyl-propanoic acid (87% purity, 1.15 g) in MeOH (10 mL) and stir at r.t. overnight. Evaporate the solvent to provide methyl 3-amino-2-methyl-propanoate (1.13 g, 100%). ¹H NMR (400 MHz, CDCl₃) δ ppm 1.35 (3 H, d, J 7.3 Hz), 2.95-3.36 (3 H, m), 3.80 (3 H, s), 8.46 (2 H, br s).

PREPARATION 44

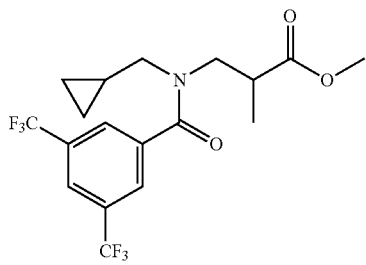 [SMILES: COC(=O)C(C)CN(CC1CC1)C(=O)c1cc(C(F)(F)F)cc(C(F)(F)F)c1]

Methyl 3-[3,5-bis(trifluoromethyl)benzoyl]-(cyclopropylmethyl)amino-2-methyl-propanoate Add methyl 3-amino-2-methyl-propanoate (1.13 g) to a mixture of cyclopropanecarboxaldehyde (867 µL) and Na$_2$SO$_4$ (13.8 g) in AcOH (10 mL) and stir at r.t. for 20 min. Add NaBH(OAc)$_3$ (6.16 g) and stir for 4 h. Partition between NaHCO$_3$ (aq. sat.) and EtOAc, adjusting the pH of the aqueous phase to >10 with NaOH (aq. 2 M), separate the layers, wash the organic phase with NaCl (aq. sat.), dry over Na$_2$SO$_4$, filter and concentrate under reduced pressure to provide methyl 3-(cyclopropylmethylamino)-2-methyl-propanoate. Dissolve the residue and 3,5-bis(trifluoromethyl) benzoic acid (3.73 g) in EtOAc (30 mL), add T3P® (≥50 wt. % in EtOAc, 11.7 mL) and DIPEA (7.56 mL) and stir at 90° C. for 3 h. Partition between NaHCO$_3$ (aq. sat.) and EtOAc, separate the layers and extract the aqueous phase three times with EtOAc. Dry the combined organic extracts over Na$_2$SO$_4$, filter, concentrate under reduced pressure and purify the residue by chromatography to provide methyl 3-[[3,5-bis(trifluoromethyl)benzoyl]-(cyclopropylmethyl) amino]-2-methyl-propanoate (100 mg, 2%). LCMS (method 1): R$_t$ 2.75 min, m/z (ES+)=412 [M+H]$^+$.

PREPARATION 45

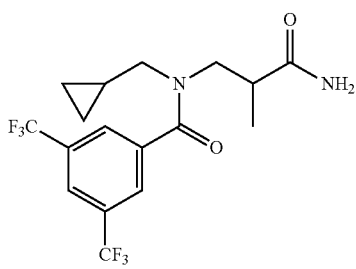 [SMILES: CC(CN(CC1CC1)C(=O)c1cc(C(F)(F)F)cc(C(F)(F)F)c1)C(N)=O]

N-(3-Amino-2-methyl-3-oxo-propyl)-N-(cyclopropylmethyl)-3,5-bis(trifluoromethyl)benzamide Add Mg$_3$N$_2$ (123 mg) to a solution of methyl 3-[[3,5-bis(trifluoromethyl)benzoyl]-(cyclopropylmethyl)amino]-2-methyl-propanoate (100 mg) in MeOH (2.3 mL) at 0° C. and stir in a sealed tube for 1 h. Heat to 80° C. and stir for 4 days. Partition between water and CHCl$_3$, separate the layers, wash the organic phase with HCl (aq. 2 M), extract the aqueous phase three times with CHCl$_3$, dry the combined organic extracts over Na$_2$SO$_4$, filter and concentrate under reduced pressure to provide N-(3-amino-2-methyl-3-oxo-propyl)-N-(cyclopropylmethyl)-3,5-bis(trifluoromethyl) benzamide (55 mg, 57%). LCMS (method 1): R$_t$ 2.42 min. m/z (ES+)=397 [M+H]$^+$.

PREPARATION 46

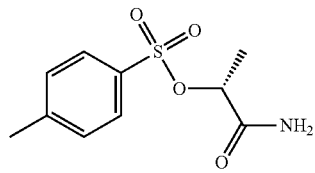 [SMILES: Cc1ccc(S(=O)(=O)O[C@H](C)C(N)=O)cc1]

[(1R)-2-Amino-1-methyl-2-oxo-ethyl]4-methylbenzenesulfonate

Add p-toluene sulfonyl chloride (154 g) and DIPEA (113 mL) to (R)-(+)-lactamide (48.1 g) in CH$_2$Cl$_2$ (1.3 L) at 0° C., warm to r.t. and stir for 3 days. Concentrate under reduced pressure, partition between NaHCO$_3$ (aq. sat.) and EtOAc, separate the layers, dry the organic phase over MgSO$_4$, filter, concentrate under reduced pressure and dissolve the residue in CH$_2$Cl$_2$. Add pentane, filter the precipitate and partition again between NaHCO$_3$ (aq. sat.) and EtOAc, separate the layers, dry the organic phase over MgSO$_4$, filter, concentrate under reduced pressure to provide [(1R)-2-amino-1-methyl-2-oxo-ethyl]4-methylbenzenesulfonate (69.7 g, 48%). $^1$H NMR (400 MHz, DMSO-d$_6$) δ ppm 1.31 (3 H, d, J 6.9 Hz), 2.43 (3 H, s), 4.70 (1 H, q, J 6.9 Hz), 7.29 (1 H, br s), 7.43-7.54 (2 H, m), 7.80-7.85 (2 H, m).

PREPARATION 47

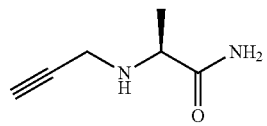

(2S)-2-(Prop-2-ynylamino)propanamide

Mix propargylamine (240 µL), [(1R)-2-amino-1-methyl-2-oxo-ethyl]4-methylbenzenesulfonate (493 mg) and K₂CO₃ (790 mg) in acetonitrile (10 mL) and stir at 30° C. for 3 days. Filter through Celite® and wash with acetonitrile. Concentrate under reduced pressure and purify the residue by chromatography to provide (2S)-2-(prop-2-ynylamino) propanamide (49 mg, 21%). ¹H NMR (400 MHz, CDCl₃) δ ppm 1.37 (3 H, d, J 7.3 Hz,), 1.75 (1 H, br s), 2.24 (1 H, t, J 2.6 Hz), 3.36 (1 H, dd, J 17.2, 2.6 Hz), 3.42 (1 H, q, J 6.9 Hz) 3.49 (1 H, dd, J 17.2, 2.6 Hz), 5.48 (1 H, br s), 6.95 (1 H, br s).

PREPARATION 48

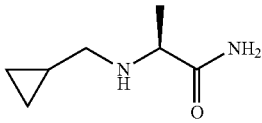

(2S)-2-(Cydopropylmethylamino)propanamide

Mix cyclopropylmethanamine (44 mL), [(1R)-2-amino-1-methyl-2-oxo-ethyl]4-methylbenzenesulfonate (69.3 g) and K₂CO₃ (107 g) in acetonitrile (700 mL) and stir at 30° C. for 6 h. Cool to r.t., filter through Celite® and wash with acetonitrile. Concentrate the filtrate under reduced pressure and purify the residue by chromatography to provide (2S)-2-(cyclopropylmethylamino)propanamide (29.7 g, 81%). ¹H NMR (400 MHz, CDCl₃) δ ppm 0.09-0.18 (2 H, m), 0.44-0.57 (2 H, m), 0.87-0.98 (1 H, m), 1.35 (3 H, d, 0.16.9 Hz), 1.60 (1 H, br s), 2.40 (1 H, dd, J 12.1, 7.3 Hz), 2.54 (1 H, dd, J 12.1, 6.6 Hz), 3.21 (1 H, q, J 6.9 Hz), 5.31 (1 H, br s), 7.14 (1 H, br s).

PREPARATION 49

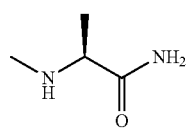

(2S)-2-(Methylamino)propanamide

Mix methylamine (2 M in THF, 1.0 mL), [(1R)-2-amino-1-methyl-2-oxo-ethyl]4-methylbenzenesulfonate (243 mg) and K₂CO₃ (419 mg) in acetonitrile (1 mL) and stir at r.t. for 3 days. Filter through Celite® and wash with acetonitrile. Concentrate the filtrate under reduced pressure to provide (2S)-2-(methylamino)propanamide (50% w, 46 mg, 22%). ¹H NMR (400 MHz, DMSO-d₆) δ ppm 1.09 (3 H, d, J 6.94 Hz), 1.84 (1 H, br s), 2.19 (3 H, s), 2.86 (1 H, q, J 6.81 Hz), 6.94 (1 H, br s), 7.25 (1 H, br s).

PREPARATION 50

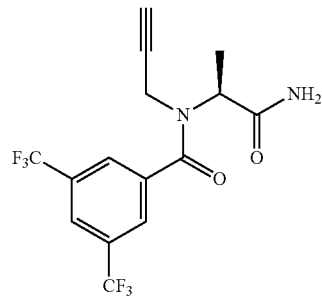 [SMILES: C#CCN(C(=O)c1cc(C(F)(F)F)cc(C(F)(F)F)c1)[C@@H](C)C(N)=O]

N-[(1S)-2-Amino-1-methyl-2-ozo-ethyl]-N-prop-2-ynyl-3,5-bis(trifluoromethyl)benzamide Add T3P® (≥50 wt. % in EtOAc, 350 μL) and 3,5-bis(trifluoromethyl)benzoic acid (120 mg) to a solution of DIPEA (200 μL) and (2S)-2-(prop-2-ynylamino)propanamide (49 mg) in EtOAc (1.0 mL) and stir at r.t. overnight. Partition between water and EtOAc, separate the layers, wash the organic phase with water, NH₄Cl (aq. sat.) and NaOH (aq. 1 M). Dry the organic phase over MgSO₄, filter, concentrate under reduced pressure and purify the residue by chromatography to provide N-[(1S)-2-amino-1-methyl-2-oxo-ethyl]-N-prop-2-ynyl-3,5-bis(trifluoromethyl)benzamide (58 mg, 38%). LCMS: (method 4) R$_t$ 1.48 min, m/z (ES−) 365 [M−H]⁻.

PREPARATION 51

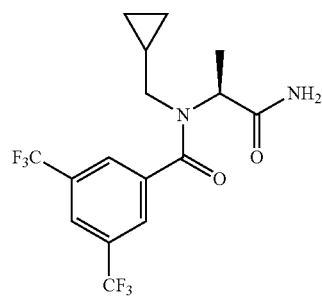 [SMILES: C[C@@H](C(N)=O)N(CC1CC1)C(=O)c1cc(C(F)(F)F)cc(C(F)(F)F)c1]

N-[(1S)-2-Amino-1-methyl-2-oxo-ethyl]-N-(cyclopropylmethyl)-3,5-bis(trifluoromethyl)benzamide Add T3P® (≥50 wt. % in EtOAc, 185 mL) and 3,5-bis(trifluoromethyl)benzoic acid (64.3 g) to a solution of DIPEA (109 mL) and (2S)-2-(cyclopropylmethylamino)propanamide (29.5 g) in EtOAc (590 mL) and stir at r.t. overnight. Partition between water and EtOAc, separate the layers, wash the organic phase with water, NH₄Cl (aq. sat.) and NaOH (aq. 1 M). Dry the organic phase over MgSO₄, filter, concentrate under reduced pressure and purify the residue by precipitation from CH₂Cl₂ and pentane to provide N-[(1S)-2-amino-1-methyl-2-oxo-ethyl]-N-(cyclopropylmethyl)-3,5-bis(trifluoromethyl)benzamide (49.1 g, 62%). LCMS: (method 4) R$_t$ 1.61 min, m/z (ES+) 383 [M+H]⁺.

The compound of Preparation 52 set forth in table 4 may be prepared essentially as described in Preparation 51.

TABLE 4

| Prep. | Structure | Compound | Analytical data | Remarks |
|---|---|---|---|---|
| 52 | 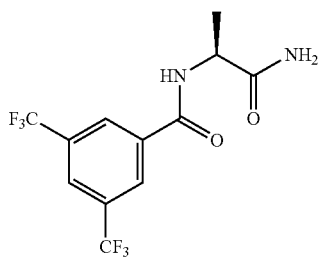 | N-[(1S)-2-Amino-1-methyl-2-oxo-ethyl]-N-methyl-3,5-bis(trifluoromethyl)benzamide | LCMS: (method 4) $R_t$ 1.28 min, m/z (ES−) 341 [M − H]⁻ | 1 eq. of carboxylic acid and 1.5 eq. of T3P ®; purification by chromatography |

PREPARATION 53

N-[(1S)-2-amino-1-methyl-2-oxo-ethyl]-3,5-bis(trifluoromethyl)benzamide

Add 3,5-bis(trifluoromethyl)benzoic acid (900 mg) and T3P® (≥50 wt. % in EtOAc, 4.2 mL) to a mixture of L-alaninamide (1.25 g) and DIPEA (1.9 mL) in DMF (15 mL). Stir at r.t. overnight. Partition between water and EtOAc, separate the layers, wash the organic phase NaHCO₃ (aq. sat.) and NaCl (aq. sat.). Dry the organic phase over MgSO₄, filter, concentrate under reduced pressure to provide N-[(1S)-2-amino-1-methyl-2-oxo-ethyl]-3,5-bis(trifluoromethyl)benzamide (1.05 g, 92%). LCMS: (method 4) $R_t$ 1.27 min, m/z (ES+) 329 [M+H]⁺.

The compound of Preparation 54 set forth in table 5 may be prepared essentially as described in Preparation 53.

EXAMPLE 34

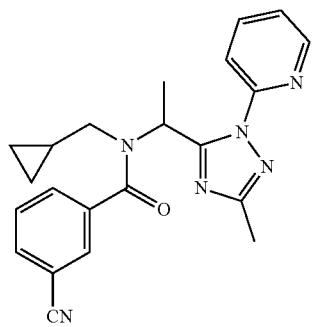 [SMILES: Cc1nc(C(C)N(CC2CC2)C(=O)c2cccc(C#N)c2)n(-c2ccccn2)n1]

3-Cyano-N-(cyclopropylmethyl)-N-[1-[5-methyl-2-(2-pyridyl)-1,2,4-triazol-3-yl]ethyl]benzamide Add N,N-dimethylacetamide dimethylacetal (88 μL) to a solution of N-(2-amino-1-methyl-2-oxo-ethyl)-3-cyano-N-(cyclopropylmethyl)benzamide (108 mg) in CH₂Cl₂ (3.0 mL) and stir at reflux for 1 h. Cool to r.t., concentrate under reduced pressure, dissolve the residue in 1,4-dioxane/AcOH (1 mL/1 mL), add 2-hydrazinopyridine (87 mg) and stir at 90° C. for 2 h. Cool to r.t., concentrate under reduced pressure, partition the residue between water and EtOAc. Separate the layers, wash the organic phase with NaHCO₃ (aq. sat.). Extract the combined aqueous phases twice with

TABLE 5

| Prep. | Structure | Compound | Analytical data | Remarks |
|---|---|---|---|---|
| 54 | 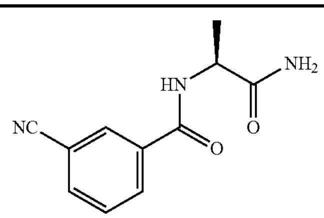 | N-[(1S)-2-amino-1-methyl-2-oxo-ethyl]-3-cyano-benzamide | LCMS: (method 4) $R_t$ 0.39 min, m/z (ES+) 218 [M + H]⁺ | 3 eq. of L-alaninamide |

EtOAc, wash the combined organic extracts with NaCl (aq. sat.), dry over MgSO$_4$, filter, concentrate under reduced pressure and purify the residue by chromatography to provide 3-cyano-N-(cyclopropylmethyl)-N-[1-[5-methyl-2-(2-pyridyl)-1,2,4-triazol-3-yl]ethyl]benzamide (104 mg, 68%). LCMS (method 3): R$_t$ 2.66 min, m/z (ES+)=387 [M+H]$^+$.

The compound of Example 61 set forth in table 6 may be prepared essentially as described in Example 34.

TABLE 6

| Example | Structure | Compound | Analytical data | Remarks |
|---|---|---|---|---|
| 61 | 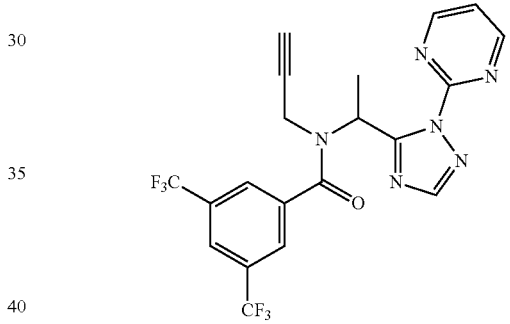 | N-(Cyclopropylmethyl)-N-[1-(5-methyl-2-pyrimidin-2-yl-1,2,4-triazol-3-yl)ethyl]-3,5-bis(trifluoromethyl)benzamide | LCMS: (method 4) R$_t$ 1.80 min, m/z (ES+) 499 [M + H]$^+$ | 2$^{nd}$ step: Reaction time: 16 h; T = 50° C. |

EXAMPLE 35

N-Prop-2-ynyl-N-[1-(2-pyrimidin-2-yl-1,2,4-triazol-3-yl)ethyl]-3,5-bis(trifluoromethyl)benzamide Add N,N-dimethylamide dimethylacetal (2.8 mL) to a solution of N-(2-amino-1-methyl-2-oxo-ethyl)-N-prop-2-ynyl-3,5-bis(trifluoromethyl)benzamide (5.00 g) in CH$_2$Cl$_2$ (70 mL) and stir at reflux for 2 h. Cool to r.t., concentrate under reduced pressure, dissolve the residue in 1,4-dioxane/AcOH (80 mL/8 mL), add 2-hydrazinopyrimidine (2.48 g) and stir at 50° C. overnight. Cool to r.t., concentrate under reduced pressure, partition the residue between NaHCO$_3$ (aq. sat.) and EtOAc. Separate the layers, extract the aqueous phase three times with EtOAc, dry the combined organic extracts over MgSO$_4$, filter, concentrate under reduced pressure and purify the residue by chromatography to provide N-prop-2-ynyl-N-[1-(2-pyrimidin-2-yl-1,2,4-triazol-3-yl)ethyl]-3,5-bis(trifluoromethyl)benzamide (2.97 g, 46%). LCMS (method 2): R$_t$ 1.52 min, m/z (ES+)=469 [M+H]$^+$. Chiral HPLC: column Chiralpak AD-H (250×4.6 mm), heptane/iPrOH/diethylamine 95:5:0.1, flow rate 1 mL/min, r.t., λ 240 nm. R$_t$ 13.8 and 16.6 min.

The compound of Example 36 set forth in table 7 may be prepared essentially as described in Example 35.

TABLE 7

| Example | Structure | Compound | Analytical data | Remarks |
|---------|-----------|----------|-----------------|---------|
| 36 | 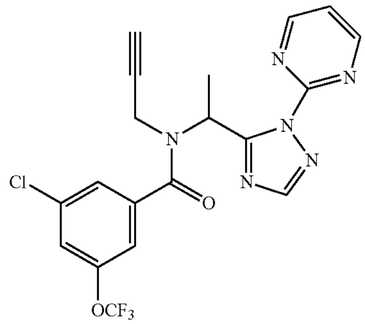 [SMILES: C#CCN(C(=O)c1cc(Cl)cc(OC(F)(F)F)c1)C(C)c1ncnn1-c1ncccn1] | 3-Chloro-N-prop-2-ynyl-N-[1-(2-pyrimidin-2-yl-1,2,4-triazol-3-yl)ethyl]-5-(trifluoromethoxy)-benzamide | LCMS: (method 2) $R_t$ 1.49 min, m/z (ES+) 451 [M + H]$^+$ | 2$^{nd}$ step: Reaction time: 1 h; T = 90° C. |

EXAMPLE 37

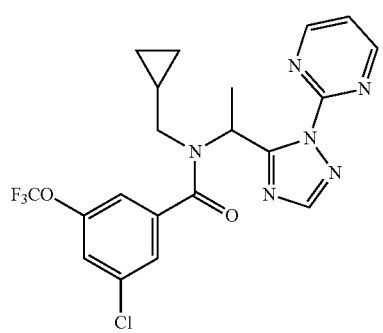 [SMILES: CC(c1ncnn1-c1ncccn1)N(CC1CC1)C(=O)c1cc(Cl)cc(OC(F)(F)F)c1]

3-chloro-N-(cyclopropylmethyl)-N-[1-(2-pyrimidin-2-yl-1,2,4-triazol-3-yl)ethyl]-5-(trifluoromethoxy)benzamide Add N,N-dimethylamide dimethylacetal (60 µL) to a solution of N-(2-amino-1-methyl-2-oxo-ethyl)-3-chloro-N-(cyclopropylmethyl)-5-(trifluoromethoxy)-benzamide (106 mg) in CH$_2$Cl$_2$ (5 mL) and stir at reflux for 1 h. Cool to r.t., concentrate under reduced pressure, dissolve the residue in 1,4-dioxane/AcOH (1.5 mL/1.5 mL), add 2-hydrazinopyrimidine (48 mg) and stir at 90° C. for 1 h. Cool to r.t., concentrate under reduced pressure, partition the residue between NaHCO$_3$ (aq. sat.) and CH$_2$Cl$_2$. Separate the layers, extract the aqueous phase three times with CH$_2$Cl$_2$, dry the combined organic extracts over Na$_2$SO$_4$, filter, concentrate under reduced pressure and purify the residue by chromatography to provide 3-chloro-N-(cyclopropylmethyl)-N-[1-(2-pyrimidin-2-yl-1,2,4-triazol-3-yl)ethyl]-5-(trifluoromethoxy)benzamide (101 mg, 59%). LCMS (method 2): $R_t$ 1.64 min, m/z (ES+)=467 [M+H]$^+$.

The compounds of Examples 38-45 and 62-69 set forth in table 8 may be prepared essentially as described in Example 37.

TABLE 8

| Example | Structure | Compound | Analytical data | Remarks |
|---------|-----------|----------|-----------------|---------|
| 38 | 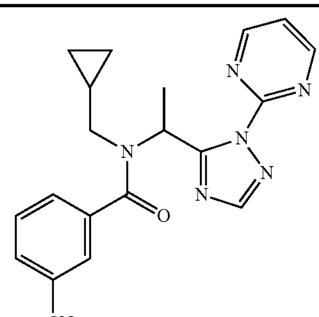 | 3-Cyano-N-(cyclopropylmethyl)-N-[1-(2-pyrimidin-2-yl-1,2,4-triazol-3-yl)ethyl]benzamide | LCMS: (method 2) $R_t$ 1.11 min, m/z (ES+) 374 [M + H]$^+$ | Reaction time: overnight; T = 80° C. |
| 39 | 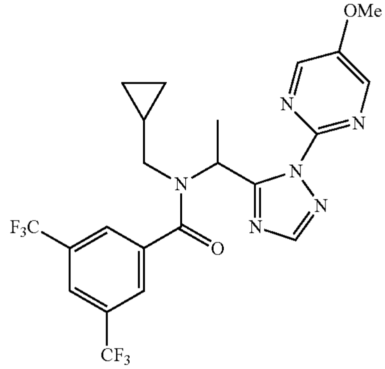 [SMILES: COc1cnc(-n2ncnc2C(C)N(CC2CC2)C(=O)c2cc(C(F)(F)F)cc(C(F)(F)F)c2)nc1] | N-(Cyclopropylmethyl)-N-[1-[2-(5-methoxypyrimidin-2-yl)-1,2,4-triazol-3-yl]ethyl]-3,5-bis(trifluoromethyl)benzamide | LCMS: (method 2) $R_t$ 1.71 min, m/z (ES+) 515 [M + H]$^+$ | — |

TABLE 8-continued

| Example | Structure | Compound | Analytical data | Remarks |
|---|---|---|---|---|
| 40 | 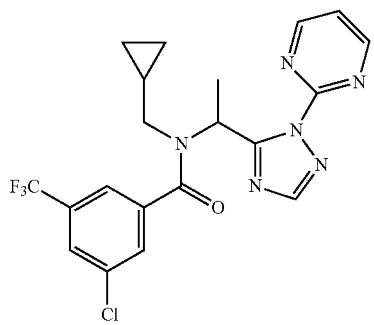 [SMILES: CC(c1ncnn1-c1ncccn1)N(CC1CC1)C(=O)c1cc(Cl)cc(C(F)(F)F)c1] | 3-Chloro-N-(cyclopropylmethyl)-N-[1-(2-pyrimidin-2-yl-1,2,4-triazol-3-yl)ethyl]-5-(trifluoromethyl)benzamide | LCMS: (method 2) R$_t$ 1.59 min, m/z (ES+) 451 [M + H]$^+$ | — |
| 41 | 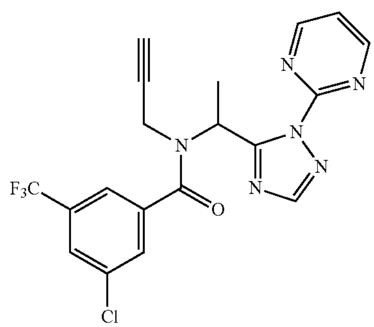 [SMILES: C#CCN(C(=O)c1cc(Cl)cc(C(F)(F)F)c1)C(C)c1ncnn1-c1ncccn1] | 3-Chloro-N-prop-2-ynyl-N-[1-(2-pyrimidin-2-yl-1,2,4-triazol-3-yl)ethyl]-5-(trifluoromethyl)benzamide | LCMS: (method 2) R$_t$ 1.45 min, m/z (ES+) 435 [M + H]$^+$ | — |
| 42 | 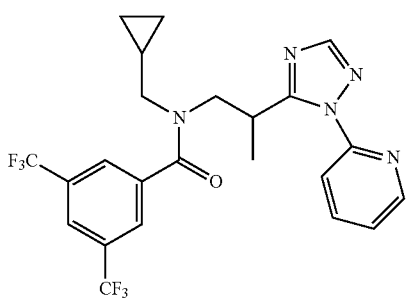 [SMILES: CC(CN(CC1CC1)C(=O)c1cc(C(F)(F)F)cc(C(F)(F)F)c1)c1ncnn1-c1ccccn1] | 3-(Cyclopropylmethyl)-N-[2-[2-(2-pyridyl)-1,2,4-triazol-3-yl]propyl]-3,5-bis(trifluoromethyl)benzamide | LCMS: (method 1) R$_t$ 2.72 min, m/z (ES+) 498 [M + H]$^+$ | Reaction time: overnight; T = 80° C. |
| 43 | 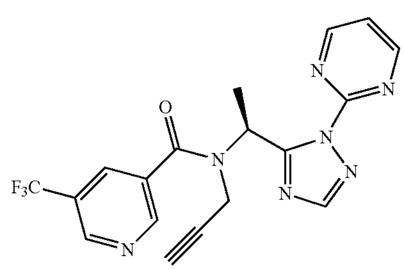 [SMILES: C#CCN(C(=O)c1cncc(C(F)(F)F)c1)[C@@H](C)c1ncnn1-c1ncccn1] | N-Prop-2-ynyl-N-[(1S)-1-(2-pyrimidin-2-yl-1,2,4-triazol-3-yl)ethyl]-5-(trifluoromethyl)pyridine-3-carboxamide | LCMS: (method 4) R$_t$ 0.67 min, m/z (ES+) 402 [M + H]$^+$ | Reaction time: overnight |
| 44 | 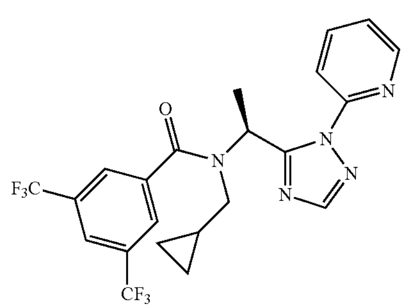 [SMILES: C[C@@H](c1ncnn1-c1ccccn1)N(CC1CC1)C(=O)c1cc(C(F)(F)F)cc(C(F)(F)F)c1] | N-(Cyclopropylmethyl)-N-[(1S)-1-[2-(2-pyridyl)-1,2,4-triazol-3-yl]ethyl]-3,5-bis(trifluoromethyl)benzamide | LCMS: (method 4) R$_t$ 2.05 min, m/z (ES+) 484 [M + H]$^+$ | Reaction time: overnight |

TABLE 8-continued

| Example | Structure | Compound | Analytical data | Remarks |
|---|---|---|---|---|
| 45 | 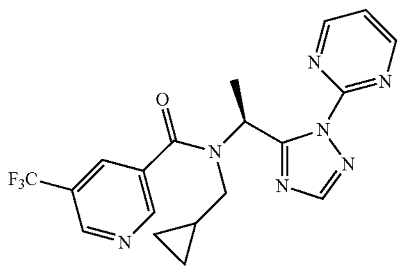 [SMILES: C[C@@H](c1ncnn1-c1ncccn1)N(CC1CC1)C(=O)c1cncc(C(F)(F)F)c1] | N-(Cyclopropylmethyl)-N-[(1S)-1-(2-pyrimidin-2-yl-1,2,4-triazol-3-yl)ethyl]-5-(trifluoromethyl)pyridine-3-carboxamide | LCMS: (method 4) $R_t$ 0.93 min, m/z (ES+) 418 [M + H]$^+$ | Reaction time: overnight |
| 62 | 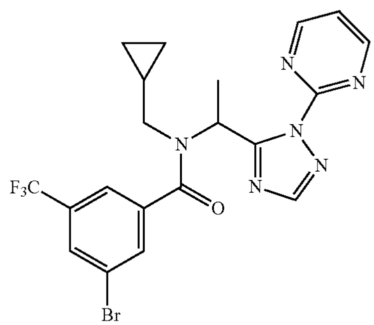 [SMILES: CC(c1ncnn1-c1ncccn1)N(CC1CC1)C(=O)c1cc(Br)cc(C(F)(F)F)c1] | 3-Bromo-N-(cyclopropylmethyl)-N-[1-(2-pyrimidin-2-yl-1,2,4-triazol-3-yl)ethyl]-5-(trifluoromethyl)benzamide | LCMS: (method 4) Rt 1.74 min, m/z (ES+) 495 [M + H]$^+$ | 2nd step: T = 50° C. |
| 63 | 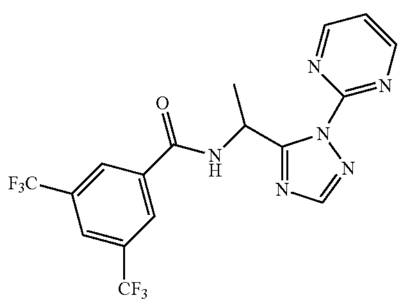 [SMILES: CC(NC(=O)c1cc(C(F)(F)F)cc(C(F)(F)F)c1)c1ncnn1-c1ncccn1] | N-[1-(2-Pyrimidin-2-yl-1,2,4-triazol-3-yl)ethyl]-3,5-bis(trifluoromethyl)benzamide | LCMS: (method 4) Rt 1.53 min, m/z (ES+) 431 [M + H]$^+$ | Reaction time 2nd step: overnight T = 50° C. |
| 64 | 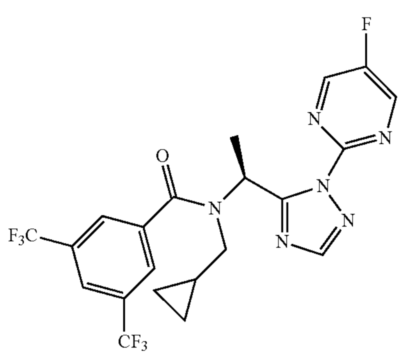 [SMILES: C[C@@H](c1ncnn1-c1ncc(F)cn1)N(CC1CC1)C(=O)c1cc(C(F)(F)F)cc(C(F)(F)F)c1] | N-(Cyclopropylmethyl)-N-[(1S)-1-[2-(5-fluoropyrimidin-2-yl)-1,2,4-triazol-3-yl]ethyl]-3,5-bis(trifluoromethyl)benzamide | LCMS: (method 4) Rt 1.93 min, m/z (ES+) 503 [M + H]$^+$ | Reaction time 2nd step: overnight T = 50° C. |
| 65 | 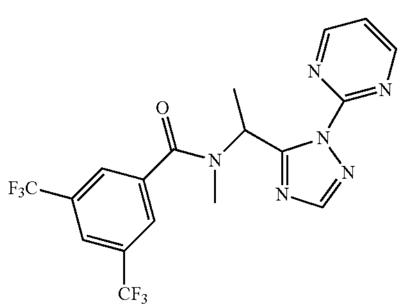 [SMILES: CC(c1ncnn1-c1ncccn1)N(C)C(=O)c1cc(C(F)(F)F)cc(C(F)(F)F)c1] | N-Methyl-N-[1-(2-pyrimidin-2-yl-1,2,4-triazol-3-yl)ethyl]-3,5-bis(trifluoromethyl)benzamide | LCMS: (method 4) Rt 1.49 min, m/z (ES+) 445 [M + H]$^+$ | Reaction time 2nd step: overnight T = 50° C. |

TABLE 8-continued

| Example | Structure | Compound | Analytical data | Remarks |
|---|---|---|---|---|
| 66 | 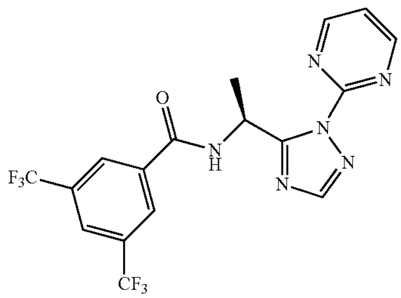 [SMILES: C[C@H](NC(=O)c1cc(C(F)(F)F)cc(C(F)(F)F)c1)c1ncnn1-c1ncccn1] | N-[(1S)-1-(2-Pyrimidin-2-yl-1,2,4-triazol-3-yl)ethyl]-3,5-bis(trifluoromethyl)benzamide | LCMS: (method 4) Rt 1.53 min, m/z (ES+) 431 [M + H]+ | Reaction time 2nd step: overnight T = 50° C. |
| 67 | 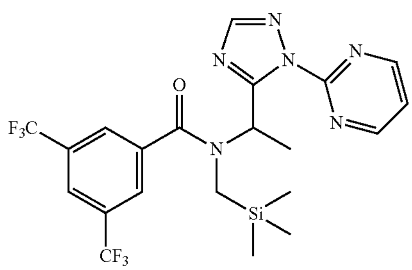 [SMILES: CC(c1ncnn1-c1ncccn1)N(C[Si](C)(C)C)C(=O)c1cc(C(F)(F)F)cc(C(F)(F)F)c1] | N-[1-(2-pyrimidin-2-yl-1,2,4-triazol-3-yl)ethyl]-3,5-bis(trifluoromethyl)-N-(trimethylsilylmethyl)benzamide | LCMS: (method 4) Rt 2.19 min, m/z (ES+) 517 [M + H]+ | Reaction time 2nd step: overnight T = 50° C. |
| 68 | 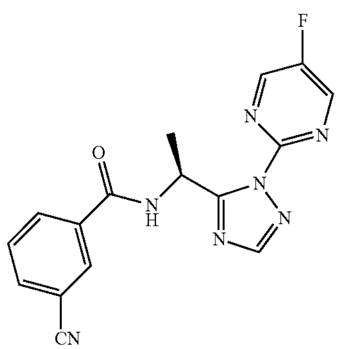 [SMILES: C[C@H](NC(=O)c1cccc(C#N)c1)c1ncnn1-c1ncc(F)cn1] | 3-Cyano-N-[(1S)-1-[2-(5-fluoropyrimidin-2-yl)-1,2,4-triazol-3-yl]ethyl]benzamide | LCMS: (method 4) Rt 0.57 min, m/z (ES+) 338 [M + H]+ | Reaction time 2nd step: overnight T = 50° C. |
| 69 | 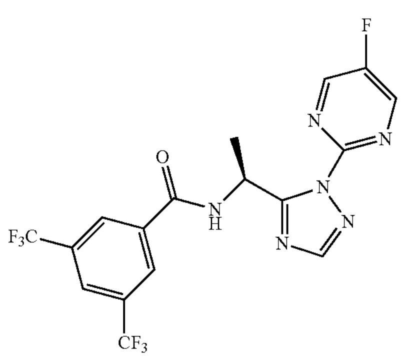 [SMILES: C[C@H](NC(=O)c1cc(C(F)(F)F)cc(C(F)(F)F)c1)c1ncnn1-c1ncc(F)cn1] | N-[(1S)-1-[2-(5-Fluoropyrimidin-2-yl)-1,2,4-triazol-3-yl]ethyl]-3,5-bis(trifluoromethyl)benzamide | LCMS: (method 4) Rt 1.67 min, m/z (ES+) 449 [M + H]+ | Reaction time 2nd step: overnight T = 50° C. |

EXAMPLE 46

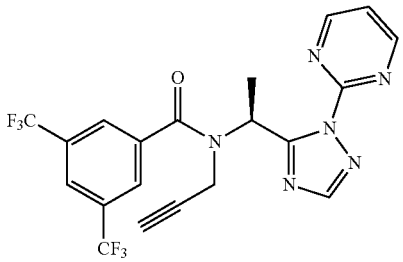 [SMILES: C#CCN(C(=O)c1cc(C(F)(F)F)cc(C(F)(F)F)c1)[C@@H](C)c1ncnn1-c1ncccn1]

N-Prop-2-ynyl-N-[(1S)-1-(2-pyrimidin-2-yl-1,2,4-triazol-3-yl)ethyl]-3,5-bis(trifluoromethyl)benzamide Add N,N-dimethylamide dimethylacetal (32 µL) to a solution of N-[(1S)-2-amino-1-methyl-2-oxo-ethyl]-N-prop-2-ynyl-3,5-bis(trifluoromethyl)benzamide (58 mg) in CH₂Cl₂ (0.7 mL) and stir at reflux for 1 h. Cool to r.t., concentrate under reduced pressure, dissolve the residue in 1,4-dioxane/AcOH (0.7 mL/0.7 mL), add 2-hydrazinopyrimidine (23 mg) and stir at 50° C. overnight. Cool to r.t., concentrate under reduced pressure, partition the residue between NaHCO₃ (aq. sat.) and EtOAc. Separate the layers, dry the organic phase over MgSO₄, filter, concentrate under reduced pressure and purify the residue by chromatography to provide N-prop-2-ynyl-N-[(1S)-1-(2-pyrimidin-2-yl-1,2,4-triazol-3-yl)ethyl]-3,5-bis(trifluoromethyl)benzamide (38 mg, 58%). LCMS: (method 4) $R_t$ 1.59 min, n/z (ES) 469 [M+H]⁺. Chiral HPLC: column Chiralpak AD-H (250×4.6 mm), heptane/iPrOH/diethylamine 95:5:0.1, flow rate 1 mL/min, r.t.,λ240 nm, $R_t$ 14.1 min, ee >99%.

EXAMPLE 47

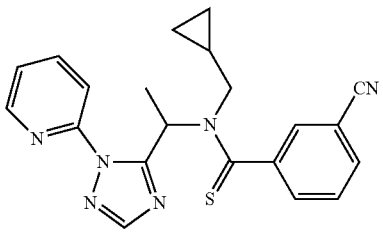 [SMILES: CC(c1ncnn1-c1ccccn1)N(CC1CC1)C(=S)c1cccc(C#N)c1]

3-Cyano-N-(cyclopropylmethyl)-N-[1-[2-(2-pyridyl)-1,2,4-triazol-3-yl]ethyl]benzenecarbothioamide (i) 3-Cyano-N-(cyclopropylmethyl)-N-[1-[2-(2-pyridyl)-1,2,4-triazol-3-yl]ethyl]benzamide Add 3-cyanobenzoic acid (81 mg) to a solution of N-(cyclopropylmethyl)-1-[2-(2-pyridyl)-1,2,4-triazol-3-yl]ethanamine (60 mg) and DIPEA (287 µL) in EtOAc (6 mL) and stir the mixture at r.t. for 10 min. Add T3P® (≥50 wt. % in EtOAc, 534 µL) and stir at r.t. overnight. Partition the mixture between water and EtOAc, separate the layers and wash the organic phase sequentially with water. NaHCO₃ (aq. sat.) and NH₄Cl (aq. sat.). Dry over MgSO₄, filter, concentrate under reduced pressure and purify the residue by chromatography to provide 3-cyano-N-(cyclopropylmethyl)-N-[1-[2-(2-pyridyl)-1,2,4-triazol-3-yl]ethyl]benzamide (160 mg, 85%). LCMS (method 1): $R_t$ 2.32 min, m/z (ES+)=373 [M+H]⁺.

(ii) 3-Cyano-N-(cyclopropylmethyl)-N-[1-[2-(2-pyridyl)-1,2,4-triazol-3-yl]ethyl]benzenecarbothioamide Add Lawesson's reagent (191 mg) to a solution of 3-cyano-N-(cyclopropylmethyl)-N-[1-[2-(2-pyridyl)-1,2,4-triazol-3-yl]ethyl]benzamide (160 mg) in toluene (10 mL) and stir at reflux overnight. Cool to r.t., concentrate under reduced pressure and purify the residue by chromatography and trituration with pentane to provide 3-cyano-N-(cyclopropylmethyl)-N-[1-[2-(2-pyridyl)-1,2,4-triazol-3-yl]ethyl]benzenecarbothioamide (145 mg, 87%). LCMS (method 1): $R_t$ 2.58 min, m/z (ES+)=389 [M+H]⁺.

EXAMPLE 70

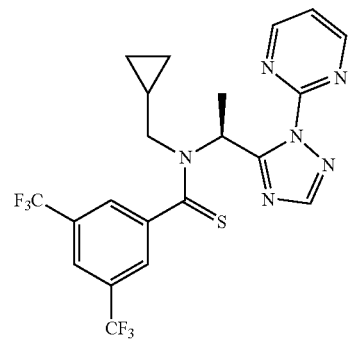 [SMILES: C[C@@H](c1ncnn1-c1ncccn1)N(CC1CC1)C(=S)c1cc(C(F)(F)F)cc(C(F)(F)F)c1]

N-(Cyclopropylmethyl)-N-[1S)-1-(2-pyrimidin-2-yl-1,2,4-triazol-3-yl)ethyl]-3,5-bis(trifluoromethyl)benzenecarbothioamide Add Lawesson's reagent (92 mg) to a solution of N-(cyclopropylmethyl)-N-[(1S)-1-(2-pyrimidin-2-yl-1,2,4-triazol-3-yl)ethyl]-3,5-bis(trifluoromethyl)benzamide (100 mg) in toluene (5 mL) and stir at reflux overnight. Cool to r.t., concentrate under reduced pressure and purify the residue by chromatography and trituration with pentane to provide N-(cyclopropylmethyl)-N-[(1S)-1-(2-pyrimidin-2-yl-1,2,4-triazol-3-yl)ethyl]-3,5-bis(trifluoromethyl)benzenecarbothioamide (61 mg, 59%). LCMS (method 4): $R_t$ 2.19 min, m/z (ES+)=501 [M+H]⁺.

EXAMPLE 71

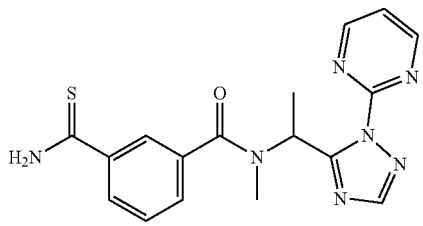 [SMILES: CC(c1ncnn1-c1ncccn1)N(C)C(=O)c1cccc(C(N)=S)c1]

3-Carbamothioyl-N-methyl-N-[1-(2-pyrimidin-2-yl-1,2,4-triazol-3-yl)ethyl]benzamide Add triethylamine (0.1 mL) and ammonium sulfide (aq. 40-48 wt. %, 126 mg) to a solution of 3-cyano-N-methyl-N-[1-(2-pyrimidin-2-yl-1,2,4-triazol-3-yl)ethyl]benzamide (224 mg) in pyridine (2 mL) and stir at 50° C. for 1 h. Cool to r.t., partition the mixture between water and CH₂C₂, separate the layers and dry the organic phase over MgSO₄, filter, concentrate under reduced pressure and purify the residue by chromatography to provide 3-carbamothioyl-N-methyl-N-[1-(2-pyrimidin-2-yl-1,2,4-triazol-3-yl)ethyl]benzamide (62 mg, 24%). LCMS (method 4): $R_t$ 0.41 min. m/z (ES+)=368 [M+H]⁺.

The compound of Example 72 set forth in table 9 may be prepared essentially as described in Example 71.

TABLE 9

| Example | Structure | Compound | Analytical data | Remarks |
|---|---|---|---|---|
| 72 | 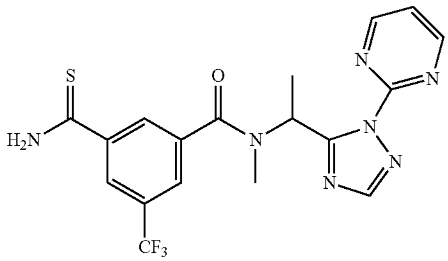 [SMILES: CC(c1ncnn1-c1ncccn1)N(C)C(=O)c1cc(C(N)=S)cc(C(F)(F)F)c1] | 3-Carbamothioyl-N-methyl-N-[1-(2-pyrimidin-2-yl-1,2,4-triazol-3-yl)ethyl]-5-(trifluoromethyl)benzamide | LCMS: (method 4) $R_t$ 0.81 min, m/z (ES+) 436 [M + H]$^+$ | — |

PREPARATION 55

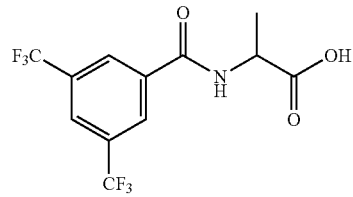

2-[[3,5-Bis(trifluoromethyl)benzoyl]amino]propanoic acid

Add DL-alanine (918 mg) to a solution of NaOH (1.74 g) in water (6.0 mL) and acetonitrile (2.0 mL). Cool the mixture to 0° C., add 3,5-bis(trifluoromethyl)benzoyl chloride (2.0 mL) and stir at 0° C. for 30 min. Warm to r.t. and stir for 2 h. Concentrate under reduced pressure, add HCl (aq. 12 M, 1.0 mL) and filter the resulting solid. Dry the solid under vacuum to provide 2-[[3,5-bis(trifluoromethyl)benzoyl]amino]propanoic acid (3.00 g, 54%). LCMS (method 4): $R_t$ 1.52 min, m/z (ES+)=330 [M+H]$^+$.

EXAMPLE 73

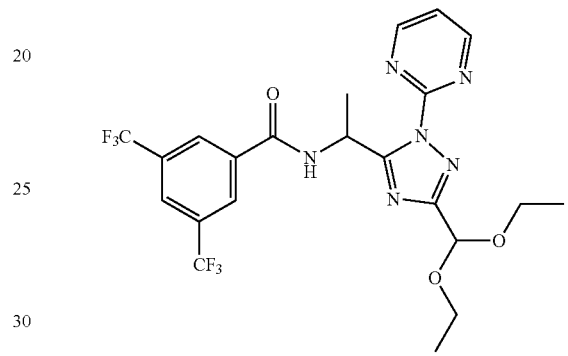

N-[1-[5-(Diethoxymethyl)-2-pyrimidin-2-yl-1,2,4-triazol-3-yl]ethyl]-3,5-bis(trifluoromethyl)benzamide Add N,N-diisopropylamine (3.84 mL) to a mixture of 2,2-diethoxyacetamidine hydrochloride (1.33 g), 2-[[3,5-bis(trifluoromethyl)benzoyl]amino]propanoic acid (3.00 g) and HATU (3.05 g) in DMF (10 mL). Stirr at r.t. for 3 h. Add 2-hydrazinopyrimidine (1.20 g) followed by AcOH (4.18 mL) and stir at 80° C. for 1 h. Cool to r.t. and dilute with EtOAc (50 mL). Wash the organic phase sequentially with NaHCO$_3$ (aq. sat.) and water. Dry the organic phase over MgSO$_4$, filter and concentrate under reduced pressure to provide N-[1-[5-(diethoxymethyl)-2-pyrimidin-2-yl-1,2,4-triazol-3-yl]ethyl]-3,5-bis(trifluoromethyl)benzamide (900 mg, 23%). LCMS (method 4): $R_t$ 1.96 min, m/z (ES−)=531 [M−H]$^-$.

The compound of Example 74 set forth in table 10 may be prepared essentially as described in Example 73.

TABLE 10

| Example | Structure | Compound | Analytical data | Remarks |
|---|---|---|---|---|
| 74 | 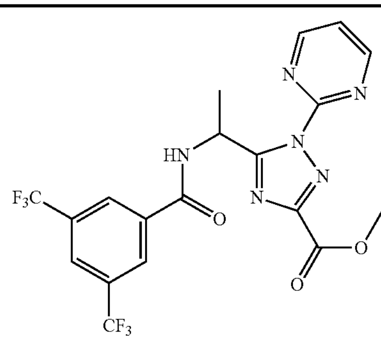 | Methyl 5-[1-[[3,5-bis(trifluoromethyl)benzoyl]amino]ethyl]-1-pyrimidin-2-yl-1,2,4-triazole-3-carboxylate | LCMS: (method 4) $R_t$ 1.80 min, m/z (ES+) 499 [M + H]$^+$ | |

EXAMPLE 48

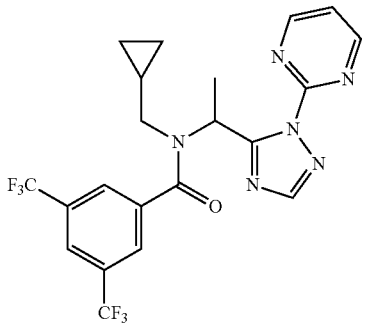 [SMILES: CC(c1ncnn1-c1ncccn1)N(CC1CC1)C(=O)c1cc(C(F)(F)F)cc(C(F)(F)F)c1]

N-(Cyclopropylmethyl)-N-[1-(2-pyrimidin-2-yl-1,2,4-triazol-3-yl)ethyl]-3,5-bis(trifluoromethyl)benzamide (i) 2-(Cyclopropylmethylamino)propanamide Add $K_2CO_3$ (1.45 g) and cyclopropylmethanamine (560 µL) to 2-bromopropanamide (490 mg) and in acetonitrile (8 mL) and stir at 80° C. for 1 h. Cool to r.t., filter through Celite® and wash with acetonitrile. Partition the residue between water and EtOAc, separate the layers and extract the aqueous phase twice with EtOAc. Dry the combined organic extracts over $MgSO_4$, filter and concentrate under reduced pressure to provide 2-(cyclopropylmethylamino)propanamide (351 mg, 77%). $^1$H NMR (400 MHz, $CDCl_3$) δ ppm 0.06-0.23 (2 H, m), 0.44-0.58 (2 H, m), 0.83-1.02 (1 H, m), 1.36 (3 H, d, J 6.9 Hz), 1.73 (1 H, br s), 2.42 (1 H, dd, J 12.4, 6.9 Hz), 2.55 (1 H, dd, J 12.1, 6.6 Hz), 3.24 (1 H, q, J 6.9 Hz), 5.39 (1 H, br s), 7.18 (1 H, br s).

(ii) N-(2-Amino-1-methyl-2-oxo-ethyl)-N-(cyclopropylmethyl)-3,5-bis(trifluoromethyl)benzamide Add T3P® (≥50 wt. % in EtOAc, 6.2 mL) and DIPEA (4 mL) to a mixture of 2-(cyclopropylmethylamino)propanamide (990 mg) and 3,5-bis(trifluoromethyl)benzoic acid (2.02 g) in EtOAc (20 mL) and stir at r.t. overnight. Partition between water and EtOAc, separate the layers, extract the aqueous phase twice with EtOAc. Wash the combined organic extracts with NaCl (aq. sat.), dry over $Na_2SO_4$, filter, concentrate under reduced pressure. Partition the residue between NaOH (aq. 1 M) and $CH_2Cl_2$, separate the layers, extract the aqueous phase three times with $CH_2Cl_2$, dry the combined organic extracts over $Na_2SO_4$, filter, concentrate under reduced pressure to provide N-(2-amino-1-methyl-2-oxo-ethyl)-N-(cyclopropylmethyl)-3,5-bis(trifluoromethyl)benzamide (2.37 g, 78%). LCMS: (method 2) $R_t$ 1.52 min, m/z (ES−)=381 [M−H]−.

(iii) N-(Cyclopropylmethyl)-N-[1-(2-pyrimidin-2-yl-1,2,4-triazol-3-yl)ethyl]-3,5-bis(trifluoromethyl)benzamide Add N,N-dimethylamide dimethylacetal (220 µL) to a solution of N-(2-amino-1-methyl-2-oxo-ethyl)-N-(cyclopropylmethyl)-3,5-bis(trifluoromethyl)benzamide (408 mg) in $CH_2Cl_2$ (5 mL) and stir at reflux for 1.5 h. Cool to r.t., concentrate under reduced pressure, dissolve the residue in 1,4-dioxane/AcOH (6 mL/0.6 mL), add 2-hydrazinopyrimidine (183 mg) and stir at 50° C. overnight. Cool to r.t., concentrate under reduced pressure, partition the residue between $NaHCO_3$ (aq. sat.) and EtOAc. Separate the layers, dry the organic phase over $MgSO_4$, concentrate under reduced pressure and purify the residue by chromatography to provide N-(Cyclopropylmethyl)-N-[1-(2-pyrimidin-2-yl-1,2,4-triazol-3-yl)ethyl]-3,5-bis(trifluoromethyl)benzamide (173 mg, 33%). LCMS (method 5): $R_t$ 2.16 min, m/z (ES+)=485 [M+H]+. Chiral HPLC: column Chiralpak AD-H (250×4.6 mm), heptane/iPrOH/diethylamine 95:5:0.1, flow rate 1.3 mL/min, T=30° C., λ 240 nm, $R_t$ 13.5 and 16.9 min.

EXAMPLE 49

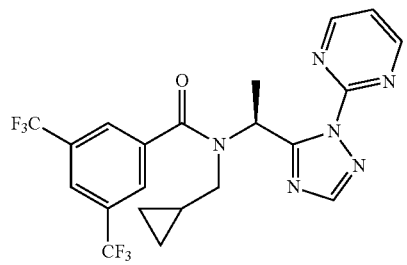 [SMILES: C[C@@H](c1ncnn1-c1ncccn1)N(CC1CC1)C(=O)c1cc(C(F)(F)F)cc(C(F)(F)F)c1]

N-(Cyclopropylmethyl)-N-[(1S)-1-(2-pyrimidin-2-yl-1,2,4-triazol-3-yl)ethyl]-3,5-bis(trifluoromethyl)benzamide (i) [(1R)-2-Amino-1-methyl-2-oxo-ethyl]4-methylbenzenesulfonate Add p-toluene sulfonyl chloride (154 g) and DIPEA (113 mL) to (R)-(+)-lactamide (48.1 g) in $CH_2Cl_2$ (1.3 L) at 0° C., warm to r.t. and stir for 3 days. Concentrate under reduced pressure, partition between $NaHCO_3$ (aq. sat.) and EtOAc, separate the layers, dry the organic phase over $MgSO_4$, filter, concentrate under reduced pressure and dissolve the residue in $CH_2Cl_2$. Add pentane, filter the precipitate and partition again between $NaHCO_3$ (aq. sat.) and EtOAc, separate the layers, dry the organic phase over $MgSO_4$, filter, concentrate under reduced pressure to provide [(1R)-2-amino-1-methyl-2-oxo-ethyl]4-methylbenzenesulfonate (69.7 g, 48%). $^1$H NMR (400 MHz, DMSO-$d_6$) δ ppm 1.31 (3 H, d, J 6.9 Hz), 2.43 (3 H, s), 4.70 (1 H, q, J 6.9 Hz), 7.29 (1 H, br s), 7.43-7.54 (2 H, m), 7.80-7.85 (2 H, m).

(ii) (2S)-2-(Cyclopropylmethylamino)propanamide

Mix cyclopropylmethanamine (44 mL), [(R)-2-amino-1-methyl-2-oxo-ethyl]4-methylbenzenesulfonate (69.3 g) and $K_2CO_3$ (107 g) in acetonitrile (700 mL) and stir at 30° C. for 6 h. Cool to r.t., filter through Celite® and wash with acetonitrile. Concentrate the filtrate under reduced pressure and purify the residue by chromatography to provide (2S)-2-(cyclopropylmethylamino)propanamide (29.7 g, 81%). $^1$H NMR (400 MHz, $CDCl_3$) δ ppm 0.09-0.18 (2 H, m), 0.44-0.57 (2 H, m), 0.87-0.98 (1 H, m), 1.35 (3 H, d, J 6.9 Hz), 1.60 (1 H, br s), 2.40 (1 H, dd, J 12.1, 7.3 Hz), 2.54 (1 H, dd, J 12.1, 6.6 Hz), 3.21 (1 H, q, J 6.9 Hz), 5.31 (1 H, br s), 7.14 (1 H, br s).

(iii) N-[(1S)-2-Amino-1-methyl-2-oxo-ethyl]-N-(cyclopropylmethyl)-3,5-bis(trifluoromethyl)benzamide Add T3P® (≥50 wt. % in EtOAc, 185 mL) and 3,5-bis(trifluoromethyl)benzoic acid (64.3 mg) to a solution of DIPEA (109 mL) and (2S)-2-(cyclopropylmethylamino)propanamide (29.5 g) in EtOAc (590 mL) and stir at r.t. overnight. Partition between water and EtOAc, separate the layers, wash the organic phase with water, $NH_4Cl$ (aq. sat.) and NaOH (aq. 1 M). Dry the organic phase over $MgSO_4$, filter, concentrate under reduced pressure and purify the residue by precipitation from $CH_2Cl_2$ and pentane to provide N-[(1S)-2-amino-1-methyl-2-oxo-ethyl]-N-(cyclopropylmethyl)-3,5-bis(trifluoromethyl)benzamide (49.1 g, 62%). LCMS: (method 4) $R_t$ 1.61 min, m/z (ES+)=383 $[M+H]^+$.

(iv) N-(Cyclopropylmethyl)-N-[(1S)-1-(2-pyrimidin-2-yl-1,2,4-triazol-3-yl)ethyl]-3,5-bis(trifluoromethyl)benzamide Add N,N-dimethylamide dimethylacetal (25.5 mL) to a solution of N-[(1S)-2-amino-1-methyl-2-oxo-ethyl]-N-(cyclopropylmethyl)-3,5-bis(trifluoromethyl)benzamide (48.7 g) in $CH_2Cl_2$ (490 mL) and stir at reflux for 1 h 15 min. Cool to r.t., concentrate under reduced pressure, dissolve the residue in 1,4-dioxane/AcOH (275 mL/275 mL), add 2-hydrazinopyrimidine (16.9 g) and stir at 50° C. overnight. Cool to r.t., concentrate under reduced pressure, and partition the residue between water and EtOAc. Filter through Celite®, separate the layers, wash the organic phase with $NaHCO_3$ (aq. sat.), dry the organic phase over $MgSO_4$, concentrate under reduced pressure and purify the residue by chromatography and precipitation from diethyl ether and petroleum ether to provide N-(cyclopropylmethyl)-N-[(1S)-1-(2-pyrimidin-2-yl-1,2,4-triazol-3-yl)ethyl]-3,5-bis(trifluoromethyl)benzamide (29.7 g, 48%). LCMS: (method 4) $R_t$ 1.79 min, m/z (ES)=485 $[M+H]^+$. Chiral HPLC: column Chiralpak AD-H (250×4.6 mm), heptane/iPrOH/diethylamine 95:5:0.1, flow rate 1.3 mL/min, T=30° C., λ 240 nm, $R_t$ 13.5 min, ($R_t$ for R-enantiomer 16.9 min) ee >99%.

EXAMPLE 75

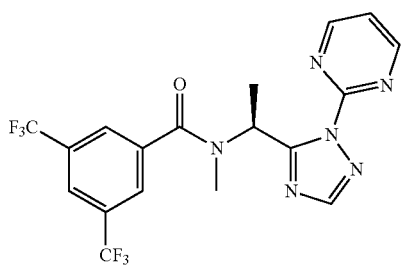 [SMILES: C[C@@H](c1ncnn1-c1ncccn1)N(C)C(=O)c1cc(C(F)(F)F)cc(C(F)(F)F)c1]

N-Methyl-N-[(1S)-1-(2-pyrimidin-2-yl-1,2,4-triazol-3-yl)ethyl]-3,5-bis(trifluoromethyl)benzamide

(i) [(1R)-2-Amino-1-methyl-2-oxo-ethyl]4-methylbenzenesulfonate

Add p-toluene sulfonyl chloride (891 mg) and DIPEA (2.1 mL) to (R)-(+)-lactamide (891 mg) in $CH_2Cl_2$ (10 mL) and stir at r.t. for 2 days. Concentrate under reduced pressure, partition between $NaHCO_2$ (aq. sat.) and EtOAc, separate the layers, dry the organic phase over $MgSO_4$, filter, concentrate under reduced pressure and purify by chromatography to provide [(1R)-2-amino-1-methyl-2-oxo-ethyl]4-methylbenzenesulfonate (1.32 g, 54%). LCMS: (method 4) $R_t$ 0.71 min, m/z (ES+)=244 $[M+H]^+$.

(ii) (2S)-2-(Methylamino)propanamide

Mix methanamine (2 M in THF, 1 mL), [(1R)-2-amino-1-methyl-2-oxo-ethyl]4-methylbenzenesulfonate (243 mg) and $K_2CO_3$ (419 mg) in acetonitrile (1 mL) and stir at r.t. overnight. Filter through Celite® and wash with acetonitrile. Concentrate the filtrate under reduced pressure to provide (2S)-2-(methylamino)propanamide (50% w., 46 mg, 22%). $^1$H NMR (400 MHz, DMSO-$d_6$) δ ppm 1.09 (3 H, d, J 6.94 Hz), 1.84 (1 H, br s), 2.19 (3 H, s), 2.86 (1 H, q, J 6.81 Hz), 6.94 (1 H, br s), 7.25 (1 H, br s).

(iii) N-[(1S)-2-Amino-1-methyl-2-oxo-ethyl]-N-methyl-3,5-bis(trifluoromethyl)benzamide Add T3P® (≥50 wt. % in EtOAc, 320 μL) and 3,5-bis(trifluoromethyl)benzoic acid (70 mg) to a solution of DIPEA (140 μL) and (2S)-2-(methylamino)propanamide (50% w., 46 mg) in DMF (1.3 mL) and stir at r.t. overnight. Partition between water and EtOAc, separate the layers, extract the aqueous phase once with EtOAc, wash the combined organic extracts with NaCl (aq. sat.). Dry the organic phase over $MgSO_4$, filter, concentrate under reduced pressure and purify the residue by chromatography to provide N-[(1S)-2-amino-1-methyl-2-oxo-ethyl]-N-methyl-3,5-bis(trifluoromethyl)benzamide (90% w. purity, 82 mg, 80%). LCMS: (method 4) $R_t$ 1.28 min, m/z (ES−)=341 $[M-H]^-$.

(iv) N-Methyl-N-[(1S)-1-(2-pyrimidin-2-yl-1,2,4-triazol-3-yl)ethyl]-3,5-bis(trifluoromethyl)benzamide Add N,N-dimethylamide dimethylacetal (38 μL) to a solution of N-[(1S)-2-amino-1-methyl-2-oxo-ethyl]-N-(methyl)-3,5-bis(trifluoromethyl)benzamide (90% w. purity, 72 mg) in $CH_2Cl_2$ (2 mL) and stir at reflux for 1.5 h. Cool to r.t., concentrate under reduced pressure, dissolve the residue in 1,4-dioxane/AcOH (0.5 mL/0.5 mL), add 2-hydrazinopyrimidine (25 mg) and stir at 50° C. overnight. Cool to r.t., concentrate under reduced pressure, and partition the residue between water and EtOAc. Filter through Celite®, separate the layers, wash the organic phase with NaCl (aq. sat.), dry the organic phase over $MgSO_4$, concentrate under reduced pressure and purify the residue by chromatography to provide N-methyl-N-[(1S)-1-(2-pyrimidin-2-yl-1,2,4-triazol-3-yl)ethyl]-3,5-bis(trifluoromethyl)benzamide (41 mg, 49%). LCMS: (method 4) $R_t$ 1.50 min, m/z (ES+)=445 $[M+H]^+$. Chiral HPLC: column Diacel Chiralpak IC-3 (150× 4.6 mm), 0.1% TFA in $H_2O$/0.1% TFA in MeCN 48:52, flow rate 0.3 mL/min. T=25° C., λ 235 nm. $R_t$ 16.4 min ($R_t$ for R-enantiomer 15.4 min), ee 99.3%.

Analytical Methods

Analysis of the samples is in each case done using a Waters Autopurification (HPLC/MS) system or an Agilent Autopurification (HPLC/MS) system with a reversed phase column using one of the methods described below. The samples are characterized by m/z and retention time or by NMR spectroscopy using a Bruker Avance 400 spectrometer.

Method 1:
 Column: Xterra MS C18 5 µm×4.6 mm×50 mm
 Eluent: water (A) and acetonitrile (B)
 Flow rate: 0.6 mL/min
 Gradient:

| Time [min] | A [%] | B [%] |
| --- | --- | --- |
| 0 | 90 | 10 |
| 2.0 | 5 | 95 |
| 4.0 | 5 | 95 |

Method 2:
 Column: Xterra MS C18 5 µm×4.6 mm×50 mm
 Eluent: 0.1% formic acid in water (A) and 0.1% formic acid in acetonitrile (B)
 Flow rate: 2 mL/min
 Gradient:

| Time [min] | A [%] | B [%] |
| --- | --- | --- |
| 0 | 70 | 30 |
| 0.5 | 70 | 30 |
| 2.5 | 5 | 95 |
| 2.8 | 5 | 95 |
| 2.9 | 70 | 30 |
| 3.0 | 70 | 30 |

Method 3:
 Column: Bischoff SC-03-150 Daisogel SP-120-ODS-AP 5.0 µm×3.0 mm×150 mm
 Eluent: 0.1% formic acid in water (A) and 0.1% formic acid in acetonitrile (B)
 Flow rate: 2 mL/min
 Gradient:

| Time [min] | A [%] | B [%] |
| --- | --- | --- |
| 0 | 90 | 10 |
| 5.5 | 5 | 95 |
| 6.0 | 5 | 95 |
| 6.5 | 90 | 10 |
| 7.0 | 90 | 10 |

Method 4:
 Column: Xterra MS C18, 5 µm×4.6 mm×50 mm
 Eluent: 0.1% formic acid in water (A) and 0.1% formic acid in acetonitrile (B)
 Flow rate: 2 mL/min
 Gradient:

| Time [min] | A [%] | B [%] |
| --- | --- | --- |
| 0 | 65 | 35 |
| 0.5 | 65 | 35 |
| 2.5 | 5 | 95 |
| 2.8 | 5 | 98 |
| 2.9 | 65 | 35 |
| 3.0 | 65 | 35 |

Method 5:
 Column: XBridge C18 5 µm×2.1 mm×50 mm
 Eluent: 0.1% formic acid in water (A) and 0.1% formic acid in acetonitrile (B)
 Flow rate: 0.6 mL/min
 Gradient:

| Time [min] | A [%] | B [%] |
| --- | --- | --- |
| 0 | 90 | 10 |
| 0.3 | 90 | 10 |
| 3.3 | 5 | 95 |
| 4.0 | 5 | 95 |

Method 6:
 Column: XBridge C18 2.5 µm×2.1 mm×50 mm
 Eluent: 0.5% ammonia in water (A) and 0.5% ammonia in acetonitrile (B)
 Flow rate: 0.6 mL/min
 Gradient:

| Time [min] | A [%] | B [%] |
| --- | --- | --- |
| 0 | 90 | 10 |
| 0.3 | 90 | 10 |
| 3.3 | 5 | 95 |
| 4.0 | 5 | 95 |

Method 7:
 Column: BEH C18 1.7 µm×2.1 mm×50 mm
 Eluent: 5 mM ammonium acetate+0.1% formic acid in water (A) and 0.1% formic acid in acetonitrile (B)
 Flow rate: 0.55 mL/min
 Gradient:

| Time [min] | A [%] | B [%] |
| --- | --- | --- |
| 0 | 95 | 5 |
| 0.4 | 95 | 5 |
| 0.8 | 65 | 35 |
| 1.2 | 45 | 55 |
| 2.5 | 0 | 100 |
| 3.3 | 0 | 100 |
| 3.31 | 95 | 5 |
| 4.0 | 95 | 5 |

Method 8:
 Column: XBridge C18 3.5 µm×4.6 mm×50 mm
 Eluent: 0.1% ammonia in water (A) and 0.1% ammonia in acetonitrile (B)
 Flow rate: 1.00 mL/min
 Gradient:

| Time [min] | A [%] | B [%] |
| --- | --- | --- |
| 0.01 | 95 | 5 |
| 5.00 | 10 | 90 |
| 5.80 | 5 | 95 |
| 7.20 | 5 | 95 |
| 7.21 | 95 | 5 |
| 10.00 | 95 | 5 |

All of the exemplified compounds of Examples 1 to 49 exhibited one or more of the following: greater than 80% efficacy ($EC_{80}$) at 32 ppm in the in vitro cat flea assay (Assay A); greater than 80% efficacy ($EC_{80}$) at 3.2 ppm in the in vitro Australian sheep blow fly assay (Assay A); or greater than 80% efficacy ($EC_{80}$) at 10 ppm in the in vitro dog tick assay (Assay A). All of the exemplified compounds of Examples 50 to 75 exhibited one or more of the following: greater than 50% efficacy ($EC_{80}$) at 10 ppm in the in vitro cat flea assay (Assay B); greater than 50% efficacy ($EC_{80}$) at 10 ppm in the in vitro Australian sheep blow fly assay (Assay B); or greater than 50% efficacy ($EC_{50}$) at 20 ppm in the in vitro dog tick assay (Assay B).

Activity In Vitro Against *Ctenocephalides Felis* (Cat Flea)—Assay A

A mixed adult population of fleas is placed in a suitably formatted 96-well plate allowing fleas to access and feed on treated blood via an artificial feeding system. Fleas are fed on treated blood for 24 h, after which the compound effect is recorded. Insecticidal activity is determined on the basis of the number of dead fleas recovered from the feeding system. In this test the following examples showed more than 80% ($EC_{80}$) efficacy at 100 ppm: 1 to 11, 13 to 22, 24 to 32 and 34 to 49.

In this test the compound of Example 18 showed an $EC_{80}$ of 10 ppm.

Activity In Vitro Against *Ctenocephalides Felis* (Cat Flea)—Assay B

Test compounds are added to organic bovine blood contained in an artificial feeding container. Compounds with known insecticidal activity are included to serve as positive controls. Newly emerged unfed adult fleas from a laboratory colony are aspirated into each vial. The test cages are maintained using the artificial feeding apparatus to allow ingestion of compound. Fleas are evaluated for % mortality at 48 hours post infestation. Fleas showing normal movement and/or jumping ability are considered viable and those showing no movement are scored as dead. In this test the following examples showed more than 50% ($EC_{50}$) efficacy at 10 ppm: 50 to 61, 63 to 73 and 75.

In this test the compound of Example 59 showed an $EC_{50}$ of 1.6 ppm.

Activity in vitro against *Lucilla Cuprina* (Australian sheep blowfly)—Assay A

Freshly laid blowfly eggs are used to seed a suitably formatted microplate containing the test substances to be evaluated for antiparasitic activity. Each compound is tested by serial dilution in order to determine its minimum efficacy dose. The test compounds are embedded in an agar-based nutritive medium allowing the full development of the eggs into $3^{rd}$ instar larvae. The incubation lasts for 4 days at 28° C. and 60% relative humidity. Egg-hatching and ensuing larval development are also recorded to identify a possible growth-regulating activity. In this test the following examples showed more than 80% ($EC_{80}$) efficacy at 32 ppm: 1 to 4, 6 to 33, 35 to 46, 48 and 49.

In this test the compound of Example 41 showed an $EC_{50}$ of 1 ppm.

Activity In Vitro Against *Lucilla Cuprina* (Australian Sheep Blowfly)—Assay B

Compound formulated in bovine serum is dispensed into scintillation. A dental cotton roll is added to each vial to absorb the compound solution. *L. cuprina* larvae are added to each treatment vial. The vials are capped and held for 24 hours in an environmental chamber at appropriate temperature, humidity and light/dark cycles. Evaluations are only made at 24 hours because dead larvae after 24 hours may be cannibalized by the remaining live ones. Vials are examined for percent mortality. In this test the following examples showed more than 50% ($EC_{50}$) efficacy at 10 ppm: 50, 51, 53, 56 to 70, 72 and 75.

In this test the compound of Example 59 showed and $EC_{50}$ of 0.77 ppm.

Activity In Vitro Against *Rhipicephalus sanguineus* (Dog Tick)—Assay A

A contact test is performed by pre-coating microplate with serial dilution of compound allowing evaluating anti-parasitic activity by contact against ticks. A mixed adult tick population is then distributed to each well of the plate and incubated at 28° C. and 80% relative humidity for 7 days, during which the effect of the test compound is monitored. Acaricidal activity is confirmed if and when adult ticks are dead. In this test the following examples showed more than 80% ($EC_{80}$) efficacy at 100 ppm: 1 to 4, 6, 9 to 15, 19, 20, 24, 26 to 32, 34 to 43 and 47 to 49.

In this test the compound for Example 41 showed an $EC_{50}$ of 32 ppm.

Activity In Vitro Against *Rhipicephalus sanguineus* (Dog Tick)—Assay B

A solution of the test compounds is used to coat the inner wall of glass vials containing a filter paper on the bottom of each vial. A second filter paper is also coated and placed in the cap of the vial. Vials and caps are allowed to dry overnight. Each treated vial is infested with ticks. Contact of the ticks with residues is induced by holding the vials in a controlled environment and assessment is performed at 48 hours after application in comparison with untreated glass vials and solvent-treated glass vials. In this test the following examples showed more than 50% ($EC_{50}$) efficacy at 20 ppm: 50, 54, 55, 58 to 63, 65, 67 to 70 and 73 to 75.

In this test the compound of Example 59 showed an $EC_{50}$ of 14 ppm.

Activity In Vitro Against Engorged Female *Rhipicephalus microplus* (Cattle Tick)

A contact test is performed by pre-coating 6-well microplates with serial dilution of the compound to be evaluated for anti-parasitic activity. 10 engorged female ticks of the organophosphorous-resistant Ultimo strain are distributed to each well in triplicates. Plates are then incubated at 28° C. and 80% relative humidity. Evaluation takes place 28 days later based on mortality, oviposition and hatched larvae. An indication of the activity of the test compounds is shown by the number of females that:

die quickly before laying eggs,
  survive for some time without laying eggs,
  lay eggs in which no embryos are formed,
  lay eggs in which embryos form, from which no larvae hatch, and
  lay eggs in which embryos form, from which larvae normally hatch within 26 to 27 days In this test the following examples showed more than 80% ($EC_{80}$) efficacy at 200 ppm: 1 to 4, 6 to 12, 14 to 25, 35 to 41, 44 to 46 and 48.

Activity In Vivo Against *Rhipicephalus sanguineus* Nymphs on Mongolian Gerbils (*Meriones unguiculatus*) (Spray Application)

On day 0, gerbils are treated with the test compound at a given dose by pour on application. On day +1 (+2), the animals are infested with nymphs of *R. sanguineus*. Ticks are left on the animals until full repletion. Seven days after infestation nymphs dropped off fully engorged are collected and counted. They are kept until molting to also evaluate growth regulating activity of the test compound. Efficacy in killing (and growth regulating) is expressed as a tick number (and molted tick number) reduction in comparison with a placebo treated group, using the Abbott's formula:

$$\text{Corrected \%} = 100 \times \left(1 - \frac{n \text{ in } T \text{ after treatment}}{n \text{ in } Co \text{ after treatment}}\right)$$

n=number of live ticks. T=treated group. Co=control/placebo group.

In this test the following examples showed more than 90% ($EC_{90}$) efficacy at 32 mg/kg: 1, 8 to 12, 14, 16, 18 to 20, 23, 26, 28, 29, 31, 35, 37, 39 to 41, 44, 45, 48 and 49.

Activity In Vivo Against *Rhipicephalus sanguineus* Ticks (Dog Tick) on Rabbits

On day 0, rabbits are treated with the test compound at a given dose by spray application on their ears only. On day +1, the animals are infested on their ears with adult *R. sanguineus* ticks (sex ratio 1:1). Evaluation of efficacy is performed 24 h, 48 h, and 72 h after infestation by counting the numbers of dead and live ticks recovered from the animals. Efficacy is expressed as comparison with a placebo treated group using the Abbott's formula:

$$\text{Corrected \%} = 100 \times \left(1 - \frac{n \text{ in } T \text{ after treatment}}{n \text{ in } Co \text{ after treatment}}\right)$$

n=number of ticks, T=treated group, Co=control/placebo group.

In this test the following examples showed more than 90% ($EC_{90}$) efficacy at 60 mg/m²: 28, 32, 35, 40, 41 and 48.

Activity In Vivo Against Lice (*Polyplax serrata*) in Mice (Topical)

Mice naturally infected with *P. serrata* are treated with the formulated test compound on day 0 by pour-on application. On day +4 and +14, efficacy is evaluated by counting the number of live lice under a binocular. Efficacy at the two time points is expressed as a comparison of lice numbers counted on the same mouse before treatment, using the Henderson & Tilton formula, taking also into account lice numbers found on mice treated with the empty formulation (placebo group):

$$\text{Corrected \%} = 100 \times \left(1 - \frac{n \text{ in } Co \text{ before treatment} \times n \text{ in } T \text{ after treatment}}{n \text{ in } Co \text{ after treatment} \times n \text{ in } T \text{ before treatment}}\right)$$

n=number of lice, T=treated group, Co=control/placebo group.

In this test the following examples showed more than 90% ($EC_{90}$) efficacy at 32 mg/kg: 1, 7, 10 to 12, 15 to 21, 24, 25, 27, 28, 30, 35 to 41, 48 and 49.

Activity of Compounds Against Experimental Tick-Infestation with *Rhipicephalus* (*Boophilus*) *Microplus* on Cattle Studies are conducted to evaluate the curative and the prophylactic activity of the compounds against the cattle tick *R.* (*B.*) *microplus*, when administered as pour-on on experimentally infested cattle. Young adult cattle (approximately 80-250 kg, n=5 per group) are housed individually in roofed pens, but exposed to the ambient conditions.

During a 30-day acclimation phase all animals are infested three times per week in the dorsal region of the neck with approximately 5000 larvae of *R.* (*B.*) *microplus* per infestation. At the end of the acclimation-period the animals are treated with an experimental formulation that is poured on the back-line of each calf (Day 0). For the experimental formulation the compound is dissolved—as an example—in benzyl alcohol, propylene carbonate and isopropanol. The dose is set to achieve a point dose of ≤10 mg/kg bodyweight. After treatment, the infestation of the animals with *R.* (*B.*) *microplus*-larvae continues at a frequency of two infestations per week until the end of the study. Starting on Day 1 after treatment, adult engorged female ticks are collected daily from each animal according to Holdsworth et al. (W.A.A.V.P. guidelines for evaluating the efficacy of acaricides against ticks (Ixodidae) on ruminants, Vet Parasitol., 136(1):29-43(2005)). This setup allows evaluating the curative efficacy (onset of efficacy) as well as the residual protection. The infestation of the animals and the daily collection of the ticks continues until Study Day 77.

The invention claimed is:

1. A compound of the formula

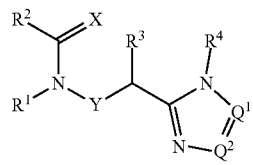

wherein:

X is O or S;

$Q^1$ and $Q^2$ are independently $CR^5$ or N, provided at least one of $Q^1$ and $Q^2$ is N;

Y is a direct bond or $CH_2$;

$R^1$ is H; $C_1$-$C_6$alkyl optionally substituted with one substituent selected from: CN, $CONH_2$, COOH, $NO_2$ and —$Si(CH_3)_3$; $C_1$-$C_6$haloalkyl; $C_2$-$C_6$alkenyl; $C_2$-$C_6$haloalkenyl; $C_2$-$C_6$alkynyl; $C_2$-$C_6$haloalkynyl; $C_3$-$C_4$cycloalkyl-$C_1$-$C_2$alkyl- wherein the $C_3$-$C_4$cycloalkyl is optionally substituted with 1 or 2 halo atoms; oxetan-3-yl-$CH_2$—; or benzyl optionally substituted with halo or $C_1$-$C_3$haloalkyl;

$R^2$ is phenyl, pyridine, pyrimidine, pyrazine or pyridazine, wherein the phenyl, pyridine, pyrimidine, pyrazine or pyridazine is optionally substituted with one to three substituents, provided the substituent(s) are not on either carbon adjacent to the carbon bonded to the

group, each independently selected from: $C_1$-$C_3$alkyl, $C_1$-$C_3$haloalkyl, $C_1$-$C_3$thiohaloalkyl, $C_1$-$C_3$alkoxy, $C_1$-$C_3$haloalkoxy, halo, $NO_2$, $SF_5$, CN, $CONH_2$, COOH and $C(S)NH_2$;

$R^3$ is $C_1$-$C_3$alkyl or $C_1$-$C_3$haloalkyl;

$R^4$ is pyridine, pyrimidine, pyrazine or pyridazine, wherein the pyridine, pyrimidine, pyrazine or pyridazine is optionally substituted with one substituent selected from: $C_1$-$C_3$alkyl, $C_1$-$C_3$haloalkyl, $C_1$-$C_3$alkoxy, $C_3$-$C_4$cycloalkyl, halo or hydroxy; and $R^5$ is H, $C_1$-$C_3$alkyl, $C_1$-$C_3$haloalkyl, $C_3$-$C_4$cycloalkyl, $C_1$-$C_3$alkoxy, $C_1$-$C_3$alkoxyC(O)— or $(C_1$-$C_3$alkoxy)$_2$CH—;

or a salt thereof.

2. The compound or salt according to claim 1, wherein Y is a direct bond.

3. The compound or salt according to claim 1, wherein X is O.

4. The compound or salt according to claim 1, wherein $R^3$ is methyl.

5. The compound or salt according to claim 1, wherein $Q^1$ is N, $Q^2$ is $CR^5$, and $R^5$ is H, methyl, or $(CH_3CH_2O)_2CH$—.

6. The compound or salt according to claim 1, wherein $R^4$ is 2-pyridine, or 2-pyrimidine optionally substituted by $C_1$-$C_3$ alkoxy.

7. The compound or salt according to claim 6, wherein $R^4$ is 2-pyrimidine.

8. The compound or salt according to claim 1, wherein $R^1$ is cyclopropyl-CH$_2$—, n-propyl, CH≡C—CH$_2$—, CF$_3$CH$_2$CH$_2$—, FCH$_2$CH$_2$—, FCH$_2$CH$_2$CH$_2$—, 2,2-difluorocyclopropyl-CH$_2$—, 2,2-dichlorocyclopropyl-CH$_2$—, H, CH$_3$, (CH$_3$)$_3$SiCH$_2$—, CH$_3$CH$_2$— or CNCH$_2$—.

9. The compound or salt according to claim 8, wherein $R^1$ is cyclopropyl-CH$_2$—, CH≡C—CH$_2$—, H or CH$_3$.

10. The compound or salt according to claim 1, wherein $R^2$ is 3,5-bis(trifluoromethyl)phenyl, 3,5-dichlorophenyl, 3-trifluoromethoxyphenyl, 3-chloro-5-trifluoromethylphenyl, 3-cyanophenyl, 3-chloro-5-trifluoromethoxyphenyl, 5-trifluoromethylpyridin-3-yl, 3-bromo-5-trifluoromethylphenyl, 3-cyano-5-trifluoromethylphenyl or 2,6-bis(trifluoromethyl)pyridin-4-yl.

11. The compound or salt according to claim 10, wherein $R^2$ is 3,5-bis(trifluoromethyl)phenyl.

12. A formulation comprising a compound or salt according to claim 1, and at least one acceptable carrier.

13. A method of controlling ectoparasites on an animal in need thereof comprising administering an effective amount of the compound or salt according to claim 1.

14. The compound or salt according to claim 1, which is:
- N-(Cyclopropylmethyl)-N-[1-[2-(2-pyridyl)-1,2,4-triazol-3-yl]ethyl]-3,5-bis(trifluoromethyl)benzamide;
- 3,5-Dichloro-N-(cyclopropylmethyl)-N-[1-[2-(2-pyridyl)-1,2,4-triazol-3-yl]ethyl]benzamide;
- 3,5-Dichloro-N-propyl-N-[1-[2-(2-pyridyl)-1,2,4-triazol-3-yl]ethyl]benzamide;
- N-(Cyclopropylmethyl)-N-[1-[2-(2-pyridyl)-1,2,4-triazol-3-yl]ethyl]-3-(trifluoromethoxy)benzamide;
- N-[(3-Chlorophenyl)methyl]-3-cyano-N-[1-[2-(2-pyridyl)-1,2,4-triazol-3-yl]ethyl]benzamide;
- 3-Chloro-N-(cyclopropylmethyl)-N-[1-[2-(2-pyridyl)-1,2,4-triazol-3-yl]ethyl]-5-(trifluoromethyl)benzamide;
- 3-Chloro-N-prop-2-ynyl-N-[1-[2-(2-pyridyl)-1,2,4-triazol-3-yl]ethyl]-5-(trifluoromethyl)benzamide;
- 3-Chloro-N-propyl-N-[1-[2-(2-pyridyl)-1,2,4-triazol-3-yl]ethyl]-5-(trifluoromethyl)benzamide;
- N-(Cyclopropylmethyl)-N-[1-[2-(2-pyridyl)-1,2,4-triazol-3-yl]ethyl]-5-(trifluoromethyl)pyridine-3-carboxamide;
- 3-Chloro-N-(cyclopropylmethyl)-N-[1-[2-(2-pyridyl)-1,2,4-triazol-3-yl]ethyl]-5-(trifluoromethoxy)benzamide;
- N-(2-Fluoroethyl)-N-[1-[2-(2-pyridyl)-1,2,4-triazol-3-yl]ethyl]-3,5-bis(trifluoromethyl)benzamide;
- N-[1-[2-(2-Pyridyl)-1,2,4-triazol-3-yl]ethyl]-3,5-b is (trifluoromethyl)-N-(3,3,3-trifluoropropyl)benzamide;
- N-(Oxetan-3-ylmethyl)-N-[1-[2-(2-pyridyl)-1,2,4-triazol-3-yl]ethyl]-3,5-bis(trifluoromethyl)benzamide;
- N-(Cyanomethyl)-N-[1-[2-(2-pyridyl)-1,2,4-triazol-3-yl]ethyl]-3,5-bis(trifluoromethyl)benzamide;
- N-Prop-2-ynyl-N-[1-[2-(2-pyridyl)-1,2,4-triazol-3-yl]ethyl]-3,5-bis(trifluoromethyl)benzamide;
- N-[(2,2-Difluorocyclopropyl)methyl]-N-[1-[2-(2-pyridyl)-1,2,4-triazol-3-yl]ethyl]-3,5-bis(trifluoromethyl)benzamide;
- N-[(2,2-Dichlorocyclopropyl)methyl]-N-[1-[2-(2-pyridyl)-1,2,4-triazol-3-yl]ethyl]-3,5-bis(trifluoromethyl)benzamide;
- 3-Chloro-N-prop-2-ynyl-N-[1-[2-(2-pyridyl)-1,2,4-triazol-3-yl]ethyl]-5-(trifluoromethoxy)benzamide;
- N-(Fluoroethyl)-N-[1-(2-pyrimidin-2-yl-1,2,4-triazol-3-yl)ethyl]-3,5-bis(trifluoromethyl)benzamide;
- N-[1-(2-Pyrimidin-2-yl-1,2,4-triazol-3-yl)ethyl]-3,5-bis(trifluoromethyl)-N-(3,3,3-trifluoropropyl)benzamide;
- N-(3-Fluoropropyl)-N-[1-(2-pyrimidin-2-yl-1,2,4-triazol-3-yl)ethyl]-3,5-bis(trifluoromethyl)benzamide;
- 3-Chloro-N-(2-fluoroethyl)-N-[1-(2-pyrimidin-2-yl-1,2,4-triazol-3-yl)ethyl]-5-(trifluoromethoxy)benzamide;
- 3-Chloro-N-(2-fluoroethyl)-N-[1-(2-pyrimidin-2-yl-1,2,4-triazol-3-yl)ethyl]-5-(trifluoromethyl)benzamide;
- 3-Chloro-N-(3-fluoropropyl)-N-[1-(2-pyrimidin-2-yl-1,2,4-triazol-3-yl)ethyl]-5-(trifluoromethyl)benzamide;
- 3-Chloro-N-(3-fluoropropyl)-N-[1-(2-pyrimidin-2-yl-1,2,4-triazol-3-yl)ethyl]-5-(trifluoromethoxy)benzamide;
- 3-Chloro-N-[1-(2-pyrimidin-2-yl-1,2,4-triazol-3-yl)ethyl]-5-(trifluoromethyl)-N-(3,3,3-trifluoropropyl)benzamide;
- 3-Chloro-N-[1-(2-pyrimidin-2-yl-1,2,4-triazol-3-yl)ethyl]-5-(trifluoromethoxy)-N-(3,3,3-trifluoropropyl)benzamide;
- N-(Cyclopropylmethyl)-N-[1-(2-pyrimidin-2-yl-1,2,4-triazol-3-yl)ethyl]-5-(trifluoromethyl)pyridine-3-carboxamide;
- N-[1-(2-Pyrimidin-2-yl-1,2,4-triazol-3-yl)ethyl]-5-(trifluoromethyl)-N-(3,3,3-trifluoropropyl)pyridine-3-carboxamide;
- N-(2-Fluoroethyl)-N-[1-(2-pyrimidin-2-yl-1,2,4-triazol-3-yl)ethyl]-5-(trifluoromethyl)pyridine-3-carboxamide;
- N-(3-Fluoropropyl)-N-[1-(2-pyrimidin-2-yl-1,2,4-triazol-3-yl)ethyl]-5-(trifluoromethyl)pyridine-3-carboxamide;
- N-Prop-2-ynyl-N-[1-(2-pyrimidin-2-yl-1,2,4-triazol-3-yl)ethyl]-5-(trifluoromethyl)pyridine-3-carboxamide;
- N-(Cyclopropylmethyl)-N-[1-(1-pyrimidin-2-yltetrazol-5-yl)ethyl]-3,5-bis(trifluoromethyl)benzamide;
- 3-Cyano-N-(cyclopropylmethyl)-N-[1-[5-methyl-2-(2-pyridyl)-1,2,4-triazol-3-yl]ethyl]benzamide;
- N-Prop-2-ynyl-N-[1-(2-pyrimidin-2-yl-1,2,4-triazol-3-yl)ethyl]-3,5-bis(trifluoromethyl)benzamide;
- 3-Chloro-N-prop-2-ynyl-N-[1-(2-pyrimidin-2-yl-1,2,4-triazol-3-yl)ethyl]-5-(trifluoromethoxy)-benzamide;
- 3-chloro-N-(cyclopropylmethyl)-N-[1-(2-pyrimidin-2-yl-1,2,4-triazol-3-yl)ethyl]-5-(trifluoromethoxy)benzamide;
- 3-Cyano-N-(cyclopropylmethyl)-N-[1-(2-pyrimidin-2-yl-1,2,4-triazol-3-yl)ethyl]benzamide;
- N-(Cyclopropylmethyl)-N-[1-[2-(5-methoxypyrimidin-2-yl)-1,2,4-triazol-3-yl]ethyl]-3,5-bis(trifluoromethyl)benzamide;
- 3-Chloro-N-(cyclopropylmethyl)-N-[1-(2-pyrimidin-2-yl-1,2,4-triazol-3-yl)ethyl]-5-(trifluoromethyl)benzamide;
- 3-Chloro-N-prop-2-ynyl-N-[1-(2-pyrimidin-2-yl-1,2,4-triazol-3-yl)ethyl]-5-(trifluoromethyl)benzamide;
- N-(Cyclopropylmethyl)-N-[2-[2-(2-pyridyl)-1,2,4-triazol-3-yl]propyl]-3,5-bis(trifluoromethyl)benzamide;
- N-Prop-2-ynyl-N-[(1S)-1-(2-pyrimidin-2-yl-1,2,4-triazol-3-yl)ethyl]-5-(trifluoromethyl)pyridine-3-carboxamide;
- N-(Cyclopropylmethyl)-N-R1S)-1-[2-(2-pyridyl)-1,2,4-triazol-3-yl]ethyl]-3,5-bis(trifluoromethyl)benzamide;
- N-(Cyclopropylmethyl)-N-R1S)-1-(2-pyrimidin-2-yl-1,2,4-triazol-3-yl)ethyl]-5-(trifluoromethyl)pyridine-3-carboxamide;
- N-Prop-2-ynyl-N-[(1S)-1-(2-pyrimidin-2-yl-1,2,4-triazol-3-yl)ethyl]-3,5-bis(trifluoromethyl)benzamide;
- 3-Cyano-N-(cyclopropylmethyl)-N-[1-[2-(2-pyridyl)-1,2,4-triazol-3-yl]ethyl]benzenecarbothioamide;
- N-(Cyclopropylmethyl)-N-[1-(2-pyrimidin-2-yl-1,2,4-triazol-3-yl)ethyl]-3,5-bis(trifluoromethyl)benzamide;

N-(Cyclopropylmethyl)-N-R1S)-1-(2-pyrimidin-2-yl-1,2,4-triazol-3-yl)ethyl]-3,5-bis(trifluoromethyl)benzamide;

3-Cyano-N-(cyclopropylmethyl)-N-[1-(2-pyrimidin-2-yl-1,2,4-triazol-3-yl)ethyl]-5-(trifluoromethyl)benzamide;

N-(Cyclopropylmethyl)-N-[1-(2-pyrimidin-2-yl-1,2,4-triazol-3-yl)ethyl]-2,6-bis(trifluoromethyl)pyridine-4-carboxamide;

3-Cyano-N-[1-(2-pyrimidin-2-yl-1,2,4-triazol-3-yl)ethyl]benzamide;

N-Ethyl-N-[1-(2-pyrimidin-2-yl-1,2,4-triazol-3-yl)ethyl]-3,5-bis(trifluoromethyl)benzamide;

3-Cyano-N-prop-2-ynyl-N-[1-(2-pyrimidin-2-yl-1,2,4-triazol-3-yl)ethyl]benzamide;

3-Cyano-N-methyl-N-[1-(2-pyrimidin-2-yl-1,2,4-triazol-3-yl)ethyl]benzamide;

N-(Cyanomethyl)-N-[1-(2-pyrimidin-2-yl-1,2,4-triazol-3-yl)ethyl]-3,5-bis(trifluoromethyl)benzamide;

3-Cyano-N-[1-(2-pyrimidin-2-yl-1,2,4-triazol-3-yl)ethyl]-5-(trifluoromethyl)benzamide;

3-Cyano-N-prop-2-ynyl-N-[1-(2-pyrimidin-2-yl-1,2,4-triazol-3-yl)ethyl]-5-(trifluoromethyl)benzamide;

3-Cyano-N-ethyl-N-[1-(2-pyrimidin-2-yl-1,2,4-triazol-3-yl)ethyl]-5-(trifluoromethyl)benzamide;

3-Cyano-N-methyl-N-[1-(2-pyrimidin-2-yl-1,2,4-triazol-3-yl)ethyl]-5-(trifluoromethyl)benzamide;

N-(Cyclopropylmethyl)-N-[1-(5-methyl-2-pyrimidin-2-yl-1,2,4-triazol-3-yl)ethyl]-3,5-bis(trifluoromethyl)benzamide;

3-Bromo-N-(cyclopropylmethyl)-N-[1-(2-pyrimidin-2-yl-1,2,4-triazol-3-yl)ethyl]-5-(trifluoromethyl)benzamide;

N-[1-(2-Pyrimidin-2-yl-1,2,4-triazol-3-yl)ethyl]-3,5-bis(trifluoromethyl)benzamide;

N-(Cyclopropylmethyl)-N-R1S)-1-[2-(5-fluoropyrimidin-2-yl)-1,2,4-triazol-3-yl]ethyl]-3,5-bis(trifluoromethyl)benzamide;

N-Methyl-N-[1-(2-pyrimidin-2-yl-1,2,4-triazol-3-yl)ethyl]-3,5-bis(trifluoromethyl)benzamide;

N-[(1S)-1-(2-Pyrimidin-2-yl-1,2,4-triazol-3-yl)ethyl]-3,5-bis(trifluoromethyl)benzamide;

N-[1-(2-pyrimidin-2-yl-1,2,4-triazol-3-yl)ethyl]-3,5-bis(trifluoromethyl)-N-(trimethylsilylmethyl)benzamide;

3-Cyano-N-R1S)-1-[2-(5-fluoropyrimidin-2-yl)-1,2,4-triazol-3-yl]ethyl]benzamide;

N-R1S)-1-[2-(5-Fluoropyrimidin-2-yl)-1,2,4-triazol-3-yl]ethyl]-3,5-bis(trifluoromethyl)benzamide;

N-(Cyclopropylmethyl)-N-R1S)-1-(2-pyrimidin-2-yl-1,2,4-triazol-3-yl)ethyl]-3,5-bis(trifluoromethyl)bentenecarbothioamide;

3-Carbamothioyl-N-methyl-N-[1-(2-pyrimidin-2-yl-1,2,4-triazol-3-yl)ethyl]benzamide;

3-Carbamothioyl-N-methyl-N-[1-(2-pyrimidin-2-yl-1,2,4-triazol-3-yl)ethyl]-5-(trifluoromethyl)benzamide;

N-[1-[5-(Diethoxymethyl)-2-pyrimidin-2-yl-1,2,4-triazol-3-yl]ethyl]-3,5-bis(trifluoromethyl)benzamide;

Methyl5-[1-[[3,5-bis(trifluoromethyl)benzoyl]amino]ethyl]-1-pyrimidin-2-yl-1,2,4-triazole-3-carboxylate; or N-Methyl-N-R1S)-1-(2-pyrimidin-2-yl-1,2,4-triazol-3-yl)ethyl]-3,5-bis(trifluoromethyl)benzamide.

15. The compound or salt according to claim 1, which is N-(cyclopropylmethyl)-N-[(1S)-1-(2-pyrimidin-2-yl-1,2,4-triazol-3-yl)ethyl]-3,5-bis(trifluoromethyl)benzamide, N-Prop-2-ynyl-N-[(1S)-1-(2-pyrimidin-2-yl-1,2,4-triazol-3-yl)ethyl]-3,5-bis(trifluoromethyl)benzamide or N-methyl-N-[(1S)-1-(2-pyrimidin-2-yl-1,2,4-triazol-3-yl)ethyl]-3,5-bis(trifluoromethyl)benzamide.

16. A compound that is N-R1S)-1-(2-Pyrimidin-2-yl-1,2,4-triazol-3-yl)ethyl]-3,5-bis(trifluoromethyl)benzamide or a salt thereof.

17. A compound that is N-[(1S)-1-(2-Pyrimidin-2-yl-1,2,4-triazol-3-yl)ethyl]-3,5-bis(trifluoromethyl)benzamide.

* * * * *

UNITED STATES PATENT AND TRADEMARK OFFICE
CERTIFICATE OF CORRECTION

Page 1 of 1

PATENT NO. : 10,287,276 B2
APPLICATION NO. : 15/556722
DATED : May 14, 2019
INVENTOR(S) : Paolo Tosatti and Jean-Yves Wach It is certified that error appears in the above-identified patent and that said Letters Patent is hereby corrected as shown below:

In the Claims

In Claim 14, Column 83, Line 48, delete "-b is (" and insert -- -bis( --, therefor.

In Claim 14, Column 84, Line 57, delete "-N-R1S)-" and insert -- -N-[(1S)- --, therefor.

In Claim 14, Column 84, Line 59, delete "-N-R1S)-" and insert -- -N-[(1S)- --, therefor.

In Claim 14, Column 85, Line 1, delete "-N-R1S)-" and insert -- -N-[(1S)- --, therefor.

In Claim 14, Column 85, Line 35, delete "-N-R1S)-" and insert -- -N-[(1S)- --, therefor.

In Claim 14, Column 86, Line 7, delete "-N-R1S)-" and insert -- -N-[(1S)- --, therefor.

In Claim 14, Column 86, Line 9, delete "N-R1S)-" and insert -- N-[(1S)- --, therefor.

In Claim 14, Column 86, Line 11, delete "-N-R1S)-" and insert -- -N-[(1S)- --, therefor.

In Claim 14, Column 86, Lines 12-13, delete ")bentenecarbothioamide;" and insert -- )benzenecarbothioamide; --, therefor.

In Claim 14, Column 86, Line 20, delete "Methyl5-" and insert -- Methyl 5- --, therefor.

In Claim 14, Column 86, Line 23, delete "-N-R1S)-" and insert -- -N-[(1S)- --, therefor.

In Claim 16, Column 86, Line 32, delete "N-R1S)-" and insert -- N-[(1S)- --, therefor.

Signed and Sealed this
Seventeenth Day of December, 2019

Andrei Iancu
*Director of the United States Patent and Trademark Office*